(12) United States Patent
Xu et al.

(10) Patent No.: US 11,975,081 B2
(45) Date of Patent: May 7, 2024

(54) BIFUNCTIONAL CHELATORS AND CONJUGATES

(71) Applicant: ACTINIUM PHARMACEUTICALS, INC., New York, NY (US)

(72) Inventors: Le-Cun Xu, Yonkers, NY (US); Denis Beckford Vera, Valhalla, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 0 days.

(21) Appl. No.: 18/481,844

(22) Filed: Oct. 5, 2023

(65) Prior Publication Data

US 2024/0082438 A1    Mar. 14, 2024

Related U.S. Application Data

(63) Continuation of application No. PCT/US2023/068062, filed on Jun. 7, 2023.

(60) Provisional application No. 63/487,789, filed on Mar. 1, 2023, provisional application No. 63/408,970, filed on Sep. 22, 2022, provisional application No. 63/349,833, filed on Jun. 7, 2022.

(51) Int. Cl.
*C07D 257/02* (2006.01)
*A61K 51/04* (2006.01)
*A61K 51/10* (2006.01)

(52) U.S. Cl.
CPC ...... *A61K 51/1093* (2013.01); *A61K 51/0482* (2013.01); *C07D 257/02* (2013.01)

(58) Field of Classification Search
CPC ............ A61K 51/1093; A61K 51/0482; C07D 257/02
See application file for complete search history.

(56) References Cited

U.S. PATENT DOCUMENTS

| | | | |
|---|---|---|---|
| 4,704,692 A | 11/1987 | Ladner | |
| 4,946,778 A | 8/1990 | Ladner et al. | |
| 6,120,768 A | 9/2000 | Griffiths et al. | |
| 6,683,162 B2 | 1/2004 | Scheinberg et al. | |
| 7,238,785 B2 | 7/2007 | Govindan et al. | |
| 7,615,225 B2 | 11/2009 | Forsberg et al. | |
| 7,816,388 B2 | 10/2010 | Carminati et al. | |
| 7,829,673 B2 | 11/2010 | De Weers et al. | |
| 8,088,896 B2 | 1/2012 | Tesar et al. | |
| 8,153,765 B2 | 4/2012 | Park et al. | |
| 8,518,405 B2 | 8/2013 | Mukherjee | |
| 8,648,176 B2 | 2/2014 | Davis Orcutt et al. | |
| 8,846,001 B2 | 9/2014 | Velikyan et al. | |
| 9,090,698 B2 | 7/2015 | Mukherjee | |
| 9,217,038 B2 | 12/2015 | Goletz et al. | |
| 9,492,566 B2 | 11/2016 | Goldenberg et al. | |
| 9,546,217 B2 | 1/2017 | Behrens et al. | |
| 9,603,954 B2 | 3/2017 | Simon et al. | |
| 9,606,123 B2 | 3/2017 | Slack-Davis et al. | |
| 9,828,635 B2 | 11/2017 | Vincent et al. | |
| 10,017,580 B2 | 7/2018 | Van Berkel et al. | |
| 10,195,517 B2 | 2/2019 | Fechser | |
| 10,314,910 B2 | 6/2019 | Nathan et al. | |
| 10,377,778 B2 * | 8/2019 | Larsen ............... | A61K 51/0497 |
| 10,420,851 B2 | 9/2019 | Dave et al. | |
| 10,494,441 B2 | 12/2019 | Vincent et al. | |
| 10,507,251 B2 | 12/2019 | Morinaka et al. | |
| 10,517,966 B2 | 12/2019 | Morinaka et al. | |
| 10,919,973 B2 | 2/2021 | Clausen et al. | |
| 11,116,846 B2 | 9/2021 | Goldenberg et al. | |
| 11,136,410 B2 | 10/2021 | Kufe et al. | |
| 11,161,911 B2 | 11/2021 | White | |
| 11,191,854 B2 | 12/2021 | Burak et al. | |
| 11,225,496 B2 | 1/2022 | Berkman et al. | |
| 11,344,638 B2 | 5/2022 | Taub | |
| 2004/0258614 A1 | 12/2004 | Line et al. | |
| 2009/0304710 A1 | 12/2009 | Park et al. | |
| 2010/0204117 A1 | 8/2010 | Bevec | |
| 2010/0297003 A1 | 11/2010 | De Santis et al. | |
| 2011/0165074 A1 | 7/2011 | Gruell et al. | |
| 2012/0213698 A1 | 8/2012 | Petersen et al. | |
| 2012/0321619 A1 | 12/2012 | Linden et al. | |
| 2013/0129636 A1 | 5/2013 | Kamaly et al. | |
| 2014/0314670 A1 | 10/2014 | D'Addona et al. | |
| 2015/0030618 A1 | 1/2015 | Lerchen et al. | |
| 2016/0228587 A1 | 8/2016 | Eder et al. | |
| 2016/0297890 A1 | 10/2016 | Agatsuma et al. | |
| 2017/0158775 A1 | 6/2017 | Linden et al. | |
| 2018/0031566 A1 | 2/2018 | Do Couto et al. | |
| 2020/0061216 A1 | 2/2020 | Mukherjee | |
| 2020/0069706 A1 | 3/2020 | Slusher et al. | |

(Continued)

FOREIGN PATENT DOCUMENTS

| | | |
|---|---|---|
| CN | 101991867 A | 3/2011 |
| CN | 102406949 A | 4/2012 |

(Continued)

OTHER PUBLICATIONS

Stenberg, J Label Compd Radiopharm, 2020, vol. 63, 129-143. (Year: 2020).*
Bendre et al., Evaluation of Met-Val-Lys as a renal brush border enzyme-cleavable linker to reduce kidney uptake of 68Ga-labeled DOTA-conjugated peptides and peptidomimetics, Molecules (2020), 25(17), 3854.
Suzuki et al., Copper-64-Labeled Antibody Fragments for Immuno-PET/Radioimmunotherapy with Low Renal Radioactivity Levels and Amplified Tumor-Kidney Ratios, ACS Omega (2021), 6(33), 21556-21562.

(Continued)

*Primary Examiner* — D Margaret M Seaman
(74) *Attorney, Agent, or Firm* — Dentons Cohen & Grigsby P.C.

(57) ABSTRACT

Provided are new bifunctional chelators for use in the manufacture of radiolabeled targeting agents for therapeutic or diagnostic use. Also provided are conjugates of the new bifunctional chelators with various cancer antigen targeting agents.

26 Claims, 15 Drawing Sheets
Specification includes a Sequence Listing.

(56) References Cited

U.S. PATENT DOCUMENTS

| | | | |
|---|---|---|---|
| 2020/0101160 A1 | 4/2020 | Nathan et al. | |
| 2020/0297877 A1* | 9/2020 | Larsen | A61K 51/0402 |
| 2020/0306391 A1 | 10/2020 | Ray et al. | |
| 2020/0339625 A1 | 10/2020 | Lin et al. | |
| 2021/0008232 A1 | 1/2021 | Chen et al. | |
| 2021/0025006 A1 | 1/2021 | Xue et al. | |
| 2021/0154338 A1 | 5/2021 | Bander | |
| 2021/0161911 A1 | 6/2021 | Armour | |
| 2021/0164985 A1 | 6/2021 | Do Couto et al. | |
| 2021/0171653 A1 | 6/2021 | Risse et al. | |
| 2021/0196844 A1 | 7/2021 | Bander | |
| 2021/0238292 A1 | 8/2021 | Holland et al. | |
| 2021/0238303 A1 | 8/2021 | Agatsuma et al. | |
| 2021/0309711 A1 | 10/2021 | Li et al. | |
| 2021/0369877 A1 | 12/2021 | Rosch et al. | |
| 2021/0393809 A1* | 12/2021 | Haberkorn | A61K 51/0402 |
| 2021/0395281 A1 | 12/2021 | Mahoney et al. | |
| 2022/0024904 A1 | 1/2022 | Zeglis et al. | |
| 2022/0062446 A1 | 3/2022 | Perrin et al. | |
| 2022/0064312 A1 | 3/2022 | Yoshikawa et al. | |
| 2022/0096653 A1 | 3/2022 | Akaiwa et al. | |
| 2022/0220085 A1 | 7/2022 | Vlahov et al. | |
| 2022/0403051 A1 | 12/2022 | Powell et al. | |
| 2023/0047529 A1 | 2/2023 | Imura | |
| 2023/0072421 A1 | 3/2023 | Bohnke et al. | |
| 2023/0081720 A1 | 3/2023 | Burger et al. | |
| 2023/0106083 A1 | 4/2023 | Murphy et al. | |
| 2023/0119066 A1 | 4/2023 | Lan et al. | |
| 2023/0190796 A1 | 6/2023 | Huss et al. | |
| 2023/0201383 A1 | 6/2023 | Kjaer et al. | |
| 2023/0250178 A1 | 8/2023 | Berndt et al. | |

FOREIGN PATENT DOCUMENTS

| | | |
|---|---|---|
| CN | 102600489 A | 7/2012 |
| CN | 102626522 A | 8/2012 |
| CN | 102671217 A | 9/2012 |
| CN | 103529210 A | 1/2014 |
| CN | 104353087 A | 2/2015 |
| CN | 104815336 A | 8/2015 |
| CN | 106075484 A | 11/2016 |
| CN | 107096044 A | 8/2017 |
| CN | 108148012 A | 6/2018 |
| CN | 109134602 A | 1/2019 |
| CN | 110251695 A | 9/2019 |
| CN | 110743017 A | 2/2020 |
| CN | 111228521 A | 6/2020 |
| CN | 112237638 A | 1/2021 |
| CN | 112457401 A | 3/2021 |
| CN | 112546247 A | 3/2021 |
| CN | 112962125 A | 6/2021 |
| CN | 113368264 A | 9/2021 |
| CN | 113730613 A | 12/2021 |
| CN | 113730614 A | 12/2021 |
| CN | 114099719 A | 3/2022 |
| CN | 114404618 A | 4/2022 |
| DE | 102012019714 A1 | 4/2014 |
| EP | 4186926 A1 | 5/2023 |
| EP | 4227315 A1 | 8/2023 |
| JP | 2008222804 A | 9/2008 |
| JP | 2009269855 A | 11/2009 |
| JP | 2016020316 A | 2/2016 |
| KR | 20140014579 A | 2/2014 |
| KR | 101743727 B1 | 6/2017 |
| WO | 2005065724 A1 | 7/2005 |
| WO | 2007044756 A2 | 4/2007 |
| WO | 2013106824 A1 | 7/2013 |
| WO | 2021175147 A1 | 9/2021 |
| WO | 2022040607 A1 | 2/2022 |
| WO | 2022072292 A1 | 4/2022 |
| WO | 2022072293 A2 | 4/2022 |
| WO | 2022087156 A1 | 4/2022 |
| WO | 2022235676 A1 | 11/2022 |

OTHER PUBLICATIONS

Uehara et al., A Gallium-67/68-Labeled Antibody Fragment for Immuno-SPECT/PET Shows Low Renal Radioactivity Without Loss of Tumor Uptake, Clinical Cancer Research (2018), 24(14), 3309-3316.

Zhang et al., Improving the Theranostic Potential of Exendin 4 by Reducing the Renal Radioactivity through Brush Border Membrane Enzyme-Mediated Degradation, Bioconjugate Chemistry (2019), 30(6), 1745-1753.

International Search Report and Written Opinion dated Dec. 14, 2023 for corresponding International Application No. PCT/US2023/068062.

Kang et al., Recent developments in chemical conjugation strategies targeting native amino acids in proteins and their applications in antibody-drug conjugates, Chem. Sci., 12, (2021): 13613-13647.

Sneddon, et al., "Emerging chelators for nuclear imaging." Current Opinion in Chemical Biology, 63 (2021): 152-162.

Yang et al., "Harnessing a-Emitting Radionuclides for Therapy: Radiolabeling Method Review", J Nucl Med, (2022) 63:5-13.

* cited by examiner

BIFUNCTIONAL CHELATORS AND CONJUGATES

CROSS-REFERENCE TO RELATED APPLICATIONS

This application is a continuation of International Application No. PCT/US2023/068062 filed on Jun. 7, 2023, entitled BIFUNCTIONAL CHELATORS AND CONJUGATES, which claims priority to and the benefit of U.S. Provisional Patent Application No. 63/349,883 filed on Jun. 7, 2022, entitled BIFUNCTIONAL CHELATORS, U.S. Provisional Patent Application No. 63/408,970 filed on Sep. 22, 2022, entitled BIFUNCTIONAL CHELATORS, and U.S. Provisional Patent Application No. 63/487,789 filed on Mar. 1, 2023, entitled BIFUNCTIONAL CHELATORS AND CONJUGATES, which are expressly incorporated herein by reference in their entireties.

SEQUENCE LISTING

The present disclosure contains a Sequence Listing which has been submitted electronically in XML format and is hereby incorporated by reference in its entirety. Said XML copy, created on Jun. 7, 2023, is named PT23-045PCT_SL_ST26.xml and is 184,148 bytes in size.

FIELD OF THE INVENTION

The present disclosure relates to the field of bifunctional chelators and linkers.

BACKGROUND

Bifunctional chelators are compounds that include a metal (or metalloid) chelating moiety and a reactive group that can mediate conjugation to a target molecule such as a protein. Dodecane tetraacetic acid (DOTA), IUPAC name 2,2',2'',2'''-(1,4,7,10-Tetraazacyclododecane-1,4,7,10-tetrayl)tetraacetic acid, is a macrocyclic compound capable of chelating radiometals such as $^{90}$Y, $^{225}$Ac, and $^{177}$Lu. Bifunctional DOTA chelators known in the art include, for example, S-2-(4-Isothiocyanatobenzyl)-1,4,7,10-tetraazacyclododecane tetraacetic acid (also known as p-SCN-Bn-DOTA) and 1,4,7,10-Tetraazacyclododecane-1,4,7,10-tetraacetic acid mono-N-hydroxysuccinimide ester (also known as DOTA-NHS-ester).

BRIEF SUMMARY

The present disclosure provides novel bifunctional chelator compounds of formula (A), or a metal complex thereof:

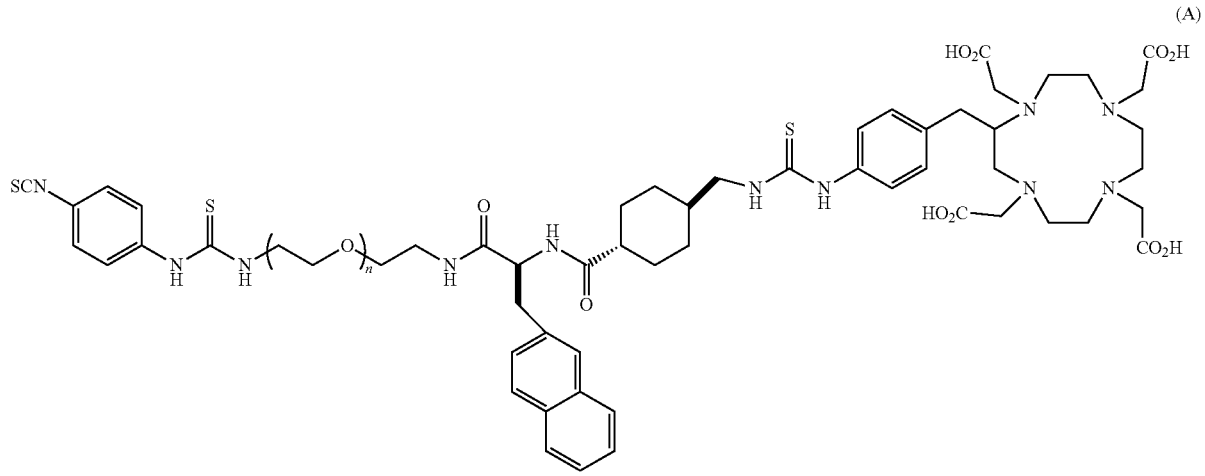

(A)

wherein n is 1 or an integer greater than 1, such as an integer from 1 to 1000 or any integer value therein or any subrange of integers therein, such as from 1 to 100 or 1 to 20. For example, n may be 1, 2, 3, 4, 5, 6, 7, 8, 9, or 10.

The present disclosure provides novel bifunctional chelator compounds of formula (B), or a metal complex thereof:

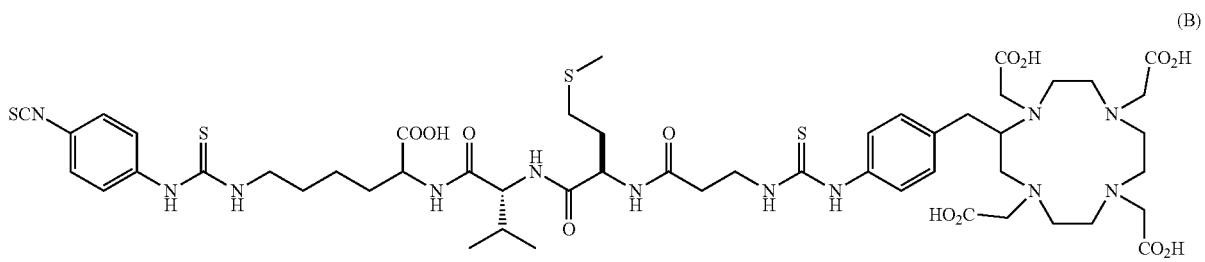

(B)

The present disclosure provides novel bifunctional chelator compounds having a formula including a metal chelator and at least one component selected from: a reactive group for conjugation of the bifunctional chelator to a target molecule such as a protein or a peptide, a benzyl group, at least one amino acid and/or amino acid derivative, a chelator moiety, a PEG spacer, a non-aromatic cyclic hydrocarbon, ethyleneamine, and thiourea, wherein when more than one component is included, the reactive group is a terminal component and any additional components may be in any order.

The present disclosure further provides novel bifunctional chelator compounds having a formula as shown in any one of FIGS. 3-17, i.e., compounds C-Q, or metal complexes thereof.

The present disclosure further provides a conjugated molecule formed by reacting one of the aforementioned bifunctional chelator compounds that includes a N-hydroxysuccinimide ester/NHS ester (abbreviated "NHS" herein) or thiocyanate (abbreviated "SCN" herein) reactive group and a molecule including one or more primary amine groups, including, but not limited to, a peptide, such as a synthetic peptide, or a protein, such as a recombinant protein.

The present disclosure provides a method for conjugating a chelator to a molecule including one or more primary amine groups, such as a protein or a peptide that includes the step of reacting the molecule with one of the aforementioned bifunctional chelator compounds that includes a NHS or SCN reactive group to form a chelator-conjugated molecule.

The present disclosure provides a conjugated molecule formed by reacting one of the aforementioned bifunctional chelator compounds that includes a phenyloxadiazolyl methylsulfone (abbreviated "PODS" herein) reactive group or derivative thereof and a molecule including one or more free thiol groups, including, but not limited to, a peptide, such as a synthetic peptide, or a protein, such as a recombinant protein.

Also provided by this disclosure is a method for conjugating a chelator to a molecule including one or more free thiol groups, such as a protein or a peptide, that includes the step of reacting the molecule with one of the aforementioned bifunctional chelator compounds that includes a PODS reactive group or derivative thereof to form a chelator-conjugated molecule. The method may include a prior or concurrent step of forming a free thiol group for reaction with a PODS reactive group by reducing a disulfide bond present in a molecule or connecting different molecules.

The molecules that are conjugated with the bifunctional chelator compounds may include antibodies such as monoclonal antibodies, or antibody chains, such as immunoglobulin heavy chains and/or immunoglobulin light chains, and/or the variable regions of such heavy or light chains. The molecules that are conjugated with the bifunctional chelator compounds may include antigen binding fragments of monoclonal antibodies such as Fab fragments or $Fab_2$ fragments, or corresponding scFv molecules.

Additional features, advantages, and aspects of the present disclosure may be set forth or apparent from consideration of the following detailed description, drawings if any, and claims. Moreover, it is to be understood that both the foregoing summary of the present disclosure and the following detailed description are exemplary and intended to provide further explanation without limiting the scope of the invention as claimed.

DETAILED DESCRIPTION

The present disclosure provides bifunctional chelator compounds. The bifunctional chelator compounds of the present disclosure may be used for the manufacture of radiolabeled targeting agents for therapeutic and/or diagnostic use. The present disclosure further provides methods of conjugation of the bifunctional chelator compounds to primary amines or thiols, such as amines or thiols of a peptide or protein, and compositions including the resulting conjugates, and methods for radiolabeling the resulting conjugates.

Figure 1:
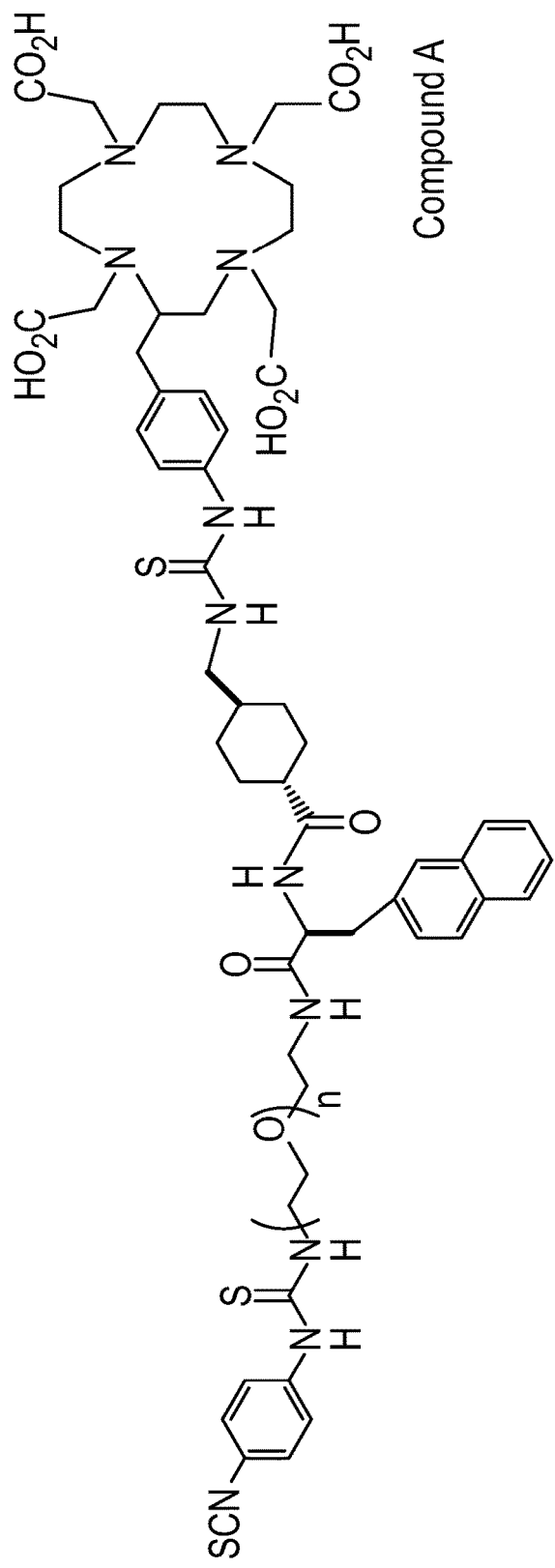
FIG. 1 shows a bifunctional chelator compound of Formula A.

The bifunctional chelator compounds of the present disclosure may include a compound having the formula (A) (FIG. 1), or a metal complex thereof:

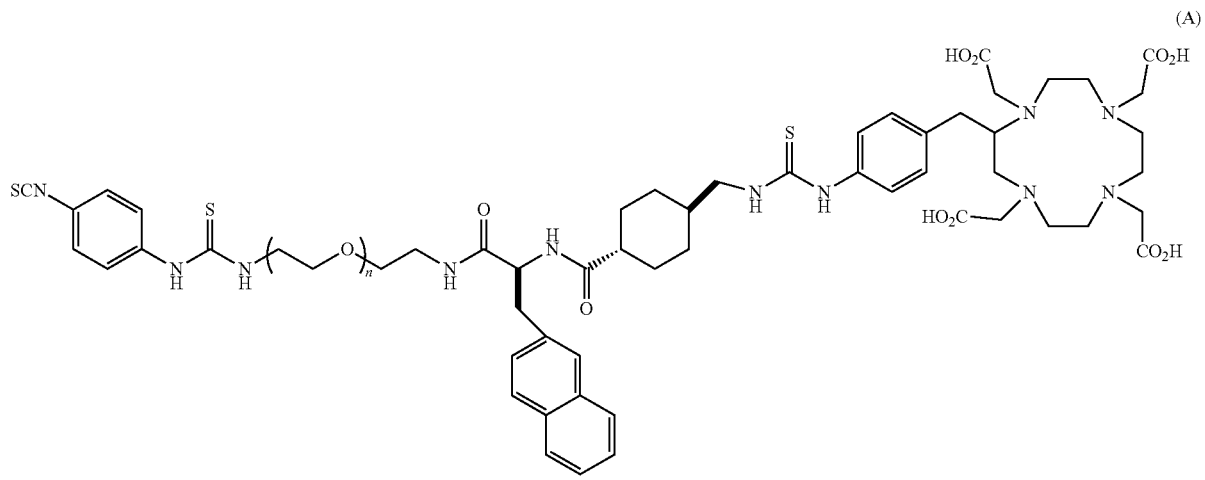

(A)

having a PEG$_n$ spacer, wherein n is 1 or an integer greater than 1, such as from 1 to 1000 or any integer value therein or any subrange of integers therein, such as from 1 to 100 or 1 to 20. The PEG$_n$ spacer may in addition or alternatively be defined by molecular weight or average molecular weight. For example, the average molecular weight of the PEG element may be 0.1 KD to 1 KD, 1 KD to 5 KD, 5 KD to 15 KD, 15 KD to 25 KD, 25 KD to 35 KD, or 35 KD to 50 KD.

Figure 2:
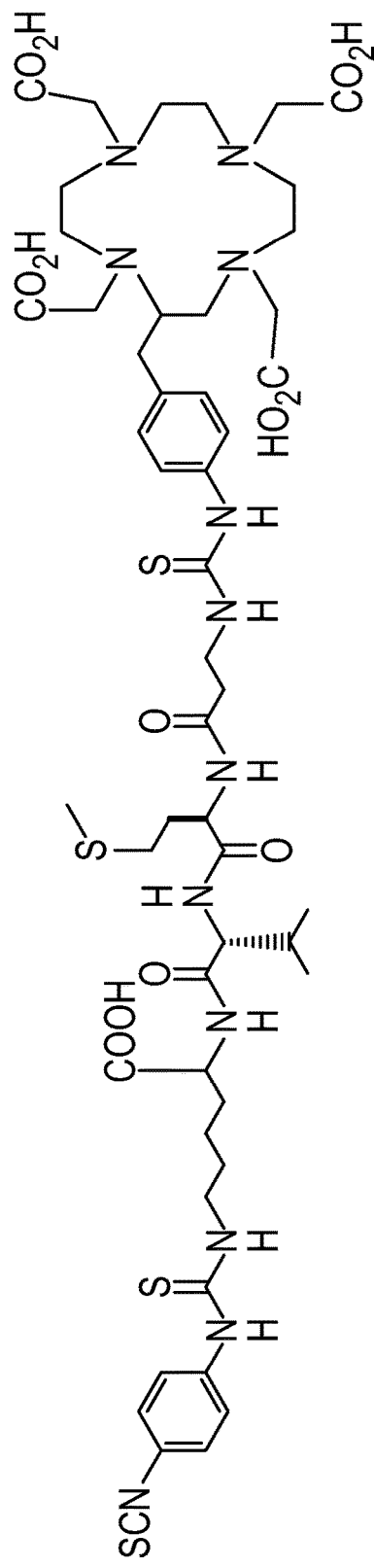
FIG. 2 shows a bifunctional chelator compound of Formula B.

The bifunctional chelator compounds of the present disclosure may include a compound having the formula (B) (FIG. 2), or a metal complex thereof:

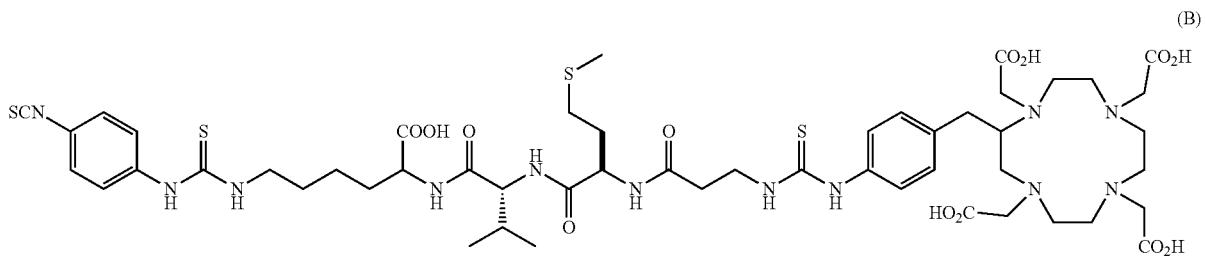

(B)

Figure 3:
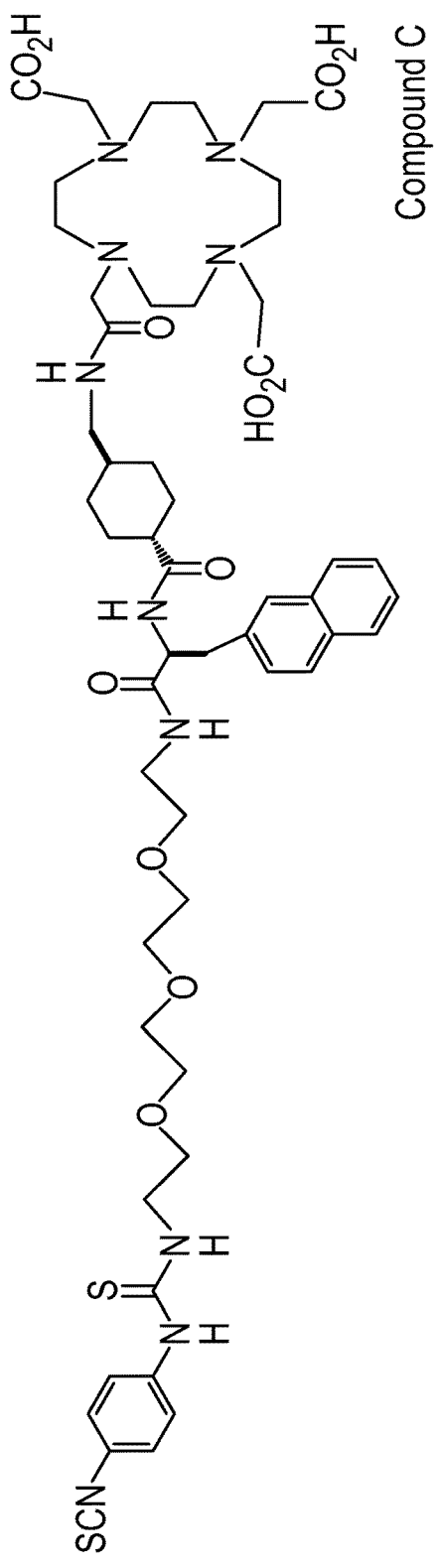
FIG. 3 shows a bifunctional chelator compound of Formula C.

The bifunctional chelator compounds of the present disclosure may include a compound having the formula (C) (FIG. 3), or a metal complex thereof:

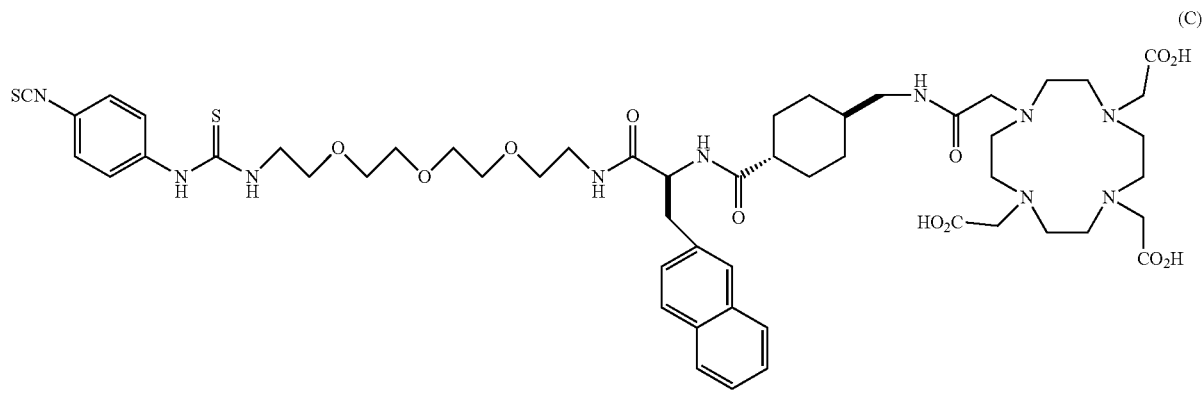

(C)

Figure 4:
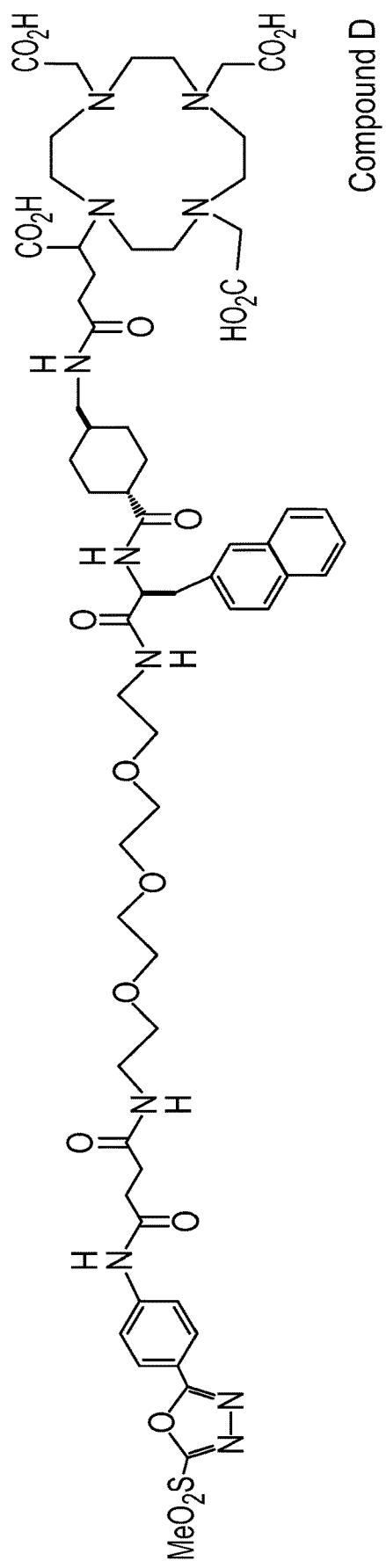
FIG. 4 shows a bifunctional chelator compound of Formula D.

The bifunctional chelator compounds of the present disclosure may include a compound having the formula (D) (FIG. 4), or a metal complex thereof:

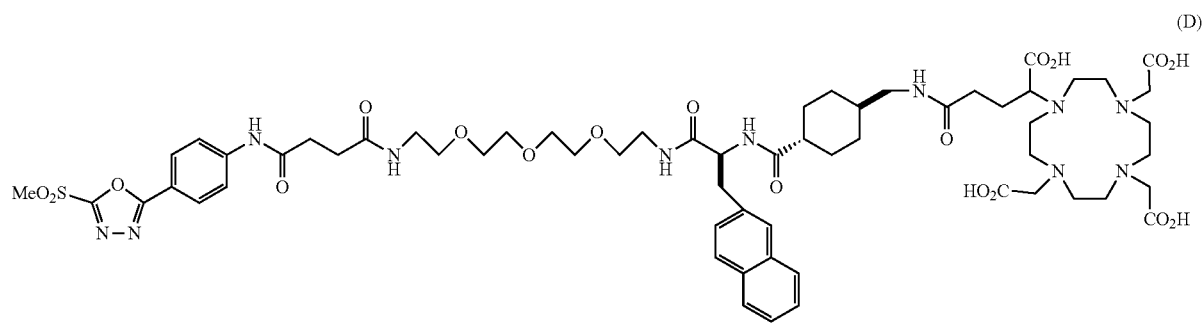 [SMILES: CS(=O)(=O)c1nnc(-c2ccc(NC(=O)CCC(=O)NCCOCCOCCOCCNC(=O)[C@H](Cc3ccc4ccccc4c3)NC(=O)[C@H]3CC[C@H](CNC(=O)CCC(C(=O)O)N4CCN(CC(=O)O)CCN(CC(=O)O)CCN(CC(=O)O)CC4)CC3)cc2)o1]

(D)

Figure 5:
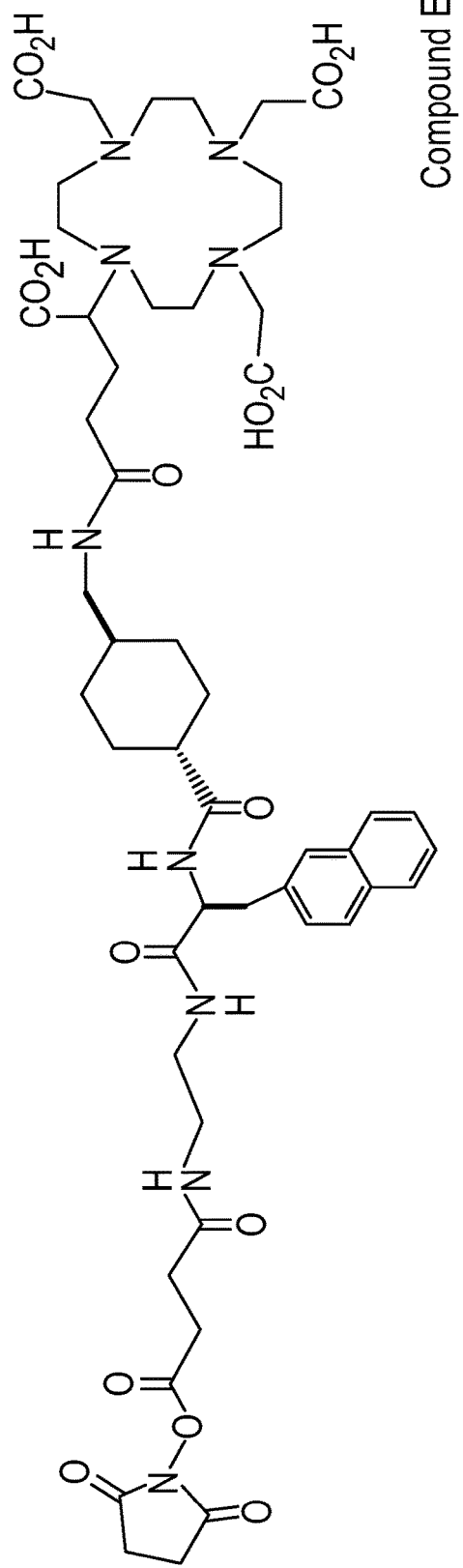
FIG. 5 shows a bifunctional chelator compound of Formula E.

The bifunctional chelator compounds of the present disclosure may include a compound having the formula (E) (FIG. 5), or a metal complex thereof:

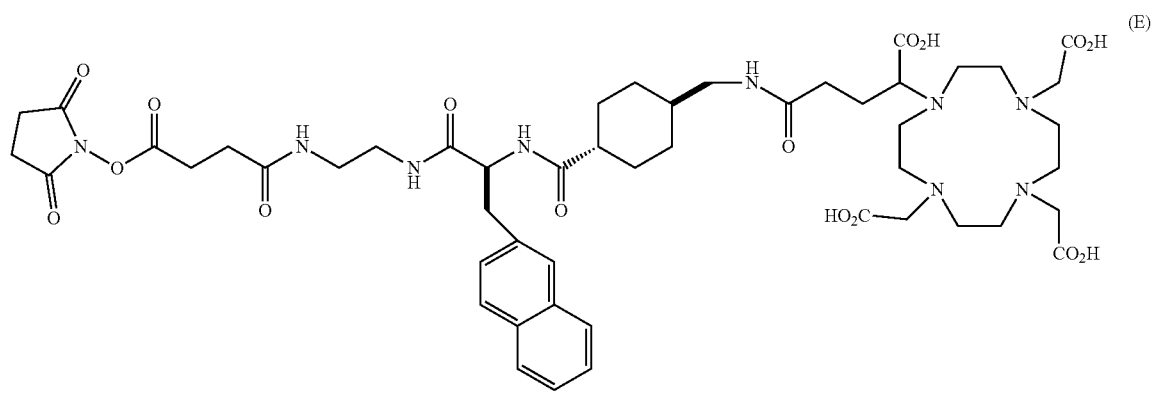 [SMILES: O=C(O)CN1CCN(CC(=O)O)CCN(C(CCC(=O)NC[C@H]2CC[C@H](C(=O)N[C@@H](Cc3ccc4ccccc4c3)C(=O)NCCNC(=O)CCC(=O)ON3C(=O)CCC3=O)CC2)C(=O)O)CCN(CC(=O)O)CC1]

(E)

Figure 6:
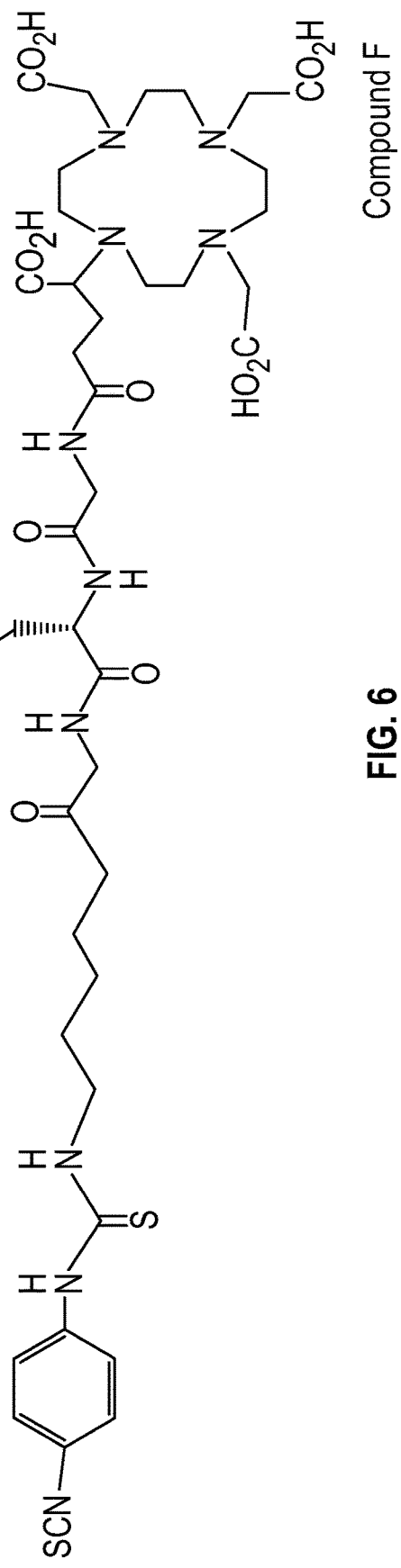
FIG. 6 shows a bifunctional chelator compound of Formula F.

The bifunctional chelator compounds of the present disclosure may include a compound having the formula (F) (FIG. 6), or a metal complex thereof:

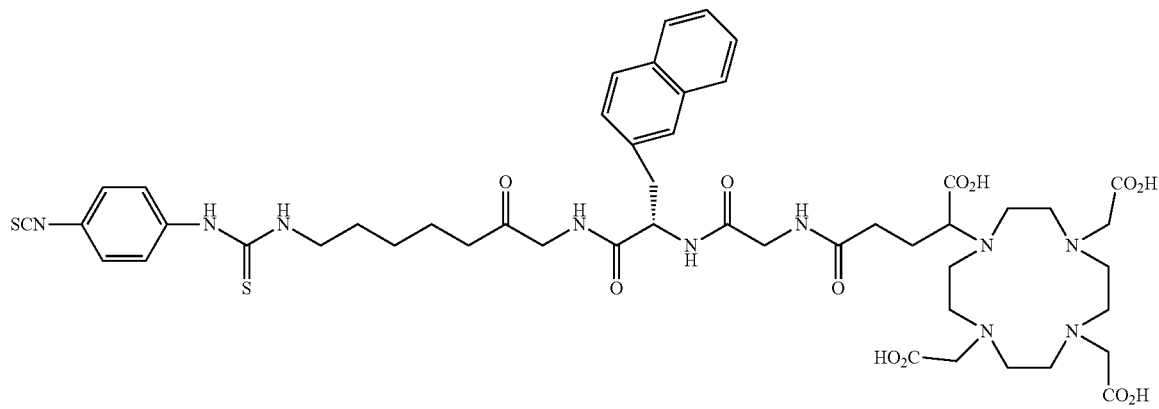

(F)

Figure 7:
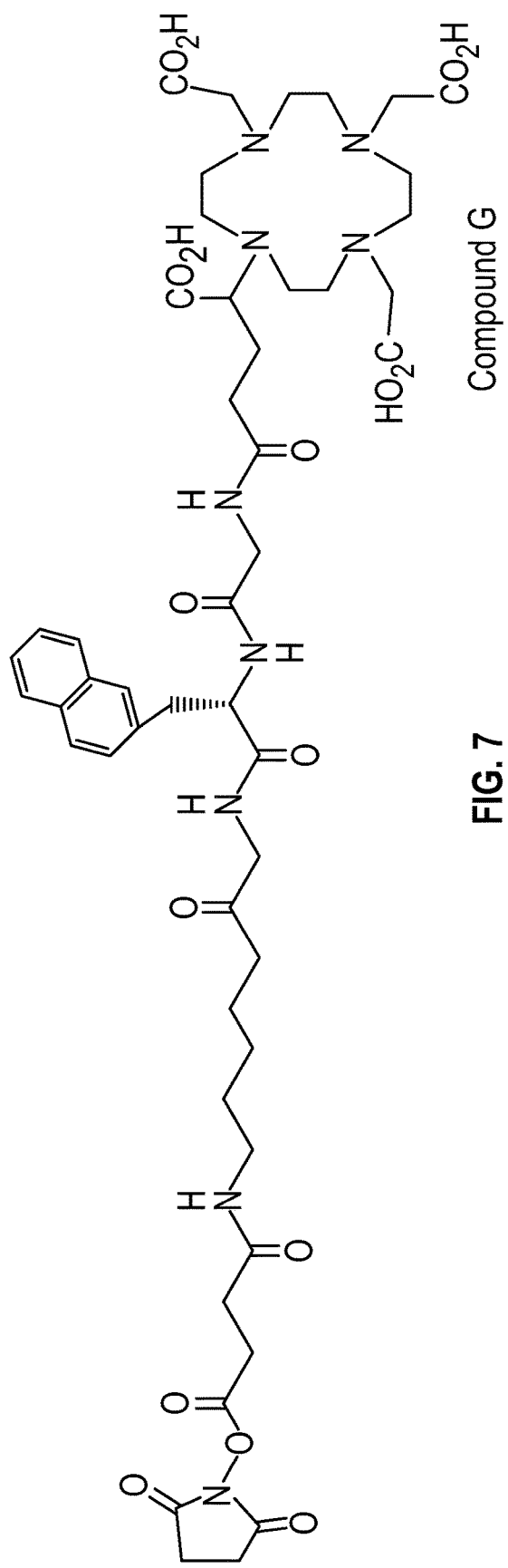
FIG. 7 shows a bifunctional chelator compound of Formula G.

The bifunctional chelator compounds of the present disclosure may include a compound having the formula (G) (FIG. 7), or a metal complex thereof:

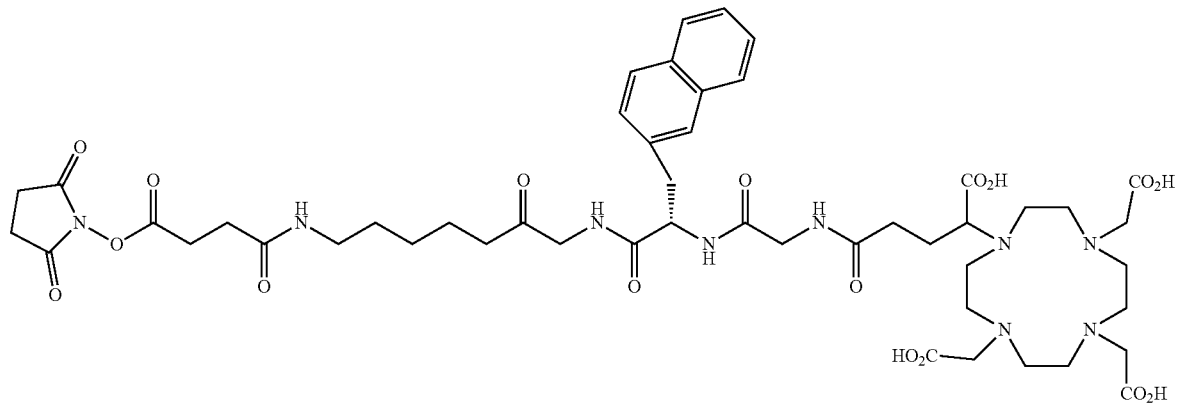

(G)

Figure 8:
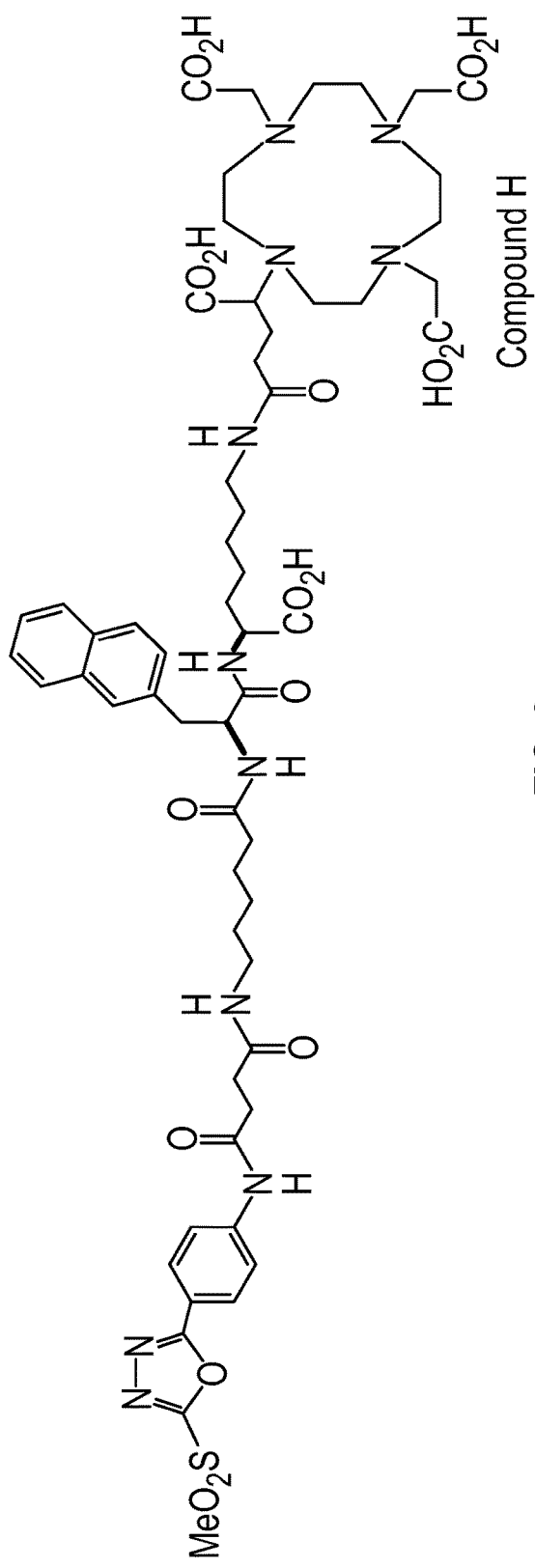
FIG. 8 shows a bifunctional chelator compound of Formula H.

The bifunctional chelator compounds of the present disclosure may include a compound having the formula (H) (FIG. 8), or a metal complex thereof:

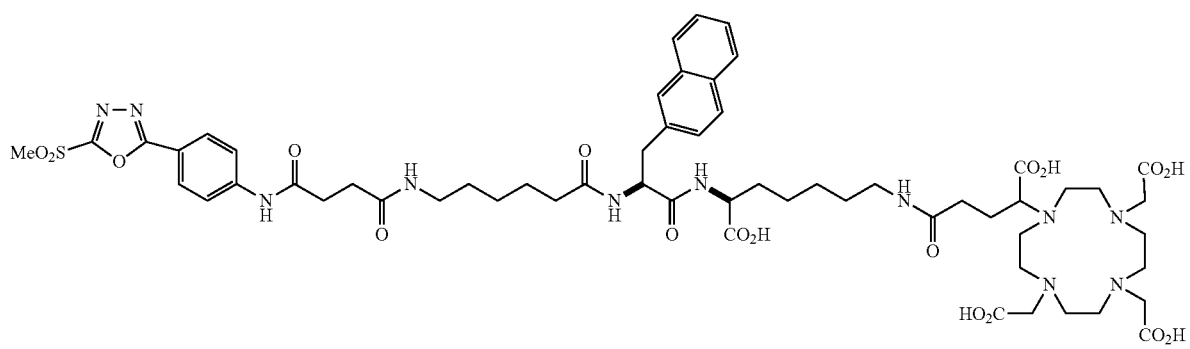

(H)

Figure 9:
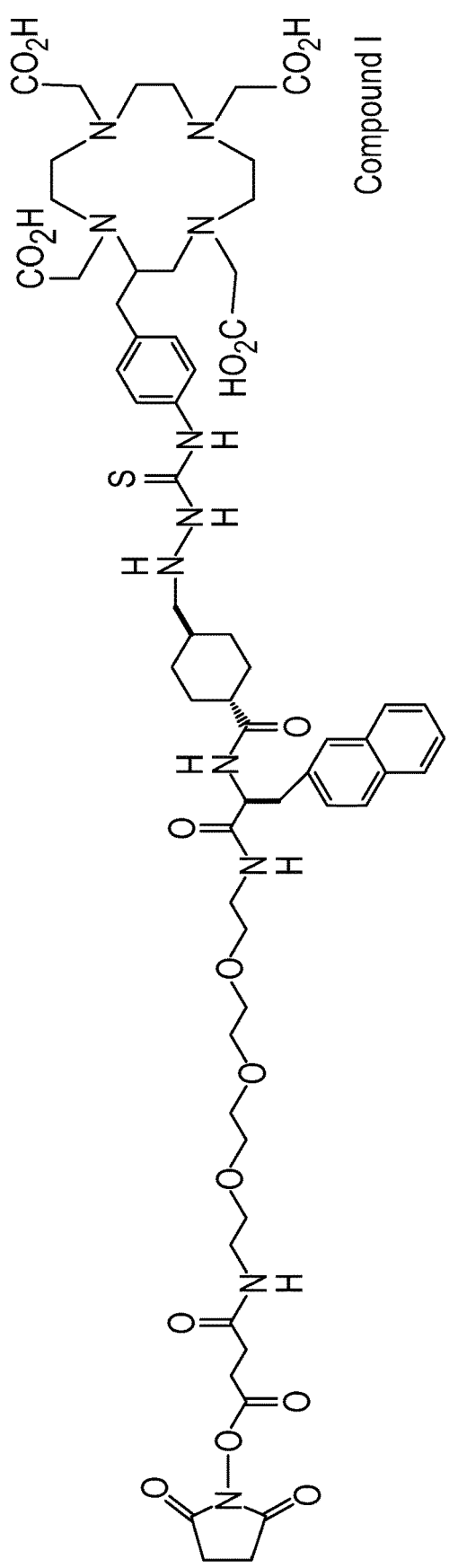
FIG. 9 shows a bifunctional chelator compound of Formula I.

The bifunctional chelator compounds of the present disclosure may include a compound having the formula (I) (FIG. 9), or a metal complex thereof:

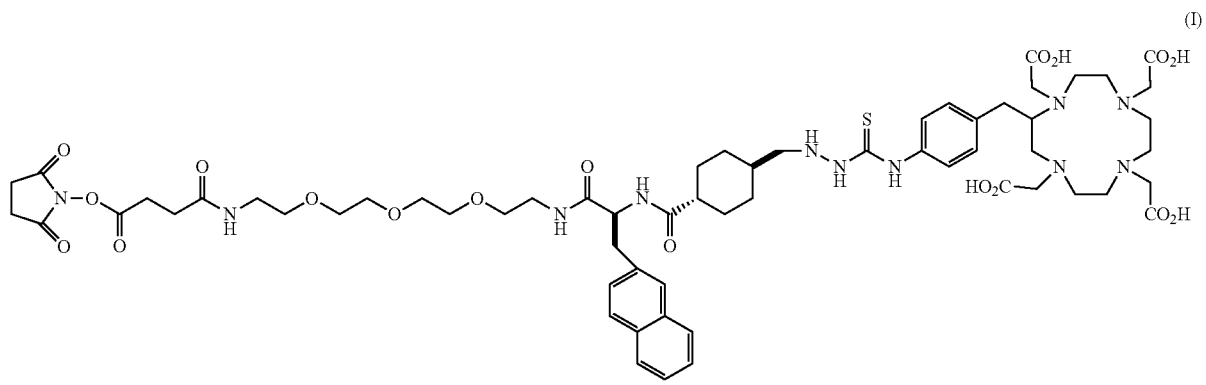 [SMILES: O=C(O)CN1CCN(CC(=O)O)CCN(CC(=O)O)C(Cc2ccc(NC(=S)NNC[C@H]3CC[C@H](C(=O)N[C@@H](Cc4ccc5ccccc5c4)C(=O)NCCOCCOCCOCCNC(=O)CCC(=O)ON4C(=O)CCC4=O)CC3)cc2)CN(CC(=O)O)CC1]

(I)

Figure 10:
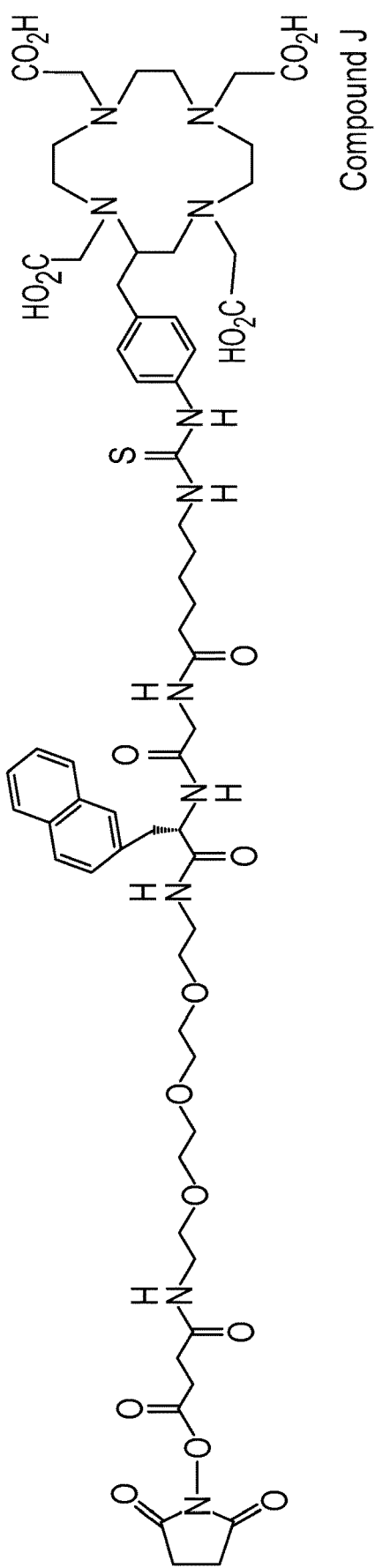
FIG. 10 shows a bifunctional chelator compound of Formula J.

The bifunctional chelator compounds of the present disclosure may include a compound having the formula (J) (FIG. 10), or a metal complex thereof:

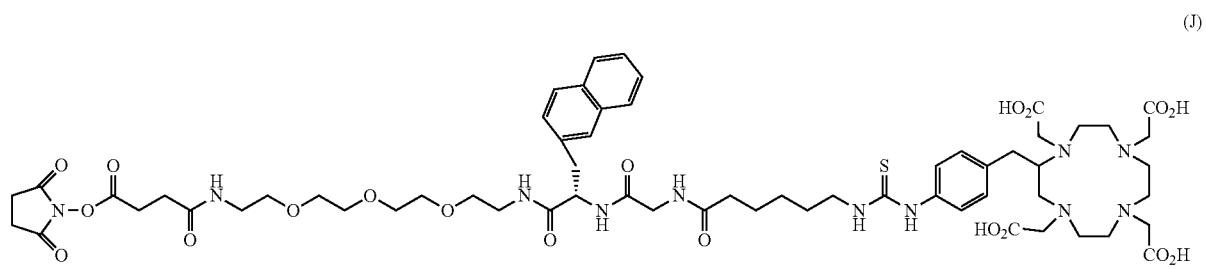 [SMILES: O=C(O)CN1CCN(CC(=O)O)CCN(CC(=O)O)C(Cc2ccc(NC(=S)NCCCCCC(=O)NCC(=O)N[C@@H](Cc3ccc4ccccc4c3)C(=O)NCCOCCOCCOCCNC(=O)CCC(=O)ON3C(=O)CCC3=O)cc2)CN(CC(=O)O)CC1]

(J)

Figure 11:
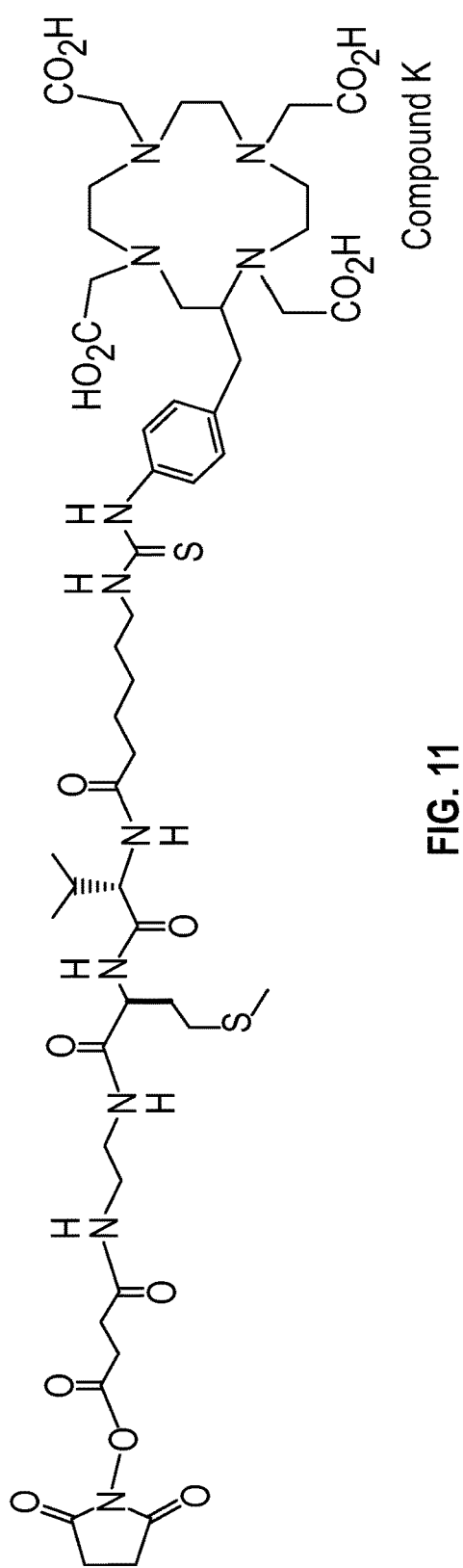
FIG. 11 shows a bifunctional chelator compound of Formula K.

The bifunctional chelator compounds of the present disclosure may include a compound having the formula (K) (FIG. 11), or a metal complex thereof:

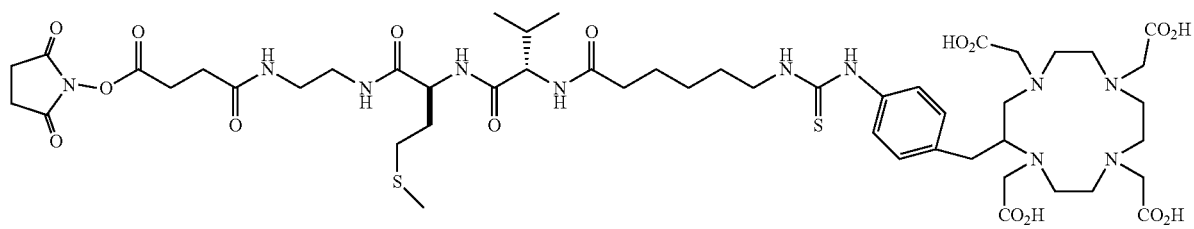

(K)

Figure 12:
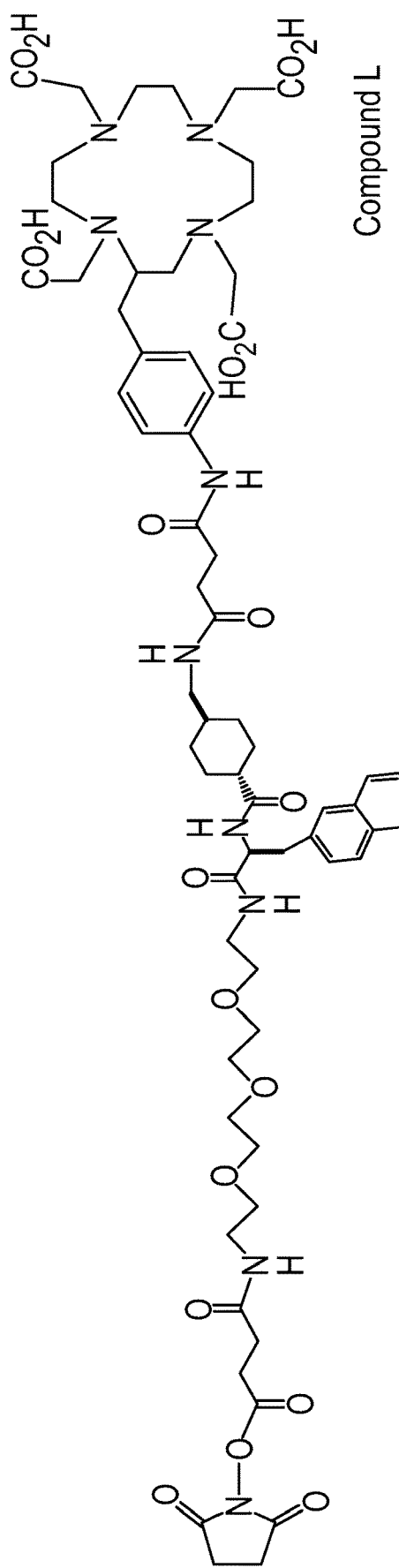
FIG. 12 shows a bifunctional chelator compound of Formula L.

The bifunctional chelator compounds of the present disclosure may include a compound having the formula (L) (FIG. 12), or a metal complex thereof:

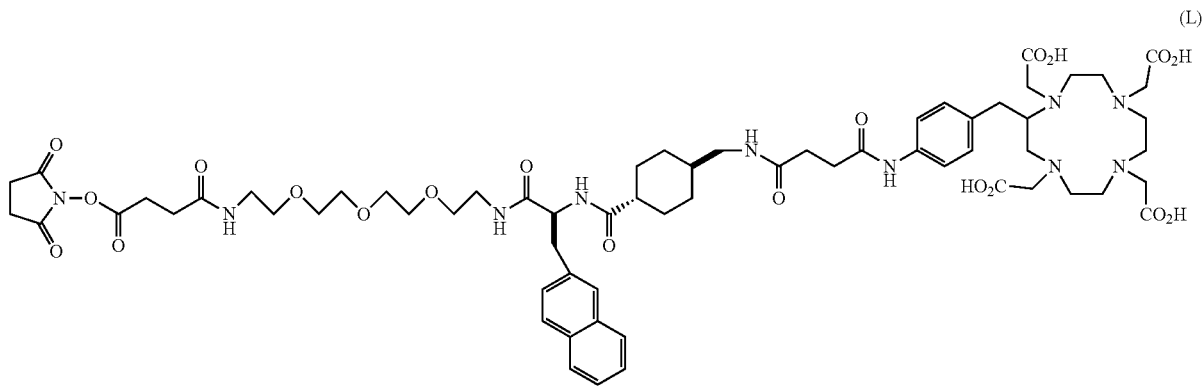 [SMILES: O=C(O)CN1CCN(CC(=O)O)CCN(CC(=O)O)C(Cc2ccc(NC(=O)CCC(=O)NC[C@H]3CC[C@H](C(=O)N[C@@H](Cc4ccc5ccccc5c4)C(=O)NCCOCCOCCOCCNC(=O)CCC(=O)ON4C(=O)CCC4=O)CC3)cc2)CN(CC(=O)O)CC1]

(L)

Figure 13:
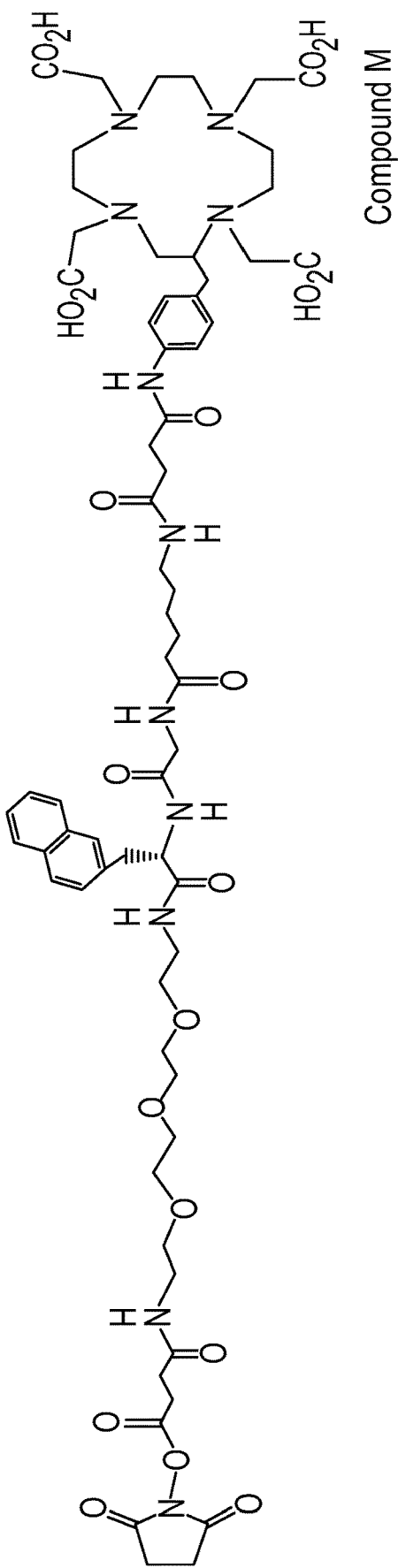
FIG. 13 shows a bifunctional chelator compound of Formula M.

The bifunctional chelator compounds of the present disclosure may include a compound having the formula (M) (FIG. 13), or a metal complex thereof:

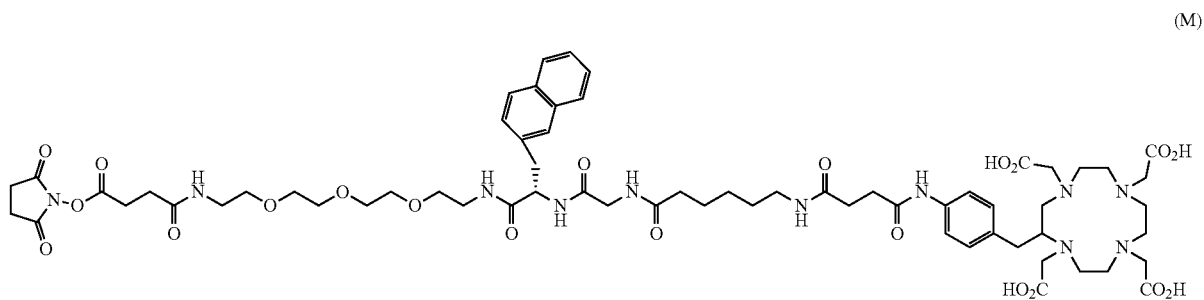 [SMILES: O=C(O)CN1CCN(CC(=O)O)CCN(CC(=O)O)C(Cc2ccc(NC(=O)CCC(=O)NCCCCCC(=O)NCC(=O)N[C@@H](Cc3ccc4ccccc4c3)C(=O)NCCOCCOCCOCCNC(=O)CCC(=O)ON3C(=O)CCC3=O)cc2)CN(CC(=O)O)CC1]

(M)

Figure 14:
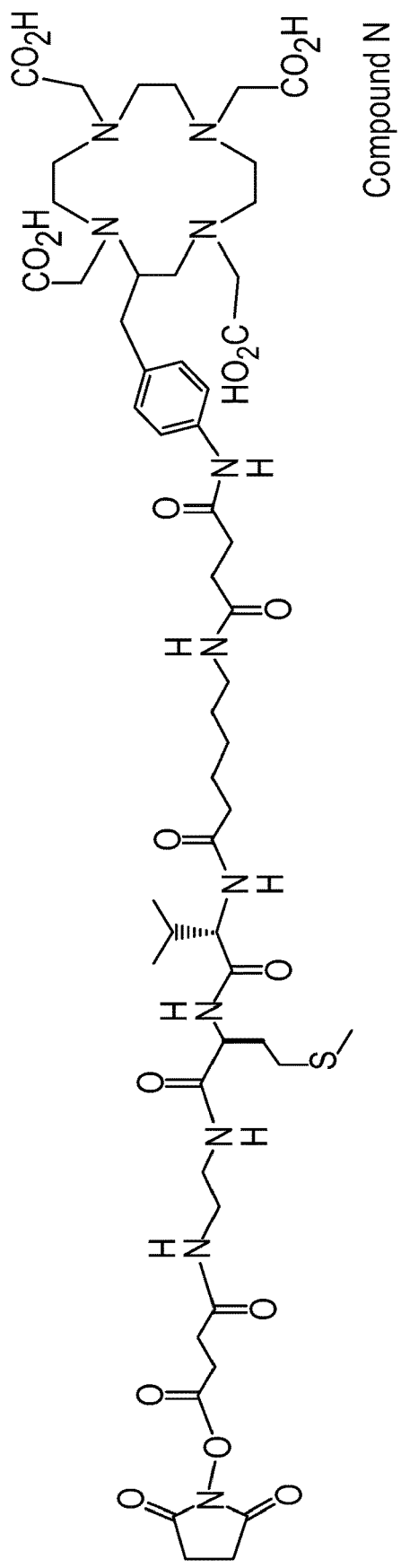
FIG. 14 shows a bifunctional chelator compound of Formula N.

The bifunctional chelator compounds of the present disclosure may include a compound having the formula (N) (FIG. 14), or a metal complex thereof:

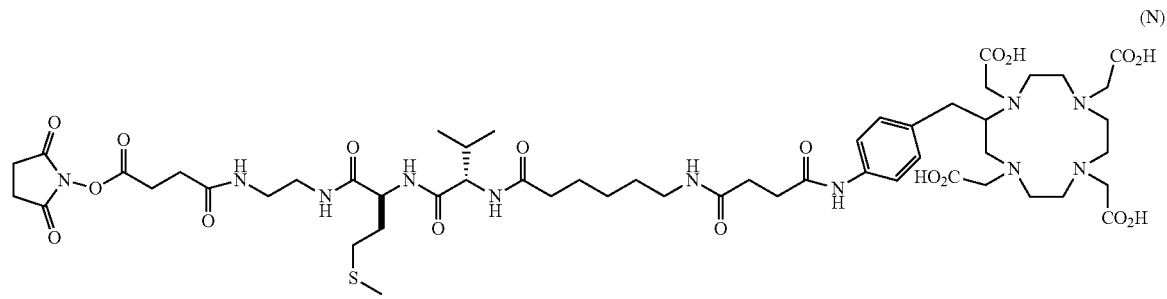 [SMILES: CSCC[C@H](NC(=O)[C@@H](NC(=O)CCCCCNC(=O)CCC(=O)Nc1ccc(CC2CN(CC(=O)O)CCN(CC(=O)O)CCN(CC(=O)O)CCN2CC(=O)O)cc1)C(C)C)C(=O)NCCNC(=O)CCC(=O)ON1C(=O)CCC1=O]

(N)

Figure 15:
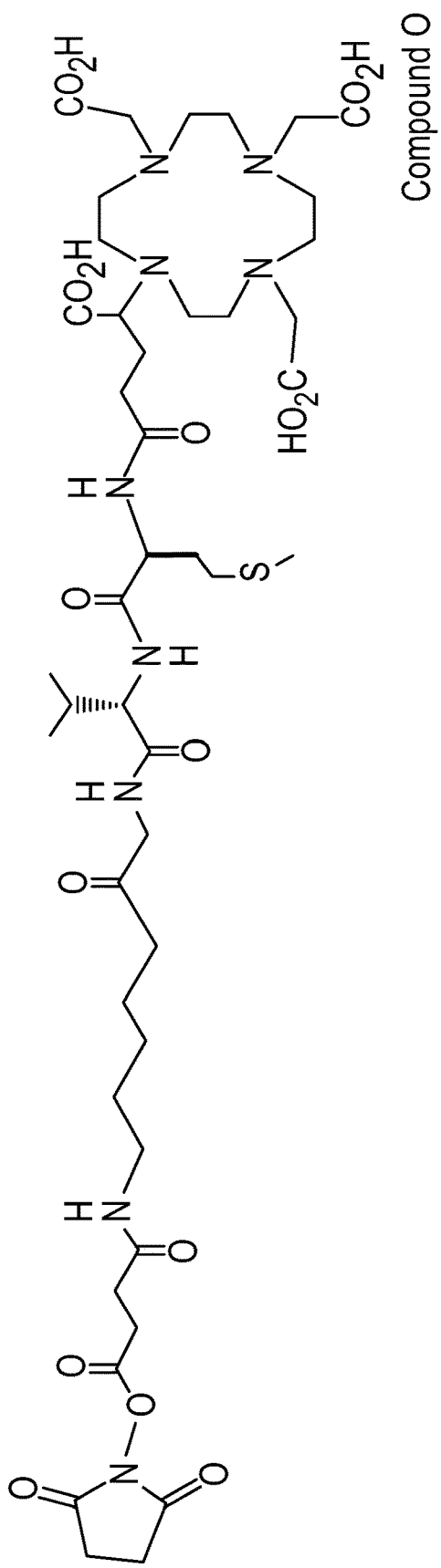
FIG. 15 shows a bifunctional chelator compound of Formula O.

The bifunctional chelator compounds of the present disclosure may include a compound having the formula (O) (FIG. 15), or a metal complex thereof:

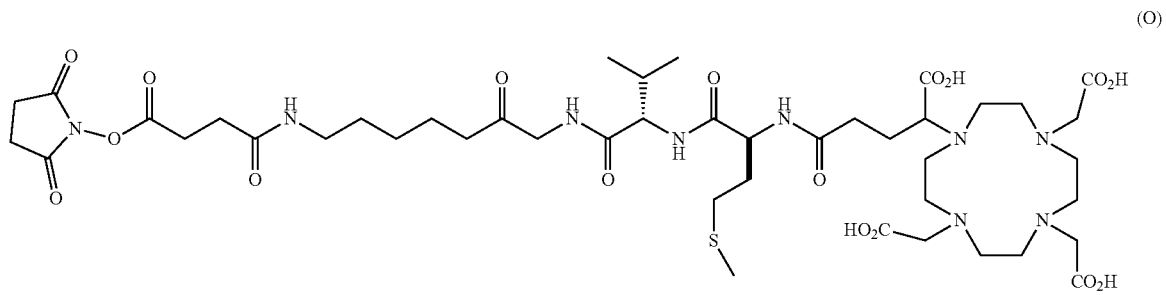 [SMILES: CSCC[C@H](NC(=O)CCC(C(=O)O)N1CCN(CC(=O)O)CCN(CC(=O)O)CCN(CC(=O)O)CC1)C(=O)N[C@H](C(=O)NCC(=O)CCCCCNC(=O)CCC(=O)ON1C(=O)CCC1=O)C(C)C]

(O)

Figure 16:
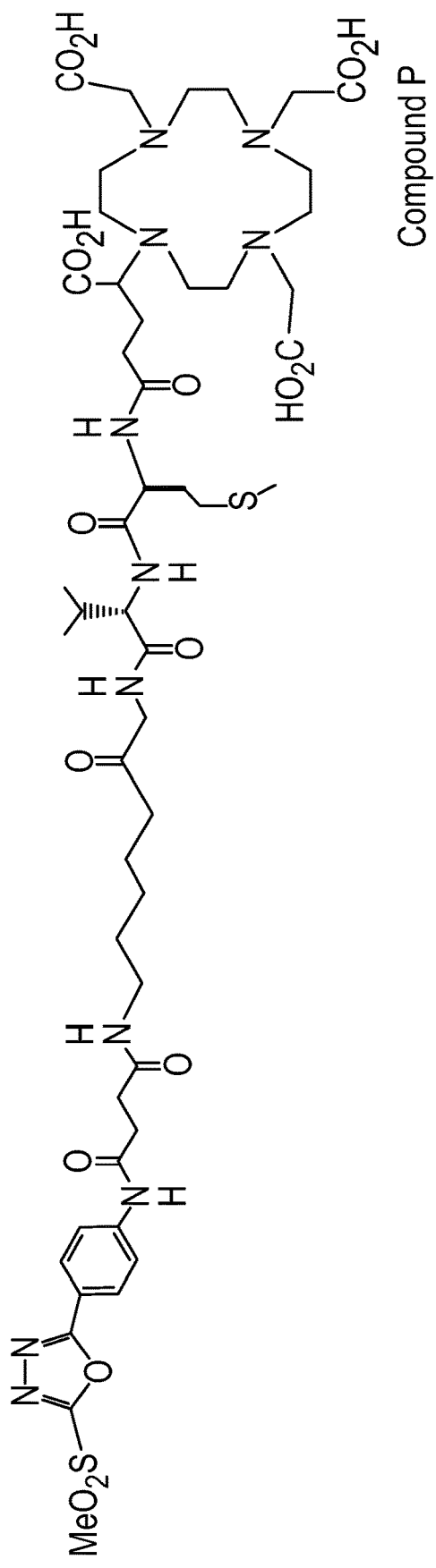
FIG. 16 shows a bifunctional chelator compound of Formula P.

The bifunctional chelator compounds of the present disclosure may include a compound having the formula (P) (FIG. 16), or a metal complex thereof:

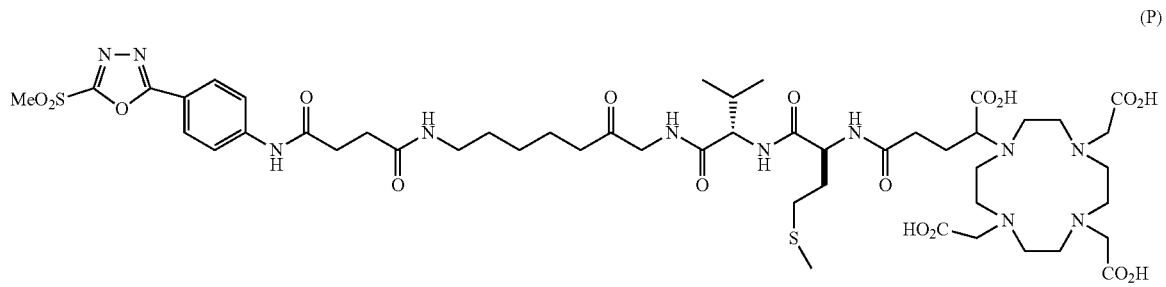 [SMILES: CSCC[C@H](NC(=O)CCC(C(=O)O)N1CCN(CC(=O)O)CCN(CC(=O)O)CCN(CC(=O)O)CC1)C(=O)N[C@H](C(=O)NCC(=O)CCCCCNC(=O)CCC(=O)Nc1ccc(-c2nnc(S(C)(=O)=O)o2)cc1)C(C)C]

(P)

Figure 17:
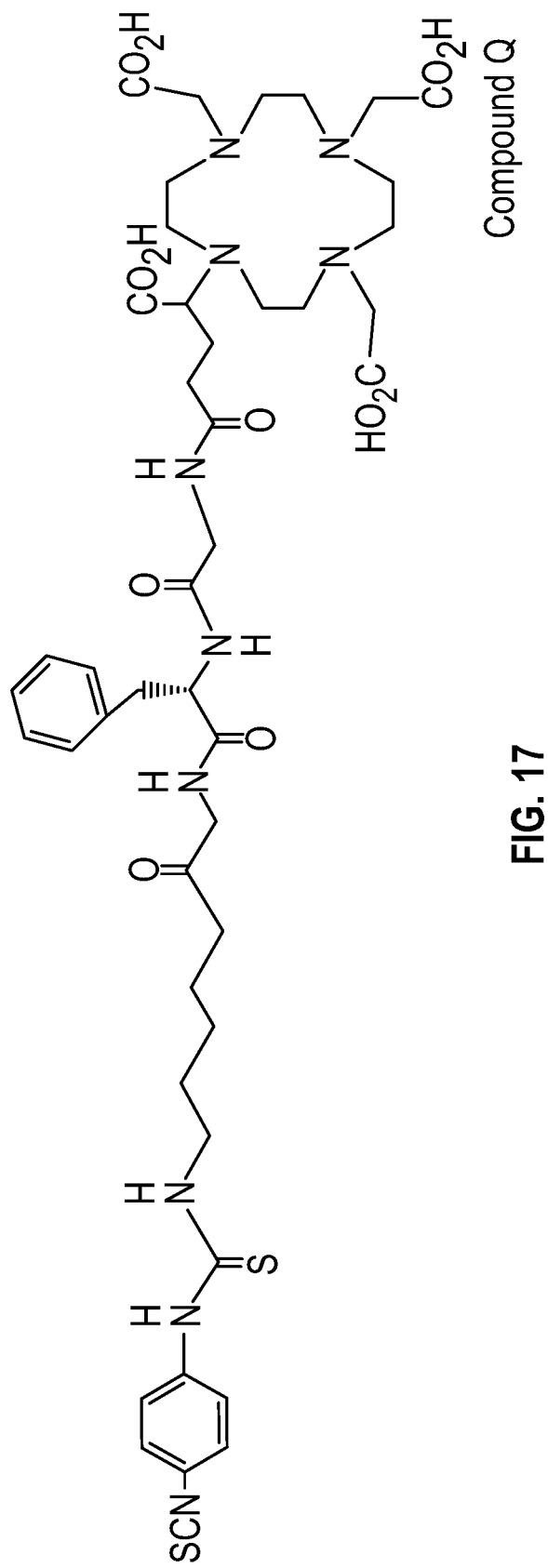
FIG. 17 shows a bifunctional chelator compound of Formula Q.

The bifunctional chelator compounds of the present disclosure may include a compound having the formula (Q) (FIG. 17), or a metal complex thereof:

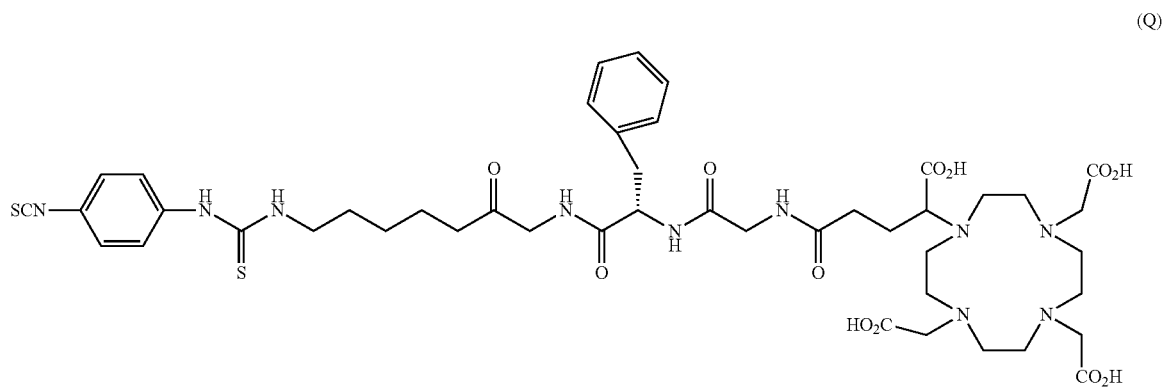

(Q)

The bifunctional chelator compounds of the present disclosure may include a compound having the formula (I), or a metal complex thereof:

M-L$_1$-R    (I)

wherein R is a reactive group, L$_1$ is a linker group, and M is a chelator moiety.

The reactive group R may include any suitable reactive group for conjugation of the bifunctional chelator to a target molecule, such as a protein or a peptide. A reactive group may include, but is not limited to, N-hydroxysuccinimide ester/NHS ester (herein "NETS"), thiocyanate (hereinafter "SCN"), a phenyloxadiazolyl methylsulfone (hereinafter "PODS"), and the like. The present disclosure also provides the corresponding ethylsulfone and propylsulfone analogs of the phenyloxadiazolyl methylsulfone (PODS) bifunctional chelator compounds. The NHS or SCN reactive groups may be used for conjugation to molecules having primary amine groups. The PODS reactive group may be used for conjugation to molecules having free thiols. The present disclosure also provides corresponding bifunctional chelator compounds having, instead, a 4-pyridyl reactive group for conjugation to molecules including primary amine groups, such as via the Zincke reaction.

The chelator moiety M may include DOTA, DOTA-GA, DOTA derivative chelator moieties, or any of the chelator moieties disclosed herein.

The linker group $L_1$ may include at least one component selected from: a benzyl group, at least one amino acid and/or amino acid derivative, a PEG spacer, a non-aromatic cyclic hydrocarbon, a linear hydrocarbon, ethyleneamine, thiourea, and the like, wherein when more than one component is included, the reactive group is a terminal component and any additional components may be in any order.

$L_1$ may include the formula (IA):

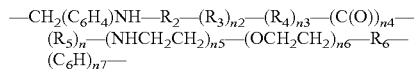

wherein n2-n7 is 0 or 1; $R_2$ is —C(S)—, —C(S)NH—, —C(O)CH$_2$CH$_2$—, C(O)CH$_2$CH$_2$C(O)—; $R_3$ is CH$_2$, NHCH$_2$, or (CH$_2$)$_{n1}$, where n1 is 1 to 5; $R_4$ is a cyclic alkane having 5 to 8 carbons or linear alkane having 1 to 6 carbons; $R_5$ is an amino acid or amino acid derivative, wherein n is 1, 2, or 3; and $R_6$ is —NHC(S)NH—, —C(S)NH—, —C(O)NH—, NH(CH$_2$)$_2$NHC(O)(CH$_2$)$_2$, or NHC(O)(CH$_2$)$_2$—.

For Compound A, $L_1$ may include:

—CH$_2$(C$_6$H$_4$)NH—C(S)NH—CH$_2$—(C$_6$H$_6$)—C(O)—R$_5$—NHCH$_2$CH$_2$—(OCH$_2$CH$_2$)$_n$—NHC(S)NH—C$_6$H$_4$— wherein $R_5$ is naphthylalanine.

For Compound B, $L_1$ may include:

—CH$_2$(C$_6$H$_4$)NH—C(S)NH—CH$_2$—CH$_2$—C(O)—(R$_5$)$_3$—C(S)NH—(C$_6$H$_4$)$_n$— wherein $R_5$ is -methionine-valine-lysine-.

For Compound I, $L_1$ may include:

—CH$_2$(C$_6$H$_4$)NH—C(S)NH—NHCH$_2$—(C$_6$H$_6$)—C(O)—R$_5$—NHCH$_2$CH$_2$—(OCH$_2$CH$_2$)$_3$—NHC(O)CH$_2$CH$_2$— wherein $R_5$ is naphthylalanine.

For Compound J, $L_1$ may include:

—CH$_2$(C$_6$H$_4$)NH—C(S)—(R$_5$)$_3$—NHCH$_2$CH$_2$—(OCH$_2$CH$_2$)$_3$—NHC(O)CH$_2$CH$_2$— wherein $R_5$ is -naphthylalanine-glycyl-lysine-.

For Compound K, $L_1$ may include:

—CH$_2$(C$_6$H$_4$)NH—C(S)—(R$_5$)$_3$—NHCH$_2$CH$_2$—NHC(O)CH$_2$CH$_2$— wherein $R_5$ is -methionine-valine-lysine-.

For Compound L, $L_1$ may include:

—CH$_2$(C$_6$H$_4$)NH—C(O)CH$_2$CH$_2$C(O)—NHCH$_2$—(C$_6$H$_6$)—C(O)—R$_5$—NHCH$_2$CH$_2$—(OCH$_2$CH$_2$)$_3$—NHC(O)CH$_2$CH$_2$— wherein $R_5$ is naphthylalanine.

For Compound M, $L_1$ may include:

—CH$_2$(C$_6$H$_4$)NH—C(O)CH$_2$CH$_2$—C(O)—(R$_5$)$_3$—(OCH$_2$CH$_2$)$_3$—NHC(O)CH$_2$CH$_2$— wherein $R_5$ is naphthylalanine-glycyl-lysine.

For Compound N, $L_1$ may include:

—CH$_2$(C$_6$H$_4$)NH—C(O)CH$_2$CH$_2$—C(O)—(R$_5$)$_3$—NHCH$_2$CH$_2$—NHC(O)CH$_2$CH$_2$— wherein $R_5$ is -methionine-valine-lysine-.

The bifunctional chelator compounds of the present disclosure may include a compound having the formula (II), or a metal complex thereof:

$$M\text{-}L_2\text{-}R \qquad (II)$$

wherein R is a reactive group according to the present disclosure, $L_2$ is a linker group of the present disclosure, and M is a chelator moiety of the present disclosure.

The linker group $L_2$ may include the formula (IIA):

—R$_1$—(R$_2$)$_{n1}$—(C(O))$_{n2}$—(R$_3$)$_n$—(NHCH$_2$CH$_2$)$_{n3}$—(OCH$_2$CH$_2$)$_{n4}$—R$_5$—(C$_6$H$_4$)$_{n4}$— (IIA)

wherein: n1-n5 is 0 or 1; $R_1$ is —CH$_2$C(O)NHCH$_2$—, —C(CO$_2$H)CH$_2$CH$_2$C(O)NHCH$_2$—, —C(CO$_2$H)CH$_2$CH$_2$C(O)—, or —C(CO$_2$H)CH$_2$CH$_2$; $R_2$ is a cyclic alkane having 5 to 8 carbons or linear alkane having 1 to 6 carbons; $R_3$ is an amino acid or amino acid derivative; n is 1, 2, or 3; and $R_4$ is —NHC(S)NH—, —C(S)NH—, —NHC(O)CH$_2$CH$_2$C(O)NH—, —NHC(O)CH$_2$CH$_2$C(O)—, —NHC(O)CH$_2$CH$_2$—, —C(O)CH$_2$CH$_2$C(O)NH—, or —C(O)CH$_2$CH$_2$C(O)—.

For Compound C, $L_2$ may include:

—CH$_2$C(O)NHCH$_2$—(C$_6$H$_6$)—C(O)—R$_3$—NHCH$_2$CH$_2$—(OCH$_2$CH$_2$)$_3$—NHC(S)NH—(C$_6$H$_4$)— wherein $R_3$ is naphthylalanine.

For Compound D, $L_2$ may include:

—C(CO$_2$H)CH$_2$CH$_2$C(O)NHCH$_2$—(C$_6$H$_6$)—C(O)—R$_3$—NHCH$_2$CH$_2$—(OCH$_2$CH$_2$)$_3$—NHC(O)CH$_2$CH$_2$C(O)NH—(C$_6$H$_4$)— wherein $R_3$ is naphthylalanine.

For Compound E, $L_2$ may include:

—C(CO$_2$H)CH$_2$CH$_2$C(O)NHCH$_2$—(C$_6$H$_6$)—C(O)—R$_3$—NHCH$_2$CH$_2$—(OCH$_2$CH$_2$)$_3$—NHC(O)CH$_2$CH$_2$C(O)— wherein $R_3$ is naphthylalanine.

For Compound F, $L_2$ may include:

—C(CO$_2$H)CH$_2$CH$_2$—C(O)—R$_3$—C(S)NH—(C$_6$H$_4$)— wherein $R_3$ is naphthylalanine-lysine.

For Compound G, $L_2$ may include:

—C(CO$_2$H)CH$_2$CH$_2$C(O)NHCH$_2$—C(O)—R$_3$—C(O)CH$_2$CH$_2$C(O)— wherein $R_3$ is naphthylalanine-lysine.

For Compound H, $L_2$ may include:

—C(CO$_2$H)CH$_2$CH$_2$—C(O)—R$_3$—C(O)CH$_2$CH$_2$C(O)NH—(C$_6$H$_4$)— wherein $R_3$ is lysine-naphthylalanine-lysine.

For Compound O, $L_2$ may include:

—C(CO$_2$H)CH$_2$CH$_2$—C(O)—R$_3$—C(O)CH$_2$CH$_2$C(O)— wherein $R_3$ is methionine-valine-lysine.

For Compound P, $L_2$ may include:

—C(CO$_2$H)CH$_2$CH$_2$—C(O)—R$_3$—C(O)CH$_2$CH$_2$C(O)NH—(C$_6$H$_4$)— wherein $R_3$ is methionine-valine-lysine.

For Compound Q, $L_2$ may include:

—C(CO$_2$H)CH$_2$CH$_2$—C(O)—R$_3$—C(S)NH—(C$_6$H$_4$)— wherein $R_3$ is glycyl-phenyalanyl-lysine.

The bifunctional chelator compounds of the present disclosure may include a compound having the formula (III), or a metal complex thereof:

$$M_1\text{-}L_a\text{-}R \qquad \text{(III)}$$

wherein R is a reactive group according to the present disclosure, $L_a$ is a linker group of the present disclosure, and $M_1$ is a chelator moiety of the present disclosure.

A chelator moiety $M_1$ may include, but is not limited to, a chelator moiety having the formula (IIIA), (IIIB), or (IIIC):

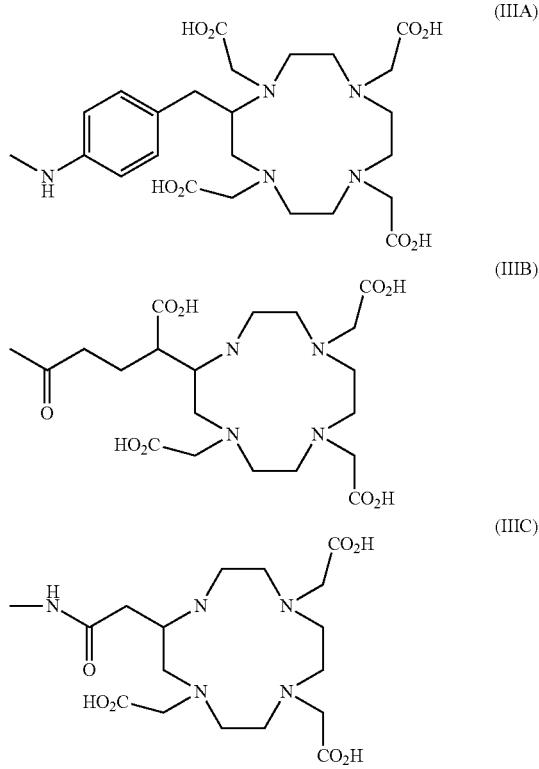

(IIIA)

(IIIB)

(IIIC)

wherein IIIA is S-2-(4-aminobenzyl)-1,4,7,10-tetraazacyclododecane tetraacetic acid (i.e., p-NH$_2$-Bn-DOTA); IIIB is (R)-5-(tert-butoxy)-5-oxo-4-(4,7,10-tris(2-(tert-butoxy)-2-oxoethyl)-1,4,7,10-tetraazacyclododecan-1-yl)pentanoic acid (i.e., (R)-DOTA-GA(tBu)$_4$); and IIIC is 5-(tert-butoxy)-5-oxo-4-(4,7,10-tris(2-(tert-butoxy)-2-oxoethyl)-1,4,7,10-tetraazacyclododecan-1-yl)-methylamine.

A reactive group R may include, but is not limited to, a reactive group having the formula (IIID), (IIIE), or (IIIF):

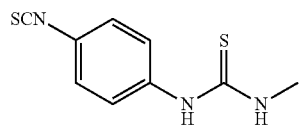

(IIID)

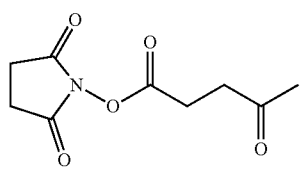

(IIIE)

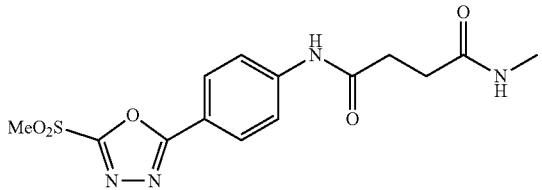

(IIIF)

The linker group $L_a$ may include the formula (IIIG):

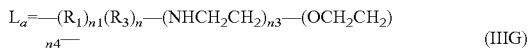

$$L_a = -(R_1)_{n1}(R_3)_n-(NHCH_2CH_2)_{n3}-(OCH_2CH_2)_{n4}- \qquad \text{(IIIG)}$$

wherein: n1-n4 is 0 or 1; $R_1$ is —C(S)NHCH$_2$—(R$_2$)$_{n2}$—C(O),
—C(S)NHNHCH$_2$—(R$_2$)$_{n2}$—C(O), —NHCH$_2$—(R$_2$)$_{n2}$—C(O),
—C(S)NH, —C(O)CH$_2$CH$_2$C(O)NH(R$_2$)C(O)—, —C(O)CH$_2$CH$_2$C(O)NHCH$_2$(R$_2$)C(O)—,
—R$_2$C(O), or —C(O)CH$_2$CH$_2$C(O)NH—, wherein R$_2$ is a cyclohexane or CH$_2$; R$_3$ is an amino acid or amino acid derivative; and n is 1, 2, or 3.

Exemplary linker groups $L_a$ include:
—C(S)NHCH$_2$(C$_6$H$_6$)C(O)—R$_3$—(NHCH$_2$CH$_2$)—(OCH$_2$CH$_2$)$_3$—, wherein R$_3$ is naphthylalanine;
—C(S)NHCH$_2$(CH$_2$)C(O)—R$_3$—, wherein R$_3$ is -methionine-valine-lysine-;
—(C$_6$H$_6$)C(O)—R$_3$—(NHCH$_2$CH$_2$)—(OCH$_2$CH$_2$)$_3$—, wherein R$_3$ is naphthylalanine;
—NHCH$_2$—(C$_6$H$_6$)—C(O)—R$_3$—(NHCH$_2$CH$_2$)—(OCH$_2$CH$_2$)$_3$—, wherein R$_3$ is naphthylalanine;
—NHCH$_2$—(C$_6$H$_6$)—C(O)—R$_3$—(NHCH$_2$CH$_2$)—, wherein R$_3$ is naphthylalanine;
—NHCH$_2$—C(O)—R$_3$—, wherein R$_3$ is naphthylalanine-lysine or glycyl-phenylalanyl-lysine;
—R$_3$—, wherein R$_3$ is lysine-naphthylalanine-lysine or methionine-valine-lysine or glycyl-phenylalanyl-lysine;
—C(S)NHNHCH$_2$(C$_6$H$_6$)C(O)—R$_3$—(NHCH$_2$CH$_2$)—(OCH$_2$CH$_2$)$_3$—, wherein R$_3$ is naphthylalanine;
—C(S)NH—R$_3$—(NHCH$_2$CH$_2$)—(OCH$_2$CH$_2$)$_3$—, wherein R$_3$ is -naphthylalanine-glycyl-lysine-;
—C(S)NH—R$_3$—(NHCH$_2$CH$_2$)—, wherein R$_5$ is -methionine-valine-lysine-;
—C(O)CH$_2$CH$_2$C(O)NHCH$_2$(C$_6$H$_6$)C(O)—R$_3$—(OCH$_2$CH$_2$)$_3$—, wherein R$_3$ is naphthylalanine;
—C(O)CH$_2$CH$_2$C(O)NH—R$_3$—(OCH$_2$CH$_2$)$_3$—, wherein R$_3$ is naphthylalanine-glycyl-lysine; and
—C(O)CH$_2$CH$_2$C(O)NH—R$_3$—(NHCH$_2$CH$_2$)—, wherein R$_3$ is methionine-lysine-valine.

The bifunctional chelator compounds may include a PEG spacer, wherein a PEG spacer may include any inert spacer that does not affect the conformational properties of the compound to which the spacer is attached. A PEG spacer of the present disclosure may include, but is not limited to, a PEG linker having an average molecular weight from 0.1 KD to 50 KD. The average molecular weight may be at least 0.1 KD, including, but not limited to, at least 0.5, 1, 5, 10, 15, 20, 25, 30, 35, 40, 45, and at least 50 KD. The average molecular weight may be no more than 50 KD, including, but not limited to, 45, 40, 35, 30, 25, 20, 15, 10, 5, 1, 0.5, and 0.1 KD. Any combination of lower and upper limits may define the average molecular weight, including, but not limited to, 0.1 KD to 1 KD, 1 KD to 5 KD, 5 KD to 15 KD, 15 KD to 25 KD, 25 KD to 35 KD, and 35 KD to 50 KD. The PEG spacer of the present disclosure may include (PEG)$_n$, wherein n is 1 or an integer greater than 1, such as an integer from 1 to 1000 or any integer value therein or any subrange of integers therein, such as from 1 to 100 or 1 to 20. For example, n may be 1, 2, 3, 4, 5, 6, 7, 8, 9, or 10.

The bifunctional chelator compounds of the present disclosure may include at least one amino acid or amino acid derivative. The at least one amino acid or amino acid derivative, may include, but is not limited to, Naphthylalanine, lysine, valine, methionine, glycyl, phenylalanyl, and the like.

The bifunctional chelator compounds of the present disclosure may include a chelator moiety, which may include, but it not limited to, dodecane tetraacetic acid (hereinafter "DOTA"), DOTA-GA, DOTA derivative chelator moieties, and the like. As used herein, "GA" may refer to glutaric acid. The present disclosure provides bifunctional chelator compounds in which the chelator moiety includes 1,4,7,10-tetraazacyclododecane-1,4,7-triacetic acid (DO3A) or a derivative thereof; 1,4,7-triazacyclononane-1,4-diacetic acid (NODA) or a derivative thereof; 1,4,7-triazacyclononane-1,4,7-triacetic acid (NOTA) or a derivative thereof; 1,4,7,10-tetraazacyclododecane-1,4,7,10-tetraacetic acid (DOTA) or a derivative thereof; 1,4,7-triazacyclononane, 1-glutaric acid-4,7-diacetic acid (NODAGA) or a derivative thereof; 1,4,7,10-tetraazacyclodecane, 1-glutaric acid-4,7,10-triacetic acid (DOTAGA) or a derivative thereof; 1,4,8,11-tetraazacyclotetradecane-1,4,8,11-tetraacetic acid (TETA) or a derivative thereof; 1,4,8,11-tetraazabicyclo[6.6.2]hexadecane-4,11-diacetic acid (CB-TE2A) or a derivative thereof; diethylene triamine pentaacetic acid (DTPA), its diester, or a derivative thereof; 2-cyclohexyl diethylene triamine pentaacetic acid (CHX-A"-DTPA) or a derivative thereof; deforoxamine (DFO) or a derivative thereof; 1,2-[[6-carboxypyridin-2-yl]methylamino]ethane (H2dedpa) or a derivative thereof; DADA or a derivative thereof; 1,4,7,10-Tetraazacyclododecane-1,4,7,10-tetra(methylene phosphonic acid) (DOTP) or a derivative thereof; 4-amino-6-[[16-[(6-carboxypyridin-2-yl)methyl]-1,4,10,13-tetraoxa-7,16-diazacyclooctadec-7-yl]methyl]pyridine-2-carboxylic acid (MACROPA-NH2) or a derivative thereof; MACROPA or a derivative thereof; 1,4,7,10-tetrakis(carbamoylmethyl)-1,4,7,10-tetraazacyclododecane (TCMC) or a derivative thereof; {4-[2-(bis-carboxymethylamino)-ethyl]-7-carboxymethyl-[1,4,7]triazonan-1-yl}-acetic acid (NETA) or a derivative thereof; Diamsar or a derivative thereof; 1,4,7-triazacyclononane-1,4,7-tris[methyl(2-carboxyethyl)phosphinic acid (TRAP, PRP9, TRAP-Pr) or a derivative thereof; N,N'-bis(6-carboxy-2-pyridylmethyl)ethylenediamine-N, N'-diacetic acid (H4octapa) or a derivative thereof; N,N"-[1-benzyl-1,2,3-triazole-4-yl]methyl-N,N-[6-(carboxy)pyridin-2-yl]-1,2-diaminoethane (H2azapa) or a derivative thereof; N,N"-[[6-(carboxy)pyridin-2-yl]methyl]diethylenetriamine-N,N',N"-triacetic acid (H5decapa) or a derivative thereof; N,N'-bis(2-hydroxy-5-sulfobenzyl)ethylenediamine-N,N'-diacetic acid (SHBED) or a derivative thereof; N,N'-bis(2-hydroxybenzyl)ethylenediamine-N,N'-diacetic acid (HBED) or a derivative thereof; 3,6,9,15-tetraazabicyclo[9.3.1]pentadeca-1(15),11,13-triene-3,6,9,-triacetic acid (PCTA) or a derivative thereof; desferrioxamine B (DFO) or a derivative thereof; N,N'-(methylenephosphonate)-N,N'-[6-(methoxycarbonyl)pyridin-2-yl]methyl-1,2-diaminoethane (H6phospa) or a derivative thereof; 1,4,7,10,13,16-hexaazacyclohexadecane-N,N',N''',N'''',N'''''-hexaacetic acid (HEHA) or a derivative thereof; 1,4,7,10,13-pentaazacyclopentadecane-N,N',N'',N''',N''''-pentaacetic acid (PEPA) or a derivative thereof; or 3,4,3-LI(1,2-HOPO) or a derivative thereof.

The protein or peptide may be a cancer cell targeting agent that binds to an antigen/target molecule that is preferentially expressed or overexpressed on mammalian cancer cells such as human cancer cells. The protein may be an antibody, such as a monoclonal antibody, or an antigen-binding fragment thereof such as a Fab fragment, Fab2 fragment, or scFv molecule, a minibody, a diabody, or a nanobody, or an antibody mimetic protein such as a designed ankyrin repeat proteins (DARPin).

The present disclosure provides compositions including, but not limited to, radiopharmaceutical compositions and/or radiodiagnostic (radio-imaging) compositions, and the like. Radiopharmaceutical compositions and/or radiodiagnostic compositions may include one or more pharmaceutically acceptable carriers or excipients. Such carriers and excipients are well known in the art. As a non-limiting example, injectable drug delivery systems include solutions, suspensions, gels, microspheres and polymeric injectables, and may include excipients such as solubility-altering agents (e.g., ethanol, propylene glycol and sucrose) and polymers (e.g., polycaprylactones and PLGA's). Radioconjugate aspects of the present disclosure may be formulated with excipients as substantially described in U.S. Pat. No. 10,420,851 or International Pub. No. WO 2017/155937, which are hereby incorporated by reference in their entirety. The formulation may include 0.5% to 5.0% (w/v) of one or more excipients, including, but not limited to, ascorbic acid, polyvinylpyrrolidone (PVP), human serum albumin (HSA), a water-soluble salt of HSA, any combination thereof, and the like. As a non-limiting example, the formulation may include 0.5-5% ascorbic acid; 0.5-4% polyvinylpyrrolidone (PVP); and a chelator conjugated affinity reagent protein such as an antibody, such as a monoclonal antibody, which may be radiolabeled or a chelated radionuclide in a buffered solution, such as in 50 mM PBS buffer, pH 7.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, radioprotectants, sorbents, suspending or dispersing agents, sweeteners, or waters of hydration. Exemplary excipients include, but are not limited to: ascorbic acid, histidine, phosphate buffer, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

As used herein, the term "antibody" includes, without limitation, (a) an immunoglobulin molecule including two heavy chains and two light chains and which recognizes an antigen; (b) polyclonal and monoclonal immunoglobulin molecules; (c) monovalent and divalent fragments thereof, such as Fab, di-Fab, as well as scFv molecules, diabodies, minibodies, single domain antibodies (sdAb), and nanobodies (VHH); (d) naturally occurring and non-naturally occurring, such as wholly synthetic antibodies, IgG-Fc-silent, and chimeric; and (e) bi-specific and multi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies may be human, humanized or nonhuman. When the present disclosure refers to or recites an "antibody," it is intended as referring to any of the full-length antibodies or fragments thereof disclosed herein, unless explicitly denoted otherwise. Further, wherever in this disclosure specific antibodies are disclosed, aspects directed to antigen binding fragments of such antibodies, such as Fab or Fab$_2$ fragments, or corresponding scFv molecules are intended to be provided and disclosed. Similarly, wherever in this disclosure specific antibodies are disclosed, corresponding aspects directed to full-length antibodies, antigen-binding antibody fragments, such as Fab or Fab$_2$ fragments, or scFv molecules that have the same immunoglobulin heavy chain CDRs and/or immunoglobulin light chain CDRs are also intended to be provided and disclosed. Such corresponding aspects may include one or both of the heavy chain variable region amino acid sequence and the light chain variable region amino acid sequence of the recited reference antibody. Antibody heavy chain and light chain complementarity determining regions (CDRs) and regions may be defined/delineated according to the Kabat or IMGT numbering conventions. Further, wherever in this disclosure antibody heavy chain or light chain sequences are disclosed that include N-terminal leader sequences, corresponding aspects including or consisting of the respective light chains without its leader sequence, e.g., beginning instead with the first amino acid residue of its respective variable region, are also intended to be provided and disclosed.

Single chain Fv molecules (scFv) are single polypeptide chain antibody molecules that include an immunoglobulin light chain variable region domain (VL domain) and an immunoglobulin heavy chain variable region domain (VH domain) joined by a peptide linker (L). An scFv molecule represents either VL-L-VH if the VL domain is the N-terminal part of the scFv molecule or VH-L-VL if the VH domain is the N-terminal part of the scFv molecule. Methods for making scFv molecules and for designing suitable peptide linkers are disclosed in U.S. Pat. Nos. 4,704,692 and 4,946,778, where are hereby incorporated by reference in their entirety.

The present disclosure provides a conjugate of any of the bifunctional chelators disclosed herein and a protein, such as a scFv molecule or a protein including at least one scFv molecule segment, that may include, in consecutive order (from amino to carboxyl terminal end), amino acids 1-120 of an immunoglobulin heavy chain variable region as disclosed herein (as a non-limiting example, where amino acid residue 1 is the first residue of the heavy chain variable region according to the Kabat numbering convention), followed by a linker amino acid sequence, followed by the amino acid sequence of a light chain variable region disclosed herein. The sequence of either or both of the heavy chain variable region portion and the light chain variable region portion of the scFv molecule may be minus 1, 2, 3, 4, or 5 amino acids at one or both ends with respect to the full-length variable region sequence. Such conjugates may be radiolabeled by chelation of a radionuclide to the chelator moiety of the conjugate.

The scFv linker amino acid sequence may, for example, include any of the amino acid sequences:

(SEQ ID NO: 122)
KISGGGGSGGGGSGGGGSGGGGSGGGGSS, (SEQ ID NO: 123)
SPNSASHSGSAPQTSSAPGSQ, (G$_3$S)$_n$ where, for example, n is 1, 2, 3, 4, 5, 6, 7, 8, 9, or 10, such as (G$_3$S)$_4$, or (G$_4$S)$_n$ where, for example, n is 1, 2, 3, 4, 5, 6, 7, 8, 9, or 10, such as (G$_4$S)$_5$.

It should be further understood herein that wherever in the sequences of this disclosure an immunoglobulin heavy chain sequence or an immunoglobulin light chain sequence are provided that may include an amino terminal signal peptide sequence, corresponding amino acid sequences without the signal peptide sequences are also intended to be disclosed and that the various aspects of the present disclosure may be embodied with either the versions of the proteins with the signal peptide sequence or corresponding versions without the signal peptide sequences, and in any combination.

A protein, such as an antibody or fragment thereof or scFv molecule, or an antibody mimetic or a peptide that is conjugated to any of the bifunctional linkers disclosed herein may specifically bind to target antigens specifically expressed by or overexpressed by various types of cancer cells, such as one or more cancer antigens, including, but not limited to, the human forms thereof: CD33, DR5, 5T4 (trophoblast glycoprotein), HER2 (ERBB2; Her2/neu), HER3, TROP2 (TROP-2, EGP1, EGP-1), mesothelin, TSHR, CD19, CD123, CD22, CD30, CD45, CD171, CD138, CS-1, CLL-1, GD2, GD3, B-cell maturation antigen (BCMA), Tn Ag, prostate specific membrane antigen (PSMA), ROR1, FLT3, fibroblast activation protein (FAP), a Somatostatin receptor, Somatostatin Receptor 2 (SSTR2), Somatostatin Receptor 5 (SSTR5), gastrin-releasing peptide receptor (GRPR), NKG2D ligands (such as MICA, MICB, RAET1E/ULBP4, RAET1G/ULBP5, RAET1H/ULBP2, RAET1/ULBP1, RAET1L/ULBP6, and RAET1N/ULBP3), LYPD3 (C4.4A), Nectin-4, urokinase plasminogen activator receptor (uPAR), Folate receptor alpha (FOLR1), CUB-domain containing protein 1 (CDCP1), Glypican-3 (GPC3), tenascin, tenascin-C, CEACAM5, Cadherin-3, CCK2R, Neurotensin receptor type 1 (NTSR1), human Kallikrein 2 (hK2), norepinephrine transporter, Integrin alpha-V-beta-6, CD37, CD66, CXCR4, Fibronectin extradomain B (EBD), LAT-1, Carbonic anhydrase IX (CAIX), B7-H3 (a/k/a CD276), Disialoganglioside GD2 Antigen (GD2), calreticulin, phosphatidylserine, GRP78 (BiP), TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (Fra), MUC1, epidermal growth factor receptor (EGFR), EGFRvIII, NCAM, Prostase, PAP, ELF2M, Ephrin B2, IGF-I receptor, CAIX, LMP2, gp100, bcr-abl, tyrosinase, EphA2, Fucosyl GM1, sLe, GM3, DR5, 5T4, TGSS, HMW-MAA, o-acetyl-GD2, Folate receptor beta, TEM1/CD248, TEM7R, CLDN6, GPRC5D, CXORF61, CD97, CD 179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, MAGEA3, MAGEA3/A6, ETV6-AML, sperm protein 17, XAGE1, Tie 2, MAD-CT-1, MAD-CT-2, Fos-related antigen 1, prostein, survivin and telomerase, PCTA-1/Galectin 8, KRAS, MelanA/MART1, Ras mutant, hTERT, sarcoma translocation breakpoints, ML-IAP, ERG (TMPRSS2 ETS fusion gene), NA17, PAX3, Androgen receptor, Cyclin B 1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GPA7, IGLL1, FGFR2, FGFR2b, Six-transmembrane epithelial antigen of prostate 1 (STEAP1), MUC17, claudin-18 isoform 2 (CLDN18.2), and Sortilin (Neurotensin receptor-3). Such conjugates radiolabeled by chelation with a radionuclide may be used to treat and/or diagnostically image a cancer in a mammalian subject such as a human patient. Targeting agents that are conjugated with a bifunctional chelator as disclosed herein may also include those that bind antigens expressed by immunosuppressive cells found in or associated with cancers such as CCR8 antigen expressed by tumor associated regulatory T-cells (Tregs) and CD33 antigen expressed by myeloid-derived suppressor cells (MDSCs) and tumor-associated macrophages (TAMs).

CD38 targeting agents that may be conjugated with any of the bifunctional chelators disclosed herein and radiolabeled for use as a radioconjugate include the monoclonal antibodies daratumumab (Darzalex®, Janssen Biotech, Inc.; heavy chain (SEQ ID NO:124), CDR-H1 (SEQ ID NO:125), CDR-H2 (SEQ ID NO:126), CDR-H3 (SEQ ID NO:127), light chain (SEQ ID NO:128), CDR-L1 (SEQ ID NO: 129), CDR-L2 (SEQ ID NO:130) and CDR-L3 (SEQ ID NO:131)), isatuximab (Sarclisa®, a/k/a SAR650984, Sanofi; reported heavy chain SEQ ID NO:132, CDR-H1 (SEQ ID NO:133), CDR-H2 (SEQ ID NO:134), CDR-H3 (SEQ ID NO:135), reported light chain SEQ ID NO:136, CDR-L1 (SEQ ID NO:137), CDR-L2 (SEQ ID NO:138), CDR-L3 (SEQ ID NO:139)), and MOR202 (MorphoSys AG; U.S. Pat. No. 8,088,896), as well as CD38-binding fragments thereof and antibodies having the same CDRs as daratumumab, isatuximab, or MOR202. CD38 targeting agents that may be conjugated with any of the bifunctional chelators disclosed herein and radiolabeled for use as a radioconjugate may include, but are not limited to, any of the anti-CD38 monoclonal antibodies disclosed in any of U.S. Pat. Nos. 8,088,896, 7,829,673, Int'l Pub. No. WO 2008/047242, U.S. Pat. No. 8,153,765 and U.S. Pub. No. 20210171653, CD38-binding fragments of any of said antibodies, and antibodies including the same CDRs as said antibodies.

The present disclosure provides a conjugate of any of the bifunctional chelators disclosed herein with a protein, such as an antibody, immunoglobulin heavy chain, immunoglobulin light chain, antibody fragment such as Fab fragment, Fab2 fragment or scFv molecules or fusion proteins, that include any of the amino acid sequences or combinations thereof set forth in SEQ ID NOS:1-139. The present disclosure provides a conjugate of any of the bifunctional chelators disclosed herein with any of the proteins, including, but not limited to, the antibodies, immunoglobulin heavy chains, immunoglobulin light chains, antibody fragments, such as Fab fragments, Fab2 fragments or scFv molecules, or fusion proteins that recognize cancer- or cancer-related antigens, disclosed in International Pub. No. WO2022235676 (of Int'l App. No. PCT/US2022/027479), which is hereby incorporated by reference in its entirety.

The protein that is conjugated with any of the bifunctional chelators disclosed herein may also be a modification of any one of the sequences set forth in any SEQ ID NOS: 1-139 that comprises one or more amino acid substitutions that have little to no effect on the structure or function of the sequence (e.g., conservative substitutions). In some aspects, two sequences are considered to be "homologous" to one another if the percent amino acid sequence identity is at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

DR5 targeting agents that may be conjugated with any of the bifunctional chelators disclosed herein and radiolabeled for use as a radioconjugate, may include, but are not limited to, any one or more of the monoclonal anti-DR5 antibodies mapatumumab, conatumumab, lexatumumab, tigatuzumab, drozitumab, and LBY-135.

5T4 targeting agents that may be conjugated with any of the bifunctional chelators disclosed herein and radiolabeled for use as a radioconjugate may include, but are not limited to, any one or more of the monoclonal anti-5T4 antibodies MED10641, ALG.APV-527, Tb535, H6-DM5, and ZV0508.

HER2 targeting agents that may be conjugated with any of the bifunctional chelators disclosed herein and radiolabeled for use as a radioconjugate may include the monoclonal antibodies trastuzumab and pertuzumab. The amino acid sequences of the light chain and the heavy chain of Trastuzumab reported by DrugBank Online are: light chain (SEQ ID NO:86) and heavy chain (SEQ ID NO:87). The amino acid sequences of the light chain and the heavy chain of Pertuzumab reported by DrugBank Online are: light chain (SEQ ID NO:88) and heavy chain (SEQ ID NO:89). The HER2 targeting agent used may be the ADC fam-trastuzumab deruxtecan-nxki (Enhertu®; Daiichi Sankyo, Japan).

HER3 targeting agents that may be conjugated with any of the bifunctional chelators disclosed herein and radiolabeled for use as a radioconjugate may include any one or more of the monoclonal antibodies patritumab, seribantumab, lumretuzumab, elgemtumab, GSK2849330, or AV-203 (Aveo Oncology) or any of the anti-HER3 antibodies disclosed in U.S. Pat. Nos. 10,494,441; 9,828,635; or U.S. Pub. No. 20210025006. An HER3 antibody may include, but is not limited to, an immunoglobulin heavy chain variable region including a CDRH1 including SEQ ID NO:56, a CDRH2 including SEQ ID NO:57, and a CDRH3 including SEQ ID NO:58, an immunoglobulin light chain variable region including a CDRL1 including SEQ ID NO:59, a CDRL2 including SEQ ID NO:60, and a CDRL3 including SEQ ID NO:61. An exemplary HER3 antibody includes an immunoglobulin heavy chain variable region including SEQ ID NO:62 and/or an immunoglobulin light chain variable region including SEQ ID NO:63. An exemplary HER3 antibody includes an immunoglobulin heavy chain amino acid sequence of SEQ ID NO:64 and/or an immunoglobulin light chain amino acid sequence of SEQ ID NO:65. The HER3 targeting agent used may be the ADC patritumab deruxtecan.

TROP2 targeting agents that may be conjugated with any of the bifunctional chelators disclosed herein and radiolabeled for use as a radioconjugate may include, but are not limited to, the monoclonal antibodies Sacituzumab and Datopotamab, antibodies having one or both of the heavy chain and light chain of said antibodies, antibodies having one or both of the heavy chain variable region and the light chain variable region of said antibodies, and antibodies having one or both of the heavy chain CDRs and the light chain CDRs of said antibodies, or TROP2-binding fragments of any of the aforementioned antibodies, such as Fab fragments, Fab₂ fragments, or corresponding scFv molecules. Sacituzumab biosimilar is commercially available as Catalog No. A2175 from BioVision Incorporated (an Abcam company, Waltham, MA, USA). Datopotamab biosimilar is commercially available as Catalog No. PX-TA1653 from ProteoGenix (Schiltigheim, France). The TROP2 targeting agent used may be the ADC Sacituzumab govitecan-hziy (Trodelvy®, Gilead Sciences, Inc., Foster City, CA, USA).

Further TROP2 targeting agents that may be conjugated with any of the bifunctional chelators disclosed herein and radiolabeled for use as a radioconjugate may include a monoclonal antibody having a heavy chain SEQ ID NO:66 and/or a light chain SEQ ID NO:71 (reported as the heavy and light chains of Sacituzumab), or an antibody including one or both of the heavy chain variable region (SEQ ID NO:67) or the light chain variable region (SEQ ID NO:72) of said chains, or an antibody including 1, 2, or 3 of the heavy chain CDRs of said heavy chain (CDR H1-3: SEQ ID NOS:68-70 respectively) and/or 1, 2 or 3 of the light chain CDRs of said light chain (CDR L1-3: SEQ ID NOS:73-75 respectively), and any of the anti-human TROP antibodies disclosed in U.S. Pat. No. 7,238,785 (such as mAb hRS7), U.S. Pat. Nos. 9,492,566, 10,195,517, or 11,116,846, or an antibody including one or both of the heavy chain and light chain variable regions of said antibodies, or an antibody including a heavy chain including 1, 2 or 3 of the heavy chain CDRs of any of said antibodies and/or a light chain including 1, 2, or 3 of the light chain CDRs of any of said antibodies.

TROP2 targeting agents that may be conjugated with any of the bifunctional chelators disclosed herein and radiolabeled for use as a radioconjugate may include, but are not limited to, a monoclonal antibody heavy chain SEQ ID NO:76 and/or a light chain SEQ ID NO:81 (reported as the heavy and light chains of Datopotamab), or an antibody including one or both of the variable region of said heavy chain (SEQ ID NO:77) and the variable region of said light chain (SEQ ID NO:82), or an antibody including 1, 2, or 3 of the heavy chain CDRs of said heavy chain (CDRs 1-3: SEQ ID NOS:78-80 respectively) and/or 1, 2 or 3 of the light chain CDRs of the said light chain (CDR H1-3: SEQ ID NOS:83-85 respectively), and any of the anti-human TROP antibodies disclosed in Int'l Pub. No. WO2015098099 or U.S. Pub. No. 20210238303, or an antibody including one or both of the heavy chain and light chain variable regions of said antibodies, or an antibody including a heavy chain including 1, 2 or 3 of the heavy chain CDRs of any of said antibodies and/or a light chain including 1, 2, or 3 of the light chain CDRs of any of said antibodies.

CD33 targeting agents that may be conjugated with any of the bifunctional chelators disclosed herein and radiolabeled for use as a radioconjugate may include the monoclonal antibodies lintuzumab (HuM195), gemtuzumab, and vadastuximab.

MUC1 targeting agents that may be conjugated with any of the bifunctional chelators disclosed herein and radiolabeled for use as a radioconjugate include hTAB004 (OncoTAb, Inc.) and any of the anti-MUC1 antibodies or antibody fragments disclosed in any of U.S. Pub. No. 20200061216 and U.S. Pat. Nos. 8,518,405; 9,090,698; 9,217,038; 9,546,217; 10,017,580; 10,507,251 10,517,966; 10,919,973; 11,136,410; and 11,161,911.

LYPD3 (C4.4A) targeting agents that may be conjugated with any of the bifunctional chelators disclosed herein and radiolabeled for use as a radioconjugate may include, but are not limited to, BAY 1129980 (a/k/a Lupartumab amadotin; Bayer AG, Germany) an Auristatin-based anti-C4.4A (LYPD3) ADC or its antibody component Lupartumab, IgG₁ mAb GT-002 (Glycotope GmbH, Germany) and any of those disclosed in U.S. Pub. No. 20210309711, 20210238292, 20210164985, 20180031566, 20170158775, or 20150030618, 20120321619, Canadian Patent Application No. CA3124332A1, Taiwan Application No. TW202202521A, or Int'l Pub. No. WO2021260208, WO2007044756, WO2022042690, or WO2020138489.

5T4 targeting agents that may be conjugated with any of the bifunctional chelators disclosed herein and radiolabeled for use as a radioconjugate may include, but are not limited to, 5T4-binding, single chain, chimeric antibody-superantigen fusion proteins such as C215Fab-(SEQ ID NO:93), 5T4Fab-SEA$_{D227A}$ (SEQ ID NO:94), and 5T4Fab-SEA/ESEA-120 (SEQ ID NO:95). For example, naptumomab estafenatox is SEQ ID NO:96 (chimeric heavy chain component) non-covalently bound to SEQ ID NO:97 (light chain component). The heavy chain may include a 5T4 Fab heavy chain component (corresponding to residues 1 to 222 of SEQ ID NO:95), the SEA/E-120 superantigen (corresponding to residues 226 to 458 of SEQ ID NO:95), and a GGP tripeptide linker (corresponding to residues 223-225 of SEQ ID NO:95) covalently linking the Fab heavy chain and SEA/E-120 components. The light chain may include residues 459 to 672 of SEQ ID NO:95.

5T4 targeting agents that may be conjugated with any of the bifunctional chelators disclosed herein and radiolabeled for use as a radioconjugate may include, but are not limited to, C215Fab-SEA (SEQ ID NO:93), 5T4Fab-SEAD227A (SEQ ID NO:94), 5T4Fab-SEA/E-120 (SEQ ID NO:95); SEQ ID NO:96, Naptumomab estafenatox reported as SEQ ID NO:96 (heavy chain component) non-covalently associated with SEQ ID NO:97 (light chain component), an antibody including the Fab component of Naptumomab estafenatox, an antibody including the heavy chain component of any one of SEQ ID NOS:93-96 (for example, lacking the enterotoxin components thereof), a 5T4-binding antibody including the heavy chain component of any one of SEQ ID NOS:93-96 and an associated light chain component such as the light chain component of SEQ ID NO:97, a 5T4-binding antibody (such as a single- or multi-chain antibody, such as but not limited to a human or humanized IgG, such as IgG1) including a heavy chain component that includes 2 or 3 of the heavy chain CDRs present in any one of SEQ ID NOS:93-96, Naptumomab estafenatox modified by covalent linkage of the heavy chain and light chain components to each other by disulfide bonds (between cysteine residues in the manner of a Fab) and/or by a bifunctional thiol reactive crosslinking agent which may include and introduce a chelating moiety (such as DOTA), any of the chimeric 5T4-binding superantigen fusion proteins of U.S. Pat. Nos. 7,615,225 10,314,910 and U.S. Pub. No. 20200101160, any of the preceding 5T4 targeting agents in which the antibody component(s) is/are humanized, any of the preceding in which an amino acid (for example, of a heavy chain and/or of a light chain) is substituted to a cysteine, and any of the preceding further including at least one additional amino acid (for example, in a heavy chain and/or in a light chain thereof) of which at least one is a cysteine and/or at least one is a lysine (for example, one or more additional C-terminal amino acids of which one or more are cysteines and/or of which one or more are lysines).

Light chain variations that may also be used include, but are not limited to, SEQ ID NO:99 (SEQ ID NO:97 with C-terminal lysine), SEQ ID NO:100 (SEQ ID NO: 97 with C-terminal cysteine), SEQ ID NO:101 (SEQ ID NO:97 with C-terminal lys-cys), and a light chain or light chain segment including 2 or 3 of the CDRs of the light chain of SEQ ID NO:97—namely CDR-L1 KASQSVSNDVA (SEQ ID NO:119), CDR-L2 YTSSRYA (SEQ ID NO:120), and CDR-L3 QQDYNSPPT (SEQ ID NO:121).

Further 5T4 targeting agents that may be conjugated with any of the bifunctional chelators disclosed herein, and optionally radiolabeled, include proteins having or consisting of the following:

SEQ ID NO:102 [heavy chain portion only of SEQ ID NO:96];

an immunoglobulin heavy chain or heavy chain segment including 2 or 3 of the heavy chain CDRs found in SEQ ID NO:20, namely CDR-H1 GYYMH (SEQ ID NO:116), CDR-H2 RINPNNGVTLYNQKFKD (SEQ ID NO:117), and CDR-H3 STMITNYVMDY (SEQ ID NO:118);

SEQ ID NO:103 [SEQ ID NO:96 including linker, excluding enterotoxin portion];

SEQ ID NO:104 [SEQ ID NO:102 with C-terminal lysine];

SEQ ID NO:105 [SEQ ID NO:103 with C-terminal lysine];

SEQ ID NO:106 [SEQ ID NO:102 with C-terminal cysteine];

SEQ ID NO:107 [SEQ ID NO:103 with C-terminal cysteine];

SEQ ID NO:108 [SEQ ID NO:102 with C-terminal lys-cys];

SEQ ID NO:109 [SEQ ID NO:103 with C-terminal lys-cys];

SEQ ID NO:110 [5T4Fab-SEA/E-120 (SEQ ID NO:95) with C-terminal lysine];

SEQ ID NO:111 [SEQ ID NO:96 with C-terminal lysine];

SEQ ID NO:112 [5T4Fab-SEA/E-120 (SEQ ID NO:95) with C-terminal cysteine];

SEQ ID NO:113 [SEQ ID NO:96 with C-terminal cysteine];

SEQ ID NO:114 [5T4Fab-SEA/E-120 (SEQ ID NO:95) with C-terminal lys-cys];

SEQ ID NO:115 [SEQ ID NO:96 with C-terminal lys-cys]; and any of SEQ ID NOS:96, 102-109, 111, 113 and 115 in non-covalent association with any of light chain SEQ ID NOS:97 and 99-101 to form a Fab without covalent cross-linking between chains, or a disulfide-bonded (cross-linked) form of such a Fab, or a form of such a Fab covalently cross-linked by a bifunctional cross-linker that may include a chelator such as DOTA.

The 5T4 targeting agent that may be conjugated to any of the bifunctional chelators disclosed herein may include, but is not limited to, an antibody, an antigen-binding antibody fragment, such as Fab or $Fab_2$, or an scFv molecule or a fusion protein, that includes immunoglobulin heavy chain CDRs 1, 2 and 3 as set forth in SEQ ID NOS:116, 117 and 118 respectively, and/or immunoglobulin light chain CDRs 1, 2 and 3 as set forth in SEQ ID NOS:119, 120 and 121 respectively. Such 5T4 targeting agents may further include an enterotoxin portion as disclosed herein, such as any of the modified enterotoxins SEA/E-120 (SEQ ID NO:91), $SEA_{D227A}$ (SEQ ID NO:92), and SEQ ID NO:98.

Where the 5T4 targeting agent includes a heavy chain and a light chain, one or both of the heavy chain and the light chain may be radiolabeled, for example, by chemical conjugation to any of the bifunctional chelators disclosed herein, and chelation of a radionuclide, such as $^{225}$Ac or $^{177}$Lu, by the chelator.

Figure 22:
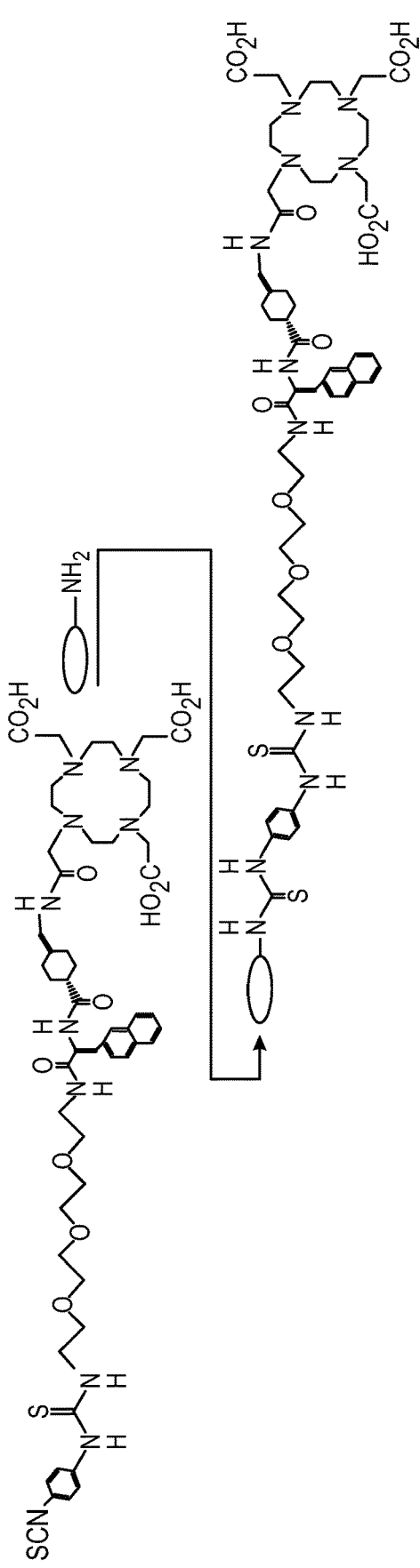
FIG. 22 shows conjugation of a bifunctional chelator molecule having a SCN reactive group to a primary amine of an amine presenting molecule.
Figure 23:
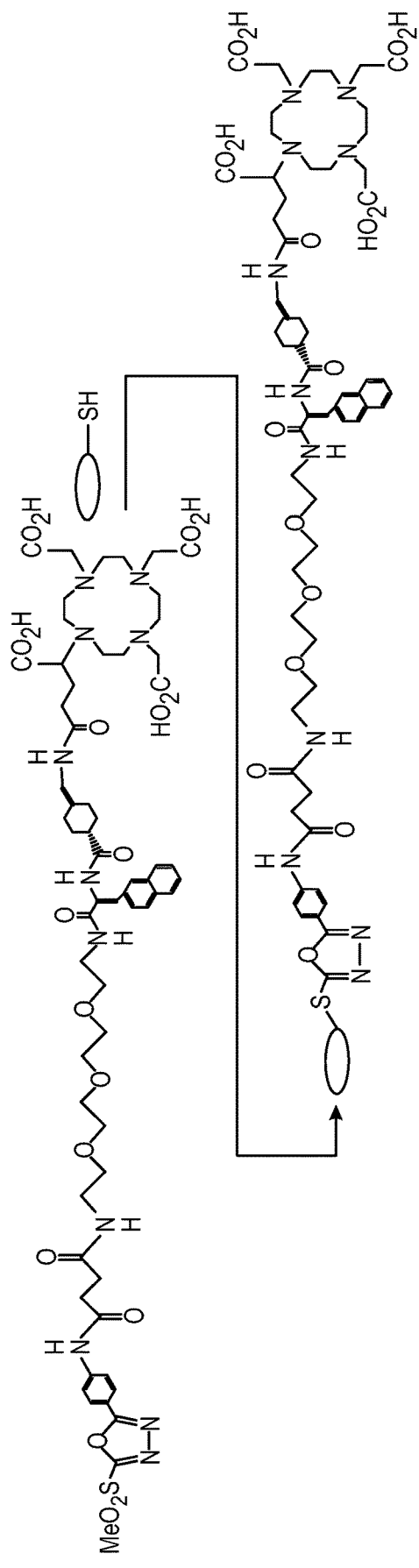
FIG. 23 shows conjugation of a bifunctional chelator molecule having a PODS reactive group to a thiol of a thiol presenting molecule.
Figure 24:
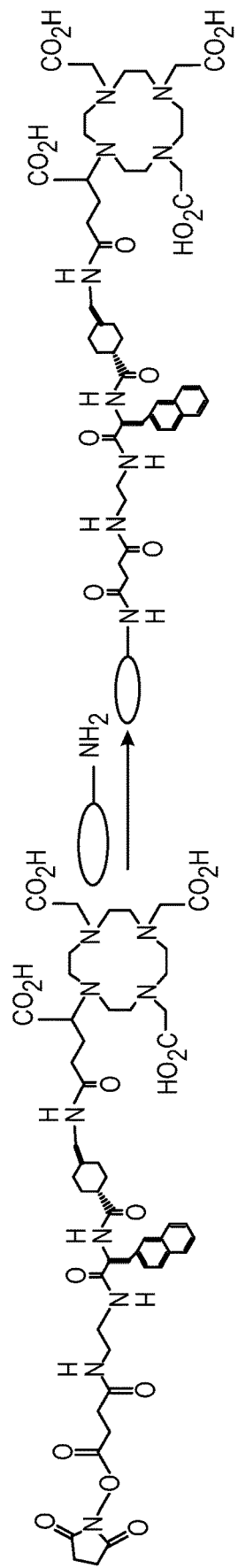
FIG. 24 shows conjugation of a bifunctional chelator molecule having a NHS reactive group to a primary amine of an amine presenting molecule.

The present disclosure provides a method for manufacturing a chelator-conjugated molecule, including the steps: reacting a molecule having at least one primary amine group with a bifunctional chelator compound of the present disclosure having an NHS or SCN reactive group to conjugate a chelator moiety of the bifunctional chelator compound to the molecule and/or reacting a molecule having at least one free thiol group with a bifunctional chelator compound of the present disclosure having a PODS reactive group to conjugate the bifunctional chelator compound to the molecule. Exemplary conjugation reactions are shown in FIGS. 22-24. The molecule may include, but is not limited to, a peptide, a synthetic peptide, a protein, a peptide ligand of a receptor protein, or a recombinant protein. The molecule may include, but is not limited to, an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

The method may include chelating one or more radionuclides to the chelator moiety of the bifunctional chelator compound before and/or after performing the conjugation. One or more radionuclide includes, but is not limited to, one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th. Accordingly, the molecule may include, but is not limited to, a 5T4 targeting agent of the present disclosure, wherein the 5T4 targeting agent binds human 5T4, such as naptumomab estafenatox. The molecule may include, but is not limited to, a CD38 targeting agent of the present disclosure.

The 5T4 targeting agent may include, but is not limited to, an antibody, an antibody fragment or an scFv molecule including an immunoglobulin heavy chain having complementarity determining regions 1-3 with amino acid sequences as set forth in SEQ ID NOS:116-118, respectively, and/or immunoglobulin light chain having complementarity determining regions 1-3 with amino acid sequences as set forth in SEQ ID NOS:119-121, respectively.

The present disclosure further provides a method of manufacturing a chelator-conjugated molecule according to Example 1.

The present disclosure provides a method of synthesizing a bifunctional chelator compound of the present disclosure according to Example 2, as shown in FIGS. 18-21.

Definitions

Unless otherwise defined, all terms (including technical and scientific terms) used herein have the same meaning as commonly understood by one of ordinary skill in the art to which this disclosure belongs.

As used herein, the term "and/or" includes any and all combinations of one or more of the associated listed items. Likewise, as used in the following detailed description, the term "or" is intended to mean an inclusive "or" rather than an exclusive "or." That is, unless specified otherwise, or clear from context, "X employs A or B" is intended to mean any of the natural inclusive permutations. Thus, if X employs A; X employs B; or X employs both A and B, then "X employs A or B" is satisfied under any of the foregoing instances.

The terminology used herein is for the purpose of describing particular examples only and is not intended to be limiting. As used herein, the singular forms "a", "an", and "the" may be intended to include the plural forms as well, unless the context clearly dictates otherwise. As example, "a" compound may comprise one or more compounds, and the like.

The terms "comprises", "comprising", "including", "having", and "characterized by", may be inclusive and therefore specify the presence of stated features, elements, compositions, steps, integers, operations, and/or components, but do not preclude the presence or addition of one or more other features, integers, steps, operations, elements, components, and/or groups thereof. Although these open-ended terms may be to be understood as a non-restrictive term used to describe and claim various aspects set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, described herein also specifically includes embodiments consisting of, or consisting essentially of, such recited compositions, materials, components, elements, features, integers, operations, and/or process steps. In the case of "consisting of", the alternative embodiment excludes any additional compositions, materials, components, elements, features, integers, operations, and/or process steps, while in the case of "consisting essentially of", any additional compositions, materials, components, elements, features, integers, operations, and/or process steps that materially affect the basic and novel characteristics may be excluded from such an embodiment, but any compositions, materials, components, elements, features, integers, operations, and/or process steps that do not materially affect the basic and novel characteristics may be included in the embodiment.

Any method steps, processes, and operations described herein may not be construed as necessarily requiring their performance in the particular order discussed or illustrated, unless specifically identified as an order of performance. Thus, where a particular order is exemplified in this disclosure, corresponding aspects or embodiments having different ordering are also intended to be provided and disclosed. It is also understood that additional or alternative steps may be employed, unless otherwise indicated.

In addition, features described with respect to certain example embodiments may be combined in or with various other example embodiments in any permutational or combinatory manner. Different aspects or elements of example embodiments, as disclosed herein, may be combined in a similar manner. The term "combination", "combinatory," or "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included may be combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

In the description, certain details are set forth in order to provide a better understanding of various aspects of the systems and methods disclosed herein. However, one skilled in the art will understand that these aspects may be practiced without these details and/or in the absence of any details not described herein. In other instances, well-known structures, methods, and/or techniques associated with methods of practicing the various embodiments may not be shown or described in detail to avoid unnecessarily obscuring descriptions of other details of the various embodiments.

While specific aspects of the disclosure have been provided hereinabove, the disclosure may, however, be embodied in many different forms and should not be construed as necessarily being limited to only the embodiments disclosed herein. Rather, these embodiments may be provided so that this disclosure is thorough and complete, and fully conveys various concepts of this disclosure to skilled artisans.

All numerical quantities stated herein may be approximate, unless stated otherwise. Accordingly, the term "about" may be inferred when not expressly stated. The numerical quantities disclosed herein may be to be understood as not being strictly limited to the exact numerical values recited. Instead, unless stated otherwise, each numerical value stated herein is intended to mean both the recited value and a functionally equivalent range surrounding that value. At the very least, and not as an attempt to limit the application of the doctrine of equivalents to the scope of the claims, each numerical value should at least be construed in light of the number of reported significant digits and by applying ordinary rounding processes. Typical exemplary degrees of error may be within 20%, 10%, or 5% of a given value or range of values. Alternatively, the term "about" refers to values within an order of magnitude, potentially within 5-fold or 2-fold of a given value. Notwithstanding the approximations of numerical quantities stated herein, the numerical quantities described in specific examples of actual measured values may be reported as precisely as possible. Any numerical values, however, inherently contain certain errors necessarily resulting from the standard deviation found in their respective testing measurements.

All numerical ranges stated herein include all sub-ranges subsumed therein. For example, a range of "1 to 10" or "1-10" is intended to include all sub-ranges between and including the recited minimum value of 1 and the recited maximum value of 10 because the disclosed numerical ranges may be continuous and include every value between the minimum and maximum values. Any maximum numerical limitation recited herein is intended to include all lower numerical limitations. Any minimum numerical limitation recited herein is intended to include all higher numerical limitations.

Features or functionality described with respect to certain example aspects may be combined and sub-combined in and/or with various other example aspects. Also, different aspects and/or elements of example aspects, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, may be at least partially performed via at least one entity or actor in any manner.

All documents cited herein may be incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to this application.

While particular aspects have been illustrated and described, it would be obvious to those skilled in the art that various other changes and modifications may be made without departing from the spirit and scope of the invention. Those skilled in the art will recognize or be able to ascertain using no more than routine experimentation, numerous equivalents to the specific apparatuses and methods described herein, including alternatives, variants, additions, deletions, modifications, and substitutions. This application including the appended claims is therefore intended to cover all such changes and modifications that may be within the scope of this application.

The term "functionally equivalent variant" or "functionally active variant" of an amino acid sequence of the present disclosure refers to a sequence resulting from modification of the amino acid sequence of the present disclosure by insertion, deletion, or substitution of one or more amino acids or nucleotides within the sequence or at either or both distal ends of the sequence, and which modification does not affect (in particular impair) a function of the amino acid sequence. The functionally active variant may be obtained by sequence alterations in the amino acid sequence, wherein the sequence alterations retain a function of the unaltered amino acid sequence. Such sequence alterations may include, but are not limited to, (conservative) substitutions, additions, deletions, mutations, and insertions.

The variant of the peptide is functionally active in the context of this disclosure if the activity of the amino acid sequence amounts to at least 10%, preferably at least 25%, more preferably at least more preferably 50%, even more preferably at least 70%, still more preferably at least 80%, especially at least 90%, particularly at least 95%, and most preferably at least 99% of the biological activity of the amino acid sequence as used according to the present disclosure, including the amino acid sequence without sequence alteration (i.e. the original sequence).

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with unchanged polar side chains, with small side chains, with large side chains, etc.

In another aspect of the present disclosure, the amino acid sequences as defined above may be modified by a variety of chemical techniques to produce derivatives having essentially the same activity (as defined above for fragments and variants) as the amino acid sequences, and optionally having other desirable properties.

As used herein, "percent (%) amino acid sequence identity" with respect to the amino acid sequences identified herein is defined as the percentage of amino acid residues in a candidate sequence that are identical with the amino acid residues in the specific amino acid sequence, after aligning the sequence and introducing gaps, if necessary, to achieve the maximum percent sequence identity, and not considering any conservative substitutions as part of the sequence identity. Those skilled in the art may determine appropriate parameters for measuring alignment, including any algorithms such as BLAST needed to achieve maximal alignment over the full length of the sequences being compared.

ASPECTS

Aspect 1: A bifunctional chelator compound comprising a formula (A)

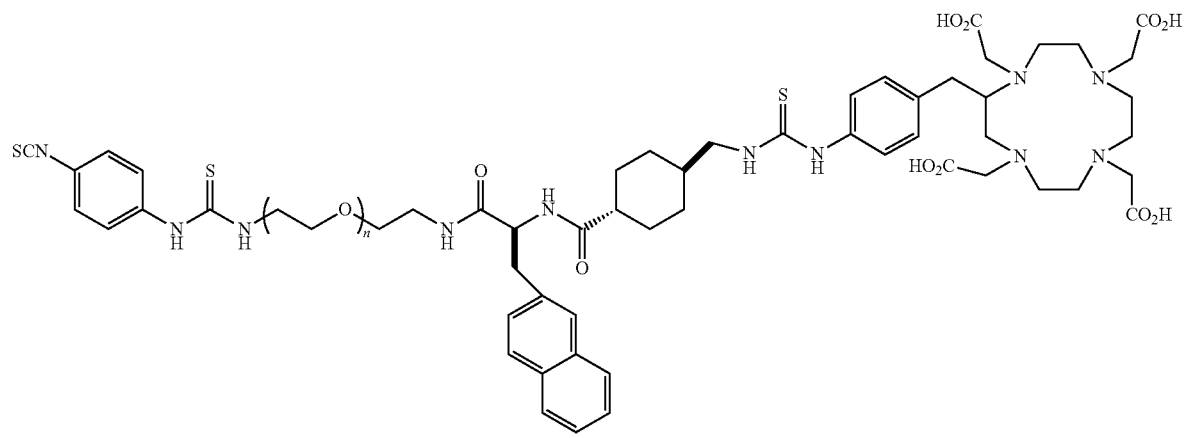

wherein n is 1 or an integer greater than 1.

Aspect 2: The bifunctional chelator of aspect 1, further comprising at least one radionuclide, wherein the radionuclide is chelated by the bifunctional chelator.

Aspect 3: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 4: A bifunctional chelator compound comprising a formula (B)

Aspect 5: The bifunctional chelator of aspect 4, further comprising at least one radionuclide, wherein the radionuclide is chelated by the bifunctional chelator.

Aspect 6: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 7: A bifunctional chelator compound comprising a formula (C) through formula (Q).

Aspect 8: The bifunctional chelator of aspect 7, further comprising at least one radionuclide, wherein the radionuclide is chelated by the bifunctional chelator.

Aspect 9: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 10: A bifunctional chelator compound comprising a formula (I)

$$M\text{-}L_1\text{-}R \quad (I)$$

wherein R is a reactive group, wherein $L_1$ is a linker group, and wherein M is a chelator moiety.

Aspect 11: The bifunctional chelator of aspect 10, wherein $L_1$ comprises a formula (IA):

—CH$_2$(C$_6$H$_4$)NH—R$_2$—(R$_3$)$_{n2}$—(R$_4$)$_{n3}$—(C(O))$_{n4}$—(R$_5$)$_n$—(NHCH$_2$CH$_2$)$_{n5}$—(OCH$_2$CH$_2$)$_{n6}$—R$_6$—(C$_6$H)$_{n7}$— wherein n2-n7 is 0 or 1;
$R_2$ is —C(S)—, —C(S)NH—, —C(O)CH$_2$CH$_2$—, C(O)CH$_2$CH$_2$C(O)—;
$R_3$ is CH$_2$, NHCH$_2$, or (CH$_2$)$_{n1}$, wherein n1 is 1 to 5;
$R_4$ is a cyclic alkane having 5 to 8 carbons or linear alkane having 1 to 6 carbons;
$R_5$ is an amino acid or amino acid derivative, wherein n is 1, 2, or 3; and
$R_6$ is —NHC(S)NH—, —C(S)NH, —C(O)NH—, NH(CH$_2$)$_2$NHC(O)(CH$_2$)$_2$, or NHC(O)(CH$_2$)$_2$—.

Aspect 12: The bifunctional chelator compound according to any of the foregoing aspects, further comprising at least one radionuclide, wherein the radionuclide is chelated by the bifunctional chelator.

Aspect 13: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 14: A bifunctional chelator compound comprising a formula (II)

$$M\text{-}L_2\text{-}R \quad (II)$$

wherein R is a reactive group, wherein $L_2$ is a linker group, and wherein M is a chelator moiety.

Aspect 15: The bifunctional chelator of aspect 14, wherein $L_2$ may include the formula (IIA):

—R$_1$—(R$_2$)$_{n1}$—(C(O))$_{n2}$—(R$_3$)$_n$—(NHCH$_2$CH$_2$)$_{n3}$—(OCH$_2$CH$_2$)$_{n4}$—R$_5$—(C$_6$H$_4$)$_{n4}$— wherein n1-n5 is 0 or 1;
$R_1$ is —CH$_2$C(O)NHCH$_2$—, —C(CO$_2$H)CH$_2$CH$_2$C(O)NHCH$_2$—, —C(CO$_2$H)CH$_2$CH$_2$C(O)—, or —C(CO$_2$H)CH$_2$CH$_2$;
$R_2$ is a cyclic alkane having 5 to 8 carbons or linear alkane having 1 to 6 carbons;
$R_3$ is an amino acid or amino acid derivative, wherein n is 1, 2, or 3; and
$R_4$ is —NHC(S)NH—, —C(S)NH—, —NHC(O)CH$_2$CH$_2$C(O)NH—, —NHC(O)CH$_2$CH$_2$C(O)—, —NHC(O)CH$_2$CH$_2$—, —C(O)CH$_2$CH$_2$C(O)NH—, or —C(O)CH$_2$CH$_2$C(O)—.

Aspect 16: The bifunctional chelator compound according to any of the foregoing aspects, further comprising at least one radionuclide, wherein the radionuclide is chelated by the bifunctional chelator.

Aspect 17: The bifunctional chelator compound according to any of the foregoing aspects wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 18: A bifunctional chelator compound comprising a formula (III):

$$M_1\text{-}L_a\text{-}R \quad \text{(III)}$$

wherein R is a reactive group, wherein $L_a$ is a linker group, and wherein $M_1$ is a chelator moiety.

Aspect 19: The bifunctional chelator compound according to aspect 18, wherein $L_a$ may include the formula (IIIG):

$$L_a = -(R_1)_{n1}-(R_3)_n-(NHCH_2CH_2)_{n3}-(OCH_2CH_2)_{n4}-$$

wherein n1-n4 is 0 or 1;
$R_1$ is $-C(S)NHCH_2-(R_2)_{n2}-C(O)$, $-C(S)NHNHCH_2-(R_2)_{n2}-C(O)$, $-NHCH_2-(R_2)_{n2}-C(O)$, $-C(S)NH$, $-C(O)CH_2CH_2C(O)NH(R_2)C(O)-$, $-C(O)CH_2CH_2C(O)NHCH_2(R_2)C(O)-$, $-R_2C(O)$, or $-C(O)CH_2CH_2C(O)NH-$;
$R_2$ is a cyclohexane or $CH_2R_2$ is a cyclohexane or $CH_2$; and
$R_3$ is an amino acid or amino acid derivative, wherein n is 1, 2, or 3.

Aspect 20: The bifunctional chelator compound according to any of the foregoing aspects, wherein the chelator moiety is selected from:

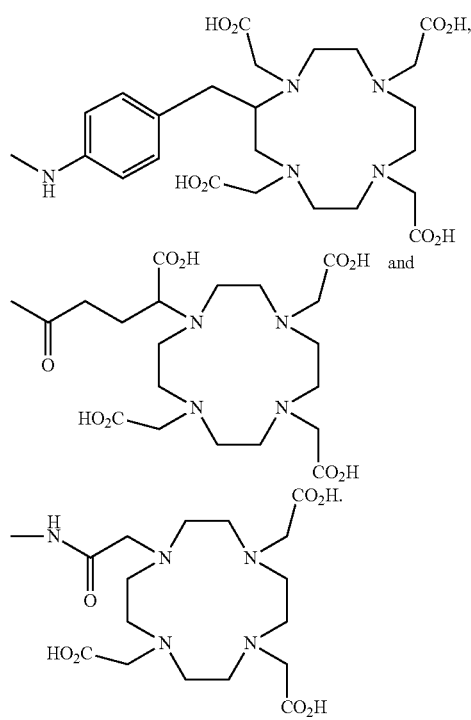

Aspect 21: The bifunctional chelator of claim according to any of the foregoing aspects, wherein the reactive group is selected from:

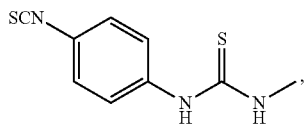

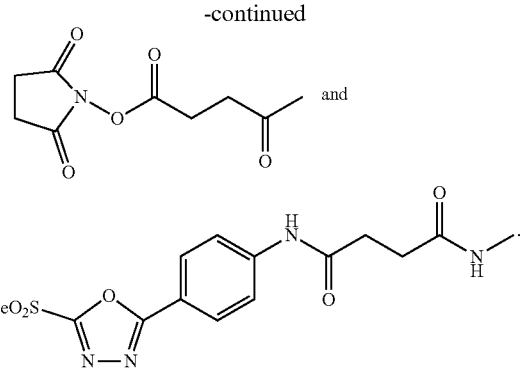

Aspect 22: The bifunctional chelator compound according to any of the foregoing aspects, further comprising at least one radionuclide, wherein the radionuclide is chelated by the bifunctional chelator.

Aspect 23: The bifunctional chelator compound according to any of the foregoing aspects, wherein the at least one radionuclide comprises $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, or $^{227}$Th.

Aspect 24: A conjugate of the bifunctional chelator compound of aspects 1-23 with a molecule comprising either of a primary amine group or a free thiol group.

Aspect 25: The conjugate of aspect 24, wherein the molecule comprises a peptide, a synthetic peptide, a protein, a recombinant protein, an antibody, a monoclonal antibody, an antigen-binding fragment of an antibody, an antigen-binding fragment of a monoclonal antibody, an immunoglobulin heavy chain, an immunoglobulin heavy chain variable region, immunoglobulin light chain, an immunoglobulin light chain variable region, a nanobody, a scFv molecule, or an antibody mimetic protein.

Aspect 26: The conjugate according to any of the foregoing aspects, wherein the molecule is a CD38 targeting agent.

Aspect 27: The conjugate according to any of the foregoing aspects, wherein the CD38 targeting agent is daratumumab, isatuximab, or MOR202.

Aspect 28: The conjugate according to any of the foregoing aspects, wherein the CD38 targeting agent is an antibody or an antibody fragment, comprising:
an immunoglobulin heavy chain having the amino acid sequence as set forth in SEQ ID NO:124 and/or an immunoglobulin light chain having an amino acid sequence as set forth in SEQ ID NO:128;
an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 29: The conjugate according to any of the foregoing aspects, wherein the molecule is a TROP2 targeting agent, wherein the TROP2 targeting agent binds human TROP2.

Aspect 30: The conjugate according to any of the foregoing aspects, wherein the TROP2 targeting agent is an antibody, an antibody fragment, or an scFv molecule, comprising:
an immunoglobulin heavy chain having complementarity determining regions 1-3 of Sacituzumab and/or an immunoglobulin light chain having complementarity determining regions 1-3 of Sacituzumab;
an immunoglobulin heavy chain having complementarity determining regions 1-3 with amino acid sequences as set forth in SEQ ID NOS:68-70, respectively, and/or an immunoglobulin light chain having complementarity determining regions 1-3 with amino acid sequences as set forth in SEQ ID NOS:73-75, respectively;
an immunoglobulin heavy chain having complementarity determining regions 1-3 of Datopotamab and/or an immunoglobulin light chain having complementarity determining regions 1-3 of Datopotamab; or
an immunoglobin heavy chain having complementarity determining regions 1-3 with amino acid sequences as set forth in SEQ ID NOS: 78-80, respectively, and/or an immunoglobulin light chain having complementarity determining regions 1-3 with amino acid sequences as set forth in SEQ ID NOS: 83-85, respectively.

Aspect 31: The conjugate according to any of the foregoing aspects, comprising the immunoglobulin heavy chain having complementarity determining regions with amino acid sequences as set forth in SEQ ID NOS:68-70 and/or the immunoglobulin light chain having complementarity determining regions with amino acid sequences as set forth in SEQ ID NOS:73-75; or comprising the immunoglobulin heavy chain having complementarity determining regions with amino acid sequences as set forth in SEQ ID NOS: 78-80 and/or the immunoglobulin light chain having complementarity determining regions with amino acid sequences as set forth in SEQ ID NOS: 83-85.

Aspect 32: The conjugate according to any of the foregoing aspects, wherein the molecule is a 5T4 targeting agent, wherein the 5T4 targeting agent binds human 5T4.

Aspect 33: The conjugate according to any of the foregoing aspects, wherein the 5T4 targeting agent is naptumomab estafenatox.

Aspect 34: The conjugate according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or immunoglobulin light chain having complementarity determining regions 1-3 with amino acid sequences as set forth in SEQ ID NOS:119-121, respectively.

Aspect 35: A composition comprising:
a quantity of a conjugate according to any of the foregoing aspects; and
at least one excipient.

Aspect 36: A composition comprising:
a quantity of a conjugate according to any of the foregoing aspects,
wherein the quantity of the conjugate comprises:
a radiolabeled fraction, wherein the bifunctional chelator compound comprises a chelator moiety, wherein the chelator moiety chelates one or more radionuclides, and
a non-radiolabeled fraction wherein the chelator moiety does not chelate a radionuclide.

Aspect 37: The composition according to any of the foregoing aspects, wherein the at least one radionuclide comprises one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 38: The composition according to any of the foregoing aspects, further comprising at least one excipient.

Aspect 39: A method for manufacturing a chelator-conjugated molecule, comprising the steps:
reacting a molecule comprising at least one primary amine group with a bifunctional chelator compound having a NHS or SCN reactive group according to any one of claims 1 through 23 to conjugate the bifunctional chelator compound to the molecule.

Aspect 40: The method of aspect 39, wherein the molecule comprises a peptide, a synthetic peptide, a protein, or a recombinant protein.

Aspect 41: The method according to any of the foregoing aspects, wherein the molecule comprises an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

Aspect 42: The method according to any of the foregoing aspects, wherein the molecule is a CD38 targeting agent.

Aspect 43: The method according to any of the foregoing aspects, wherein the CD38 targeting agent is daratumumab, isatuximab, or MOR202.

Aspect 44: The method according to any of the foregoing aspects, wherein the molecule comprises a peptide ligand of a receptor protein.

Aspect 45: The method according to any of the foregoing aspects, further comprising the step of chelating one or more radionuclides to the chelator moiety of the bifunctional chelator compound before and/or after performing the conjugation.

Aspect 46: The method according to any of the foregoing aspects, wherein the one or more radionuclide comprise one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 47: The method according to any of the foregoing aspects, wherein the molecule is a 5T4 targeting agent, wherein the 5T4 targeting agent binds human 5T4.

Aspect 48: The method according to any of the foregoing aspects, wherein the 5T4 targeting agent is naptumomab estafenatox.

Aspect 49: The method according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or immunoglobulin light chain having complementarity determining regions 1-3 with amino acid sequences as set forth in SEQ ID NOS:119-121, respectively.

Aspect 50: The method according to any of the foregoing aspects, wherein the CD38 targeting agent is an antibody or an antibody fragment, comprising:
  an immunoglobulin heavy chain having the amino acid sequence as set forth in SEQ ID NO:124 and/or an immunoglobulin light chain having an amino acid sequence as set forth in SEQ ID NO:128;
  an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
  an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
  an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 51: The method according to any of the foregoing aspects, wherein the CD38 targeting agent is an antibody or an antibody fragment, comprising any of the amino acid sequences as set forth in SEQ ID NOS: 124-139.

Aspect 52: A method for manufacturing a chelator-conjugated molecule, comprising the steps:
  reacting a molecule comprising at least one free thiol group with a bifunctional chelator compound having a PODS reactive group according to any one of claims 7 through 23 to conjugate the bifunctional chelator compound to the molecule.

Aspect 53: The method of aspect 52, wherein the molecule comprises a peptide, a synthetic peptide, a protein, or a recombinant protein.

Aspect 54: The method according to any of the foregoing aspects, wherein the molecule comprises an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

Aspect 55: The method according to any of the foregoing aspects, wherein providing the molecule comprising at least one free thiol group further comprises reducing a disulfide bond to generate the at least one free thiol group of the molecule.

Aspect 56: The method according to any of the foregoing aspects, wherein the molecule comprises a peptide ligand of a receptor protein.

Aspect 57: The method according to any of the foregoing aspects, wherein the molecule is a CD38 targeting agent.

Aspect 58: The method according to any of the foregoing aspects, wherein the CD38 targeting agent is daratumumab.

Aspect 59: The method according to any of the foregoing aspects, wherein the CD38 targeting agent is an antibody or an antibody fragment, comprising:
  an immunoglobulin heavy chain having the amino acid sequence as set forth in SEQ ID NO:124 and/or an immunoglobulin light chain having an amino acid sequence as set forth in SEQ ID NO:128;
  an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
  an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
  an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 60: The method according to any of the foregoing aspects, further comprising the step of chelating one or more radionuclides to the chelator moiety of the bifunctional chelator compound before and/or after performing the conjugation.

Aspect 61: The method according to any of the foregoing aspects, wherein the one or more radionuclide comprise one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 62: The method according to any of the foregoing aspects, wherein the molecule is a 5T4 targeting agent, wherein the 5T4 targeting agent binds human 5T4.

Aspect 63: The method according to any of the foregoing aspects, wherein the 5T4 targeting agent is naptumomab estafenatox.

Aspect 64: The method according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or an immunoglobulin light chain having complementarity determining regions 1-3 with amino acid sequences as set forth in SEQ ID NOS:119-121, respectively.

Aspect 65: The method according to any of the foregoing aspects, wherein the CD38 targeting agent is an antibody or an antibody fragment, comprising any of the amino acid sequences as set forth in SEQ ID NOS: 124-139.

Aspect 66: A method for manufacturing a chelator-conjugated molecule, comprising the steps:
  reacting a molecule comprising at least one primary amine group with a bifunctional chelator compound having a NHS or SCN reactive group according to any one of claims 1 through 23 to conjugate the bifunctional chelator compound to the molecule; and
  reacting a molecule comprising at least one free thiol group with a bifunctional chelator compound having a PODS reactive group according to any one of claims 7 through 23 to conjugate the bifunctional chelator compound to the molecule.

Aspect 67: The method according to aspect 66, wherein the molecule comprises a peptide, a synthetic peptide, a protein, or a recombinant protein.

Aspect 68: The method according to any of the foregoing aspects, wherein the method comprises reacting the molecule comprising at least one free thiol group, the method further comprises reducing a disulfide bond to generate the at least one free thiol group of the molecule.

Aspect 69: The method according to any of the foregoing aspects, wherein the molecule comprises an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

Aspect 70: The method according to any of the foregoing aspects, wherein the molecule comprises a peptide ligand of a receptor protein.

Aspect 71: The method according to any of the foregoing aspects, wherein the molecule is a CD38 targeting agent.

Aspect 72: The method according to any of the foregoing aspects, wherein the CD38 targeting agent is daratumumab.

Aspect 73: The method according to any of the foregoing aspects, wherein the CD38 targeting agent is an antibody or an antibody fragment, comprising:
- an immunoglobulin heavy chain having the amino acid sequence as set forth in SEQ ID NO:124 and/or an immunoglobulin light chain having an amino acid sequence as set forth in SEQ ID NO:128;
- an immunoglobulin heavy chain having complementarity determining regions 1-3 with amino acid sequences as set forth in SEQ ID NOS:125-127, respectively, and/or an immunoglobulin light chain having complementarity determining regions 1-3 with amino acid sequences as set forth in SEQ ID NOS:129-131;
- an immunoglobulin heavy chain having the amino acid sequence as set forth in SEQ ID NO:124 and/or an immunoglobulin light chain having complementarity determining regions 1-3 with amino acid sequences as set forth in SEQ ID NOS:129-131; or
- an immunoglobulin light chain having an amino acid sequence as set forth in SEQ ID NO:128, and/or an immunoglobulin heavy chain having complementarity determining regions 1-3 with amino acid sequences as set forth in SEQ ID NOS:125-127, respectively.

Aspect 74: The method according to any of the foregoing aspects, further comprising the step of chelating one or more radionuclides to the chelator moiety of the bifunctional chelator compound before and/or after performing the conjugation.

Aspect 75: The method according to any of the foregoing aspects, wherein the one or more radionuclide comprise one or more of $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 76: The method according to any of the foregoing aspects, wherein the molecule is a 5T4 targeting agent, wherein the 5T4 targeting agent binds human 5T4.

Aspect 77: The method according to any of the foregoing aspects, wherein the 5T4 targeting agent is naptumomab estafenatox.

Aspect 78: The method according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or an immunoglobulin light chain having complementarity determining regions 1-3 with amino acid sequences as set forth in SEQ ID NOS:119-121, respectively.

Aspect 79: The method according to any of the foregoing aspects, wherein the CD38 targeting agent is an antibody or an antibody fragment, comprising any of the amino acid sequences as set forth in SEQ ID NOS: 124-139.

Aspect 80: A chelator-conjugated molecule prepared according to the method of any one of aspects 39-79.

Aspect 81: The chelator-conjugated molecule of aspect 80, wherein the molecule is a 5T4 targeting agent that binds human 5T4.

Aspect 82: The chelator-conjugated molecule according to any of the foregoing aspects, wherein the 5T4 targeting agent is naptumomab estafenatox.

Aspect 83: The chelator-conjugated molecule according to any of the foregoing aspects, wherein the molecule is a CD38 targeting agent.

Aspect 84: The chelator-conjugated molecule according to any of the foregoing aspects, wherein the 5T4 targeting agent is an antibody, an antibody fragment or an scFv molecule, comprising an immunoglobulin heavy chain having complementarity determining regions 1-3 with amino acid sequences as set forth in SEQ ID NOS:116-118, respectively, and/or an immunoglobulin light chain having complementarity determining regions 1-3 with amino acid sequences as set forth in SEQ ID NOS:119-121, respectively.

Aspect 85: A composition comprising:
- a quantity of a chelator-conjugated molecule according to any of the foregoing aspects;
- a quantity of a radionuclide;
- wherein the quantity of the chelator-conjugated molecule comprises a radiolabeled fraction, wherein the chelator moiety chelates the radionuclide and a non-radiolabeled fraction, and wherein the chelator moiety does not chelate any radionuclide.

Aspect 86: The composition of aspect 85, further comprising at least one excipient.

Aspect 87: The composition according to any of the foregoing aspects, wherein the radionuclide is selected from $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Au, $^{201}$Tl, $^{203}$Pb, $^{212}$Pb, $^{212}$Bi, $^{213}$Bi, $^{225}$Ac, $^{211}$At, and $^{227}$Th.

Aspect 88: A method of manufacturing a chelator-conjugated molecule according to Example 1.

Aspect 89: A method of synthesizing a bifunctional chelator compound according to Example 2, as shown in FIGS. 18-21.

EXAMPLES

Example 1: Preparation of a Radiolabeled Antibody

Preparing a chelator-conjugated antibody using an SCN (thiocyanate) reactive group bifunctional chelator: antibody conjugates are prepared by reacting a concentrated solution of monoclonal antibody with a SCN reactive group bifunctional chelator as disclosed herein in bicarbonate or in phosphate buffers at pH between about 8 and about 9 and by incubation at either about 37° C. or at room temperature. The molar ratio of antibody to bifunctional chelator is, for example, 1:10 or 1:20, or from 1:10 to 1:20. The conjugates are purified from excess of the bifunctional chelator by repeated filtration or centrifugation and by gravity size exclusion chromatography (SEC). During the purification process, the bicarbonate or phosphate buffer can be changed to N-2-Hydroxyethylpiperazine-N-2-ethanesulfonic acid (HEPES; Free Acid) or acetate medium. Conjugates are characterized by size exclusion high performance liquid chromatography (SE-HPLC).

Preparing a chelator-conjugated antibody using an NHS (NHS ester; N-hydroxysuccinimide ester) reactive group bifunctional chelator: The conjugation reaction between an antibody such as an IgG and an NHS ester reactive group bifunctional chelator is, for example, performed in 0.1 M NaHCO$_3$ buffer, pH 7.4, with 10- to 20-fold molar excess of bifunctional chelator to antibody, for 45 minutes to 1 hour, at room temperature/25° C. or 37° C. The conjugates are purified from excess of the bifunctional chelator by repeated filtration or centrifugation and by gravity size exclusion chromatography (SEC). During the purification process, the bicarbonate buffer can be changed to N-2-Hydroxyethylpiperazine-N-2-ethanesulfonic acid (HEPES; Free Acid) or acetate medium. Conjugates are characterized by size exclusion high performance liquid chromatography (SE-HPLC).

Preparing a chelator-conjugated antibody using a PODS (phenyloxadiazolyl methylsulfone) reactive group bifunctional chelator: A PODS reactive group bifunctional linker is conjugated to a monoclonal antibody, such as an IgG in the presence of TCEP, a mild reducing agent that reduces the inter-chain disulfide bonds within an immunoglobin to provide free thiols. The conjugation can be performed according to the methods set forth in U.S. Pat. No. 11,000,604.

In more detail, to a solution of 200 μg of antibody in PBS pH 7.4 (1 mg/mL) 1.33 μL of a fresh TCEP solution (10 mM in water, 10 eq.) is added concurrent with or followed by adding a suitable volume of a solution of a PODS reactive group bifunctional chelator (1 mM in DMSO). The reaction mixture is then stirred on a thermomixer (25° C. or 37° C.) for 30 min, 2 h, or 24 h. The resulting conjugate is then be purified on a size exclusion column (Sephadex G-25 M, PD-10 column, GE Healthcare; dead volume=2.5 mL, eluted with 2 mL of PBS, pH 7.4) and concentrated using centrifugal filtration units with a 50,000 Da molecular weight cut off (AMICON™ Ultra 4 Centrifugal Filtration Units, Millipore Corp., Billerica, MA, USA). The buffer in which the conjugate is dissolved can be changed to N-2-Hydroxyethylpiperazine-N-2-ethanesulfonic acid (HEPES; Free Acid) or acetate medium.

Radiolabeling the conjugate: A chelator-bearing conjugate is first prepared according to the aforementioned examples and then radiolabeled. Where the chelator moiety includes DOTA, DOTAGA or a DOTA derivative as exemplified herein, one radionuclide that is chelated is $^{225}$Ac.

An exemplary labeling reaction for $^{225}$Ac is as follows: A reaction including 15 μl 0.15M NH$_4$ Oac buffer, pH=6.5 and 2 μL (10 μg) chelator-conjugated antibody (5 mg/ml) is mixed in an Eppendorf reaction tube, and 4 μL $^{225}$Ac (10 μCi) in 0.05 M HCl subsequently added. The contents of the tube are mixed with a pipette tip and the reaction mixture incubated at 37° C. for 90 min with shaking at 100 rpm. At the end of the incubation period, 3 μL of a 1 mM DTPA solution is added to the reaction mixture and incubated at room temperature for 20 min to bind the unreacted $^{225}$Ac into the $^{225}$Ac-DTPA complex. Instant thin layer chromatography with 10 cm silica gel strip and 10 mM EDTA/normal saline mobile phase is used to determine the radiochemical purity of $^{225}$Ac-chelator-conjugated antibody through separating $^{225}$Ac-labeled antibody ($^{225}$Ac-chelator-conjugated antibody) from free $^{225}$Ac ($^{225}$Ac-DTPA). In this system, the radiolabeled antibody stays at the point of application and $^{225}$Ac-DTPA moves with the solvent front. The strips are cut in halves and counted in the gamma counter equipped with the multichannel analyzer using channels 72-110 for $^{225}$Ac to exclude its daughters.

Purification: An exemplary radiolabeled targeting agent, such as $^{225}$Ac-chelator-conjugated antibody, is purified either on PD10 columns pre-blocked with 1% I or on Vivaspin centrifugal concentrators with a 50 kDa MW cut-off with 2×1.5 mL washes, 3 min per spin. HPLC analyses of the $^{225}$Ac-chelator-conjugated antibody after purification is conducted using a Waters HPLC system equipped with flow-through Waters UV and Bioscan Radiation detectors, using a TSK3000SW XL column eluted with PBS at pH=7.4 and a flow rate of 1 ml/min.

With respect to any of the bifunctional chelator embodiments disclosed herein that include a cyclohexyl group adjacent to DOTA or a different chelator moiety, the invention also provides corresponding embodiments in which the cyclohexyl group is replaced by a benzyl group. Similarly, with respect to any of the bifunctional chelator embodiments disclosed herein that include a benzyl group adjacent to DOTA or a different chelator moiety, the invention also provides corresponding embodiments in which the benzyl group is replaced by a cyclohexyl group.

Example 2: Solid Phase Synthesis of Bifunctional Chelator Compounds

Synthesis of the Bifunctional Chelator Compound A With PEG3

Figure 19:
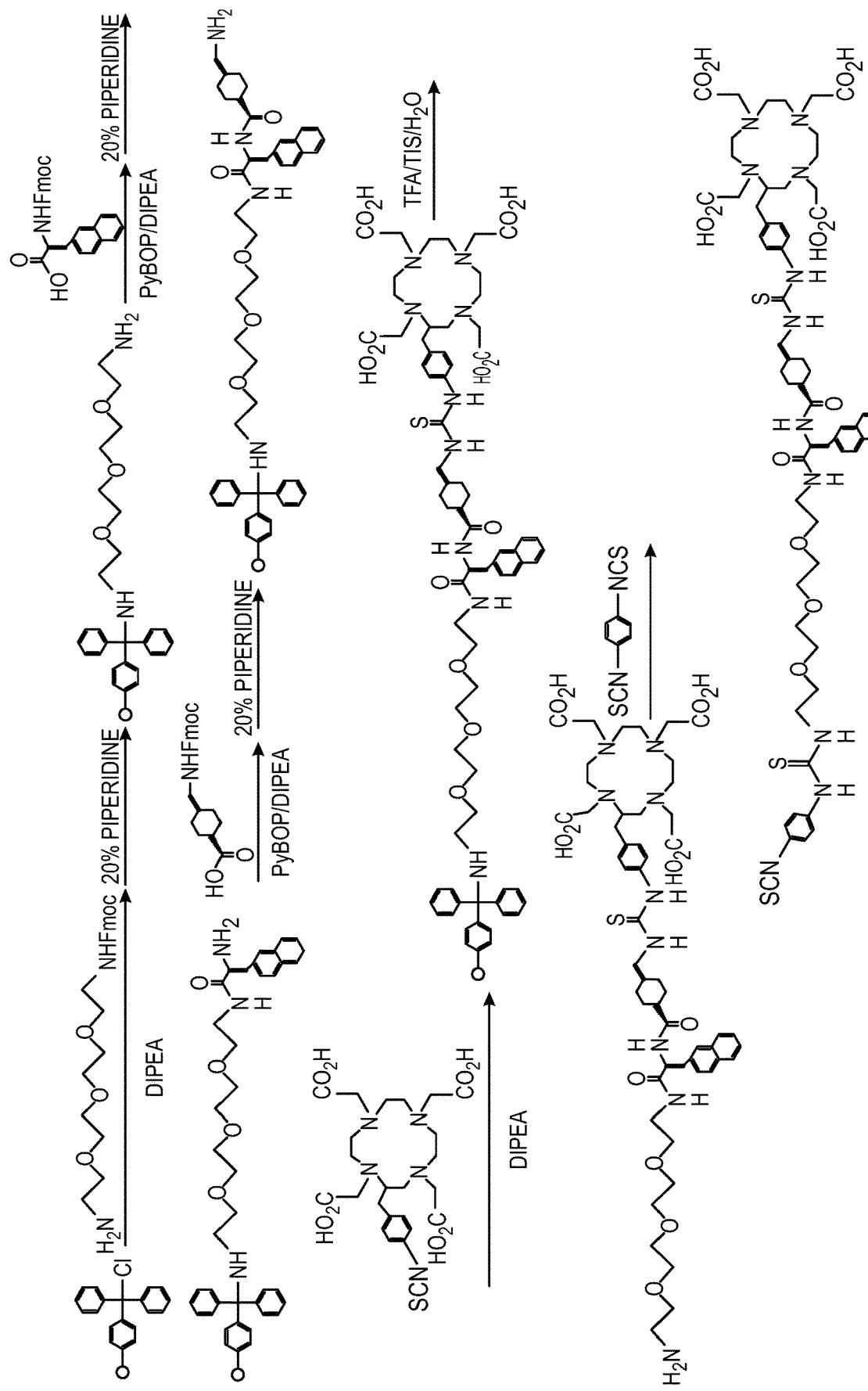
FIG. 19 shows a synthetic scheme of the present disclosure for the synthesis of a bifunctional chelator compound of Formula A shown in FIG. 1.

The synthesis was performed as shown in FIG. 19, wherein the starting materials and commercial sources thereof are described in Table 1.

TABLE 1

| Name | Structure | Supplier | Catalog No. |
|---|---|---|---|
| p-SCN-Bn-DOTA | [structure of p-SCN-Bn-DOTA] | Macrocyclics, Inc. (Plano, TX USA) | B-205 |

TABLE 1-continued

| Name | Structure | Supplier | Catalog No. |
|---|---|---|---|
| Trityl chloride resin | 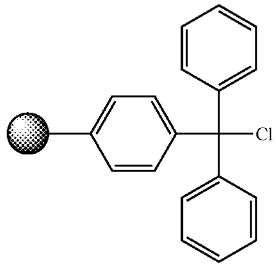 [SMILES: Cc1ccc(C(Cl)(c2ccccc2)c2ccccc2)cc1] | Chem-Impex Intl. Inc. (Wood Dale, IL USA) | 03902 |
| Fmoc-Amino-PEG3-Amine | 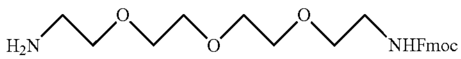 | Conju-Probe, LLC (San Diego, CA USA) | CP-1043 |
| Fmoc-3-(2-naphthyl)-alanine | 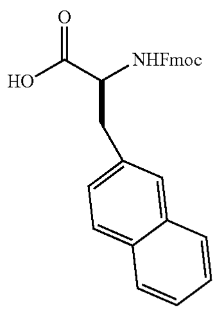 | Chem-Impex | 02588 |
| Fmoc-aminomethyl-cyclohexane carboxylic acid | 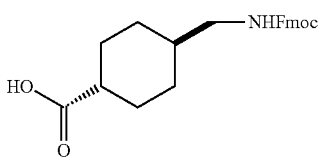 | Sigma-Aldrich (Burlington, MA USA; "Sigma") | 58446 |
| p-phenylene diisothiocyanate | 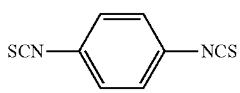 | Sigma | 258555 |

Synthesis of the Bifunctional Chelator Compound A

Figure 20:
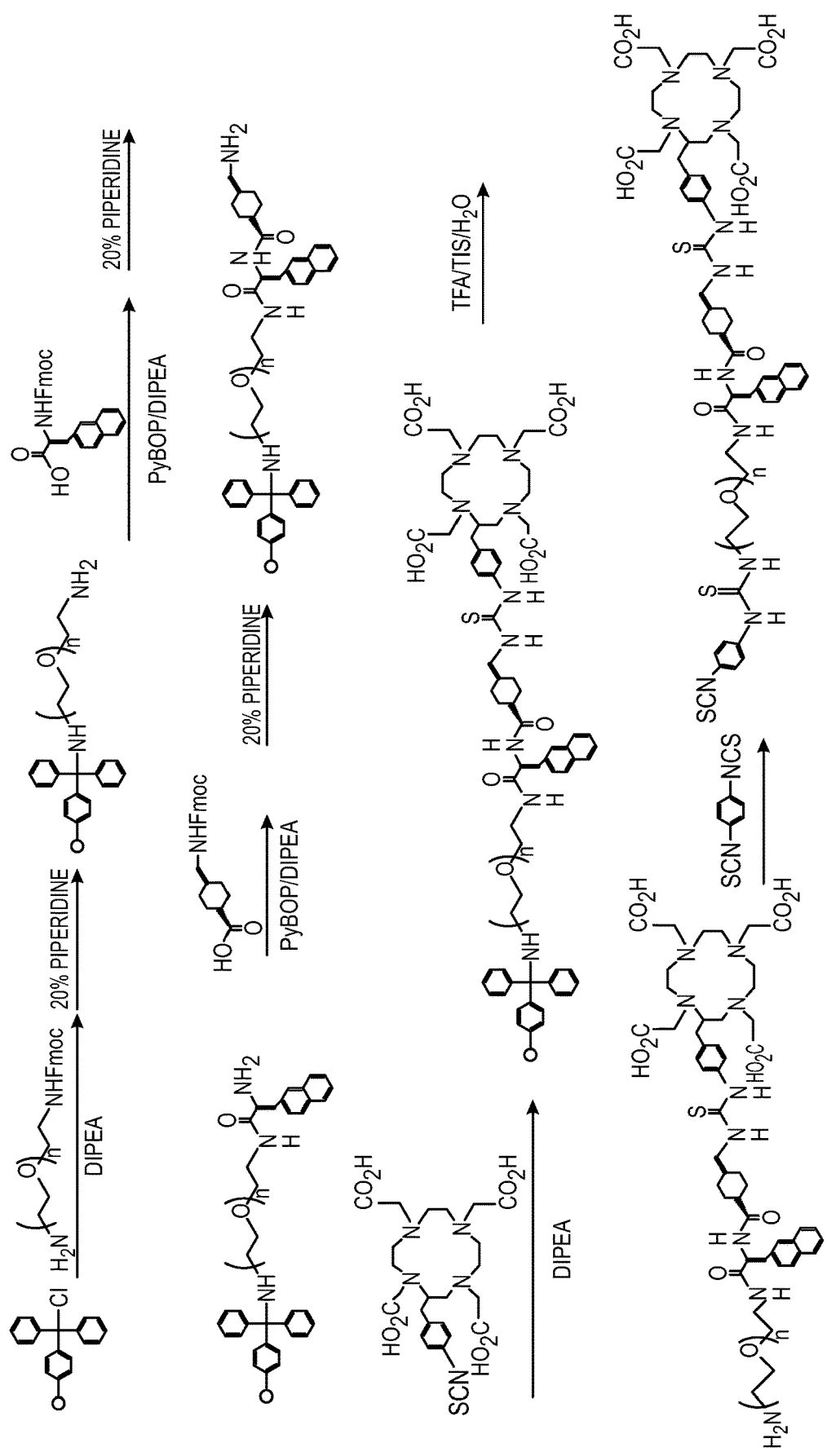
FIG. 20 shows a synthetic scheme of the present disclosure for the synthesis of a bifunctional chelator compound of Formula A shown in FIG. 1.

The synthesis was performed as shown in FIG. 20, wherein the starting materials are described in Table 2.

TABLE 2

| Name | Structure | Supplier | Catalog No. |
|---|---|---|---|
| p-SCN-Bn-DOTA | 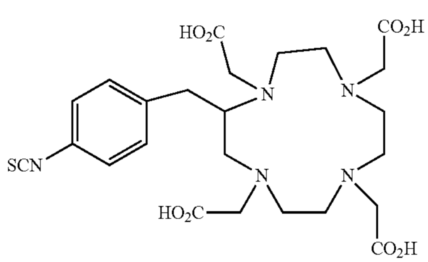 | Macrocyclics | B-205 |

TABLE 2-continued

| Name | Structure | Supplier | Catalog No. |
|---|---|---|---|
| Trityl chloride resin | 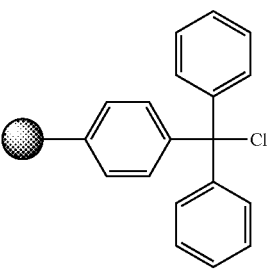 [SMILES: Cc1ccc(C(Cl)(c2ccccc2)c2ccccc2)cc1] | Chem-Impex | 03902 |
| Fmoc-NH-PEG-NH2, 10k | 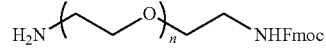 | BioPharma PEG Scientific Inc. (Watertown, MA USA) | HE069005-10K |
| Fmoc-3-(2-naphthyl)-alanine | 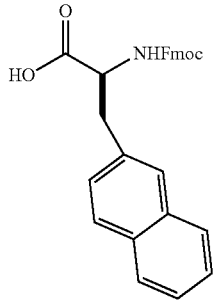 | Chem-Impex | 02588 |
| Fmoc-aminomethyl-cyclohexane carboxylic acid | 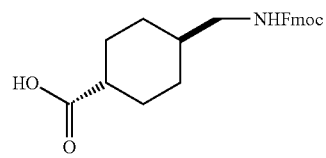 | Sigma | 58446 |
| p-phenylene diisothiocyanate | 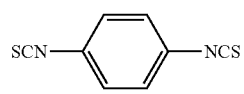 | Sigma | 258555 |

Synthesis of the Bifunctional Chelator Compound B

Figure 21:
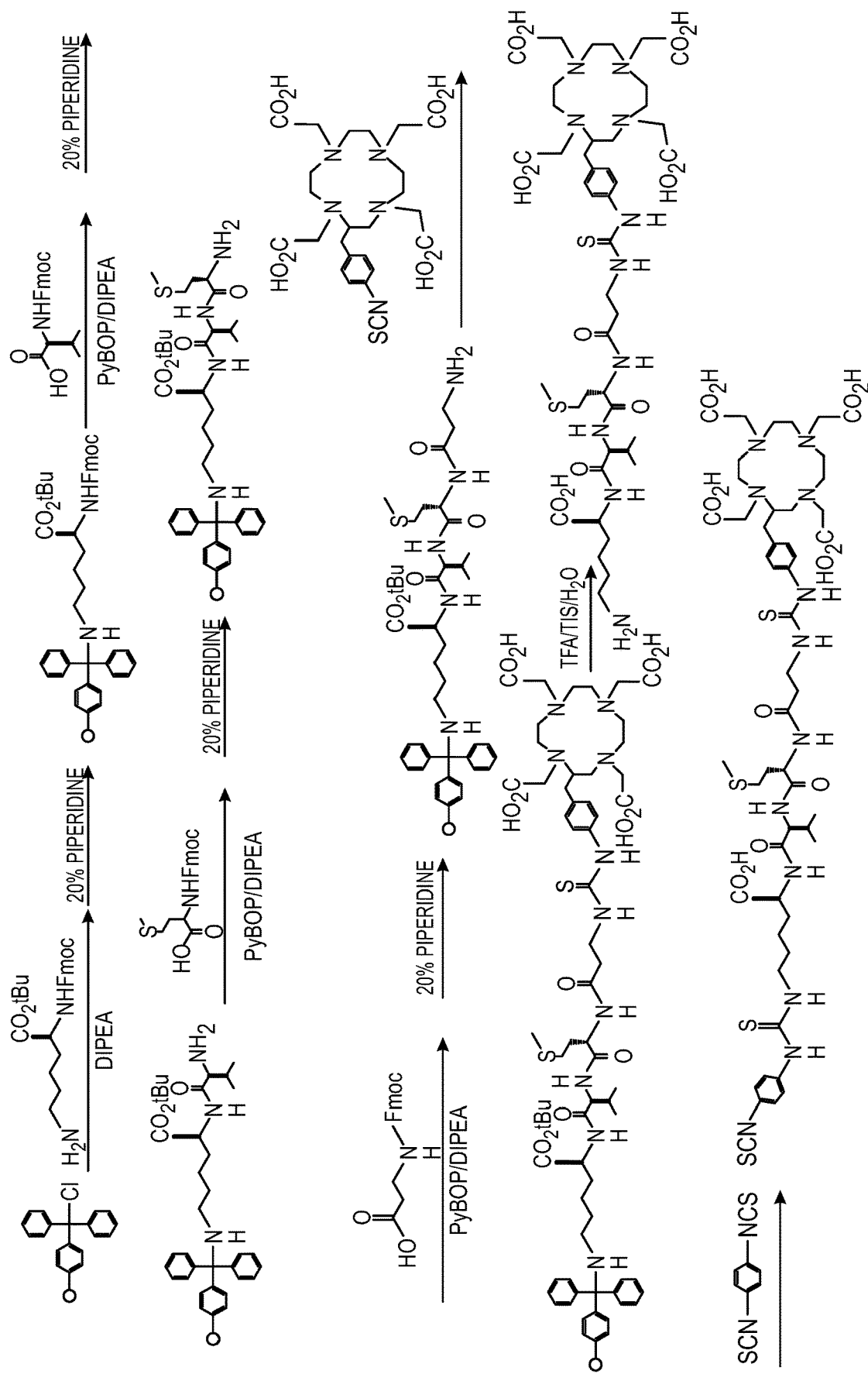
FIG. 21 shows a synthetic scheme of the present disclosure for the synthesis of a bifunctional chelator compound of Formula B shown in FIG. 2.

The synthesis was performed as shown in FIG. 21, wherein the starting materials are described in Table 3.

TABLE 3

| Name | Structure | Supplier | Catalog No. |
|---|---|---|---|
| Trityl chloride resin | 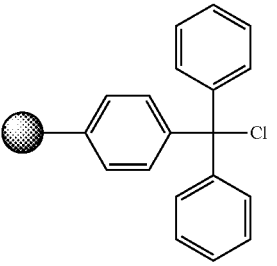 [SMILES: Cc1ccc(C(Cl)(c2ccccc2)c2ccccc2)cc1] | Chem-Impex | 03902 |

TABLE 3-continued

| Name | Structure | Supplier | Catalog No. |
|---|---|---|---|
| p-SCN-Bn-DOTA | 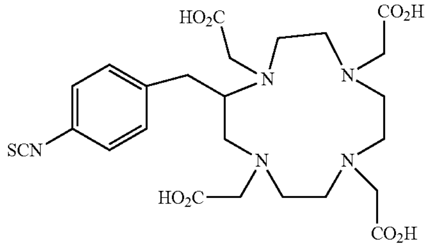 | Macrocyclics | B-205 |
| Fmoc-Lys-OtBu | 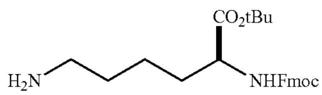 | Chem-Impex | 33496 |
| Fmoc-Val-OH | 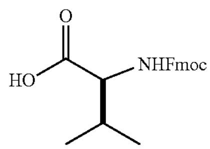 | Sigma | 47638 |
| Fmoc-Met-OH | 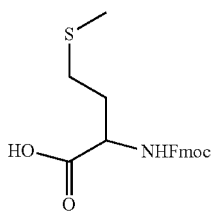 | Sigma | 47634 |
| Fmoc-beta-Ala-OH | 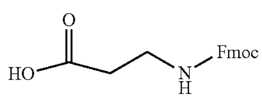 | Sigma | 47587 |
| p-phenylene diisothiocyanate | 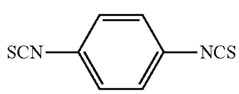 | Sigma | 258555 |

Synthesis of the Bifunctional Chelator Compound C

Figure 18:
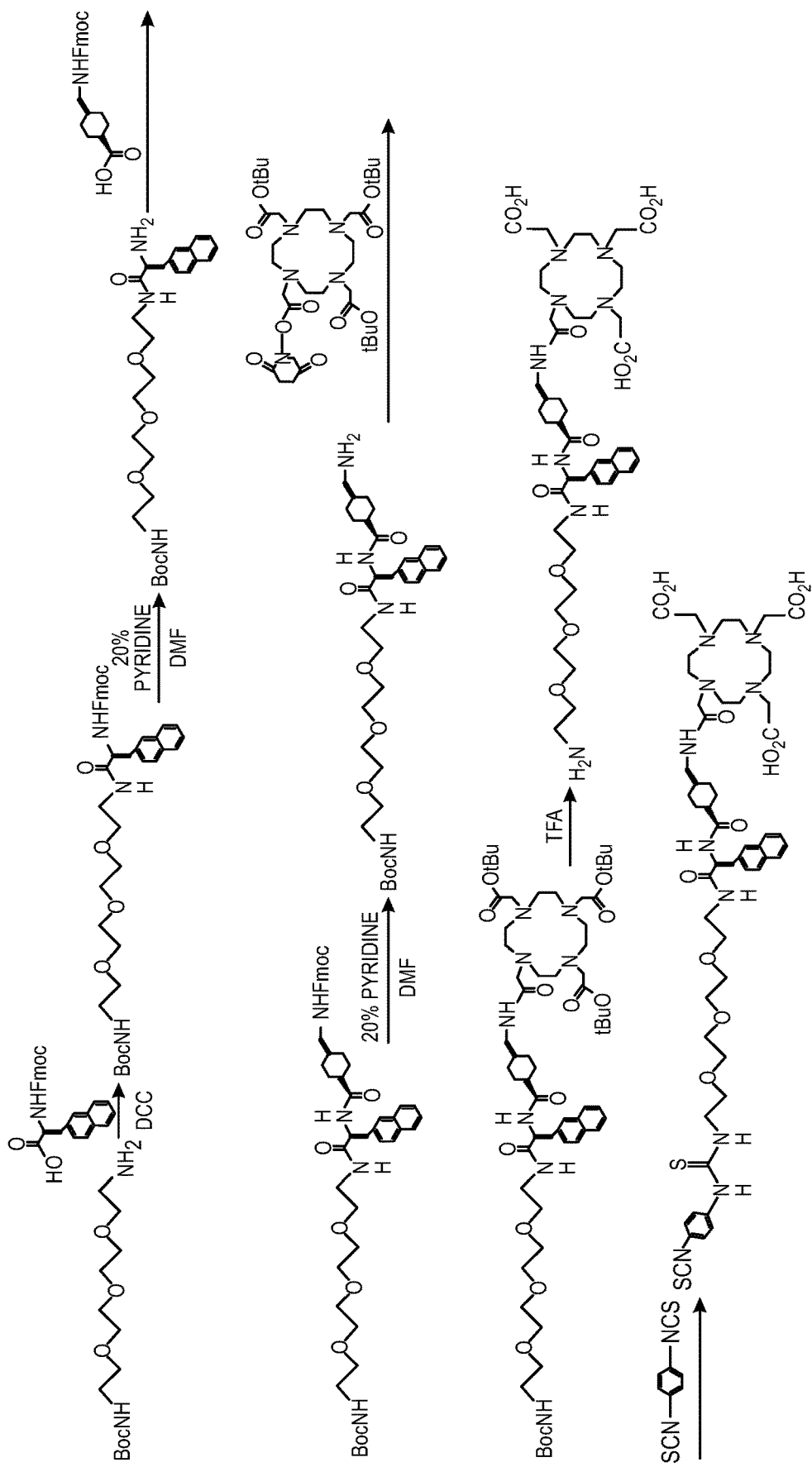
FIG. 18 shows a synthetic scheme of the present disclosure for the synthesis of the bifunctional chelator compound of Formula C shown in FIG. 3.

The synthesis was performed as shown in FIG. 18.

```
                        SEQUENCE LISTING

Sequence total quantity: 139
SEQ ID NO: 1            moltype = AA   length = 11
FEATURE                 Location/Qualifiers
REGION                  1..11
                        note = Antibody component sequence
source                  1..11
                        mol_type = protein
                        organism = synthetic construct
SEQUENCE: 1
SASQDISNYL N                                                             11

SEQ ID NO: 2            moltype = AA   length = 7
FEATURE                 Location/Qualifiers
REGION                  1..7
                        note = Antibody component sequence
source                  1..7
                        mol_type = protein
                        organism = synthetic construct
SEQUENCE: 2
DTSILHL                                                                   7
```

```
SEQ ID NO: 3              moltype = AA   length = 9
FEATURE                   Location/Qualifiers
REGION                    1..9
                          note = Antibody component sequence
source                    1..9
                          mol_type = protein
                          organism = synthetic construct
SEQUENCE: 3
QQYSKFPRT                                                                  9

SEQ ID NO: 4              moltype = AA   length = 5
FEATURE                   Location/Qualifiers
REGION                    1..5
                          note = Antibody component sequence
source                    1..5
                          mol_type = protein
                          organism = synthetic construct
SEQUENCE: 4
NYAMN                                                                      5

SEQ ID NO: 5              moltype = AA   length = 17
FEATURE                   Location/Qualifiers
REGION                    1..17
                          note = Antibody component sequence
source                    1..17
                          mol_type = protein
                          organism = synthetic construct
SEQUENCE: 5
WINTHTGDPT YADDFKG                                                        17

SEQ ID NO: 6              moltype = AA   length = 9
FEATURE                   Location/Qualifiers
REGION                    1..9
                          note = Antibody component sequence
source                    1..9
                          mol_type = protein
                          organism = synthetic construct
SEQUENCE: 6
TYGNYAMDY                                                                  9

SEQ ID NO: 7              moltype = AA   length = 107
FEATURE                   Location/Qualifiers
REGION                    1..107
                          note = Antibody component sequence
source                    1..107
                          mol_type = protein
                          organism = synthetic construct
SEQUENCE: 7
DIQMTQTTSS LSASLGDRVT ISCSASQDIS NYLNWYQQKP DGTVKLLIYD TSILHLGVPS          60
RFSGSGSGTD YSLTISNLEP EDIATYYCQQ YSKFPRTFGG GTTLEIK                      107

SEQ ID NO: 8              moltype = AA   length = 191
FEATURE                   Location/Qualifiers
REGION                    1..191
                          note = Antibody component sequence
source                    1..191
                          mol_type = protein
                          organism = synthetic construct
SEQUENCE: 8
QIQLVQSGPE LKKPGETVKV SCKASGYMFT NYAMNWVKQA PEKGLKWMGW INTHTGDPTY          60
ADDFKGRIAF SLETSASTAY LQINNLKNED TATYFCVRTY GNYAMDYWGQ GTSVTVSSAK         120
TTAPSVYPLA PVCGDTTGSS VTLGCLVKGY FPEPVTLTWN SGSLSSGVHT FPAVLQSDLY         180
TLSSSVTVTS S                                                             191

SEQ ID NO: 9              moltype = AA   length = 109
FEATURE                   Location/Qualifiers
REGION                    1..109
                          note = Antibody component sequence
source                    1..109
                          mol_type = protein
                          organism = synthetic construct
SEQUENCE: 9
DIQLTQSPSF LSASVGDRVT ITCRASQGIT SYLAWYQQKP GKAPKLLIYA ASALQSGVPS          60
RFSGRGSGTE FTLTISSLQP EDFATYYCQQ VNRGAAITFG HGTRLDIKR                    109

SEQ ID NO: 10             moltype = AA   length = 120
FEATURE                   Location/Qualifiers
REGION                    1..120
```

```
                          note = Antibody component sequence
VARIANT                   20
                          note = misc_feature - Xaa can be any naturally occurring
                           amino acid
VARIANT                   35
                          note = misc_feature - Xaa can be any naturally occurring
                           amino acid
source                    1..120
                          mol_type = protein
                          organism = synthetic construct
SEQUENCE: 10
QVQLVQSGAE VKKPGSSVRX SCRASGGSST TYAFXWVRQA PGQGLEWMGG IVPIFGTLKY    60
AQKFQDRVTL TADKSTGTAY MELNSLRLDD TAVYYCARAI QLEGRPFDHW GQGTQVTVSA   120

SEQ ID NO: 11             moltype = AA   length = 11
FEATURE                   Location/Qualifiers
REGION                    1..11
                          note = Antibody component sequence
source                    1..11
                          mol_type = protein
                          organism = synthetic construct
SEQUENCE: 11
QASQDIGNNL I                                                         11

SEQ ID NO: 12             moltype = AA   length = 7
FEATURE                   Location/Qualifiers
REGION                    1..7
                          note = Antibody component sequence
source                    1..7
                          mol_type = protein
                          organism = synthetic construct
SEQUENCE: 12
YATNLAN                                                               7

SEQ ID NO: 13             moltype = AA   length = 7
FEATURE                   Location/Qualifiers
REGION                    1..7
                          note = Antibody component sequence
source                    1..7
                          mol_type = protein
                          organism = synthetic construct
SEQUENCE: 13
QQWSSNP                                                               7

SEQ ID NO: 14             moltype = AA   length = 5
FEATURE                   Location/Qualifiers
REGION                    1..5
                          note = Antibody component sequence
source                    1..5
                          mol_type = protein
                          organism = synthetic construct
SEQUENCE: 14
NYYMS                                                                 5

SEQ ID NO: 15             moltype = AA   length = 17
FEATURE                   Location/Qualifiers
REGION                    1..17
                          note = Antibody component sequence
source                    1..17
                          mol_type = protein
                          organism = synthetic construct
SEQUENCE: 15
NIYGGNGGTG YNQKFKG                                                   17

SEQ ID NO: 16             moltype = AA   length = 8
FEATURE                   Location/Qualifiers
REGION                    1..8
                          note = Antibody component sequence
source                    1..8
                          mol_type = protein
                          organism = synthetic construct
SEQUENCE: 16
GDLYAMDY                                                              8

SEQ ID NO: 17             moltype = AA   length = 98
FEATURE                   Location/Qualifiers
REGION                    1..98
                          note = Antibody component sequence
source                    1..98
```

```
                              mol_type = protein
                              organism = synthetic construct
SEQUENCE: 17
VLTQSPSSMS ASLGDRVTIT CQASQDIGNN LIWFQQKPGK SPRPMIYYAT NLANGVPSRF      60
SGSGSGTSYS LTISSMEAED AATYYCQQWS SNPYTFGG                              98

SEQ ID NO: 18                 moltype = AA    length = 106
FEATURE                       Location/Qualifiers
REGION                        1..106
                              note = Antibody component sequence
source                        1..106
                              mol_type = protein
                              organism = synthetic construct
SEQUENCE: 18
AELVKPGASV KLSCKTSGYT FSNYYMSWLK QMPGQNIEWI GNIYGGNGGT GYNQKFKGKA      60
TLTVDKSSST AYMQLSSLTS EDSAVYFCAR GDLYAMDYWG QGTTVT                    106

SEQ ID NO: 19                 moltype = AA    length = 245
FEATURE                       Location/Qualifiers
REGION                        1..245
                              note = Antibody component sequence
source                        1..245
                              mol_type = protein
                              organism = synthetic construct
SEQUENCE: 19
MAQVQLQQSG AELVKPGASV KLSCKTSGYT FSNYYMSWLK QMPGQNIEWI GNIYGGNGGT      60
GYNQKFKGKA TLTVDKSSST AYMQLSSLTS EDSAVYFCAR GDLYAMDYWG QGTTVTVSSG     120
GGGSGGGGSG GGGSDIVLTQ SPSSMSASLG DRVTITCQAS QDIGNNLIWF QQKPGKSPRP     180
MIYYATNLAN GVPSRFSGSG SGTSYSLTIS SMEAEDAATY YCQQWSSNPY TFGGGTKLEI     240
KRAAA                                                                 245

SEQ ID NO: 20                 moltype = AA    length = 11
FEATURE                       Location/Qualifiers
REGION                        1..11
                              note = Antibody component sequence
source                        1..11
                              mol_type = protein
                              organism = synthetic construct
SEQUENCE: 20
RASQNIDTSI H                                                           11

SEQ ID NO: 21                 moltype = AA    length = 7
FEATURE                       Location/Qualifiers
REGION                        1..7
                              note = Antibody component sequence
source                        1..7
                              mol_type = protein
                              organism = synthetic construct
SEQUENCE: 21
YASESIS                                                                 7

SEQ ID NO: 22                 moltype = AA    length = 9
FEATURE                       Location/Qualifiers
REGION                        1..9
                              note = Antibody component sequence
source                        1..9
                              mol_type = protein
                              organism = synthetic construct
SEQUENCE: 22
QQSNYWPLT                                                               9

SEQ ID NO: 23                 moltype = AA    length = 5
FEATURE                       Location/Qualifiers
REGION                        1..5
                              note = Antibody component sequence
source                        1..5
                              mol_type = protein
                              organism = synthetic construct
SEQUENCE: 23
SYWMN                                                                   5

SEQ ID NO: 24                 moltype = AA    length = 6
FEATURE                       Location/Qualifiers
REGION                        1..6
                              note = Antibody component sequence
source                        1..6
                              mol_type = protein
                              organism = synthetic construct
SEQUENCE: 24
```

```
GYSFTS                                                                          6

SEQ ID NO: 25           moltype = AA  length = 10
FEATURE                 Location/Qualifiers
REGION                  1..10
                        note = Antibody component sequence
source                  1..10
                        mol_type = protein
                        organism = synthetic construct
SEQUENCE: 25
GYSFTSYWMN                                                                     10

SEQ ID NO: 26           moltype = AA  length = 17
FEATURE                 Location/Qualifiers
REGION                  1..17
                        note = Antibody component sequence
source                  1..17
                        mol_type = protein
                        organism = synthetic construct
SEQUENCE: 26
MIHPSDSETR LNQKFKD                                                             17

SEQ ID NO: 27           moltype = AA  length = 10
FEATURE                 Location/Qualifiers
REGION                  1..10
                        note = Antibody component sequence
source                  1..10
                        mol_type = protein
                        organism = synthetic construct
SEQUENCE: 27
MIHPSDSETR                                                                     10

SEQ ID NO: 28           moltype = AA  length = 9
FEATURE                 Location/Qualifiers
REGION                  1..9
                        note = Antibody component sequence
source                  1..9
                        mol_type = protein
                        organism = synthetic construct
SEQUENCE: 28
EMGPYTLDY                                                                       9

SEQ ID NO: 29           moltype = AA  length = 127
FEATURE                 Location/Qualifiers
REGION                  1..127
                        note = Antibody component sequence
source                  1..127
                        mol_type = protein
                        organism = synthetic construct
SEQUENCE: 29
MSVPTQVLGL LLLWLTDARC DILLTQSPAI LSVSPGARVS FSCRASQNID TSIHWYQQRT               60
NGSPRLLIKY ASESISGIPS RFSGSGSGTD FTLSINSVES EDIADYYCQQ SNYWPLTFGA              120
GTKLELK                                                                       127

SEQ ID NO: 30           moltype = AA  length = 141
FEATURE                 Location/Qualifiers
REGION                  1..141
                        note = Antibody component sequence
source                  1..141
                        mol_type = protein
                        organism = synthetic construct
SEQUENCE: 30
MEWSWVFLFF LSVTTGVHSQ VQLQQPGAEL VRPGASVKLS CKASGYSFTS YWMNWMKQRP               60
GQGLEWIGMI HPSDSETRLN QKFKDKATLT VDKSSSTAYM QLNSPTSEDS AVYYCAREMG              120
PYTLDYWGQG TSVTVSSAST K                                                       141

SEQ ID NO: 31           moltype = AA  length = 16
FEATURE                 Location/Qualifiers
REGION                  1..16
                        note = Antibody component sequence
source                  1..16
                        mol_type = protein
                        organism = synthetic construct
SEQUENCE: 31
KSSQSLLNSS NQKNYL                                                              16

SEQ ID NO: 32           moltype = AA  length = 7
FEATURE                 Location/Qualifiers
REGION                  1..7
```

```
                            note = Antibody component sequence
source                      1..7
                            mol_type = protein
                            organism = synthetic construct
SEQUENCE: 32
FASTRES                                                                 7

SEQ ID NO: 33               moltype = AA  length = 9
FEATURE                     Location/Qualifiers
REGION                      1..9
                            note = Antibody component sequence
source                      1..9
                            mol_type = protein
                            organism = synthetic construct
SEQUENCE: 33
QQHYSTPPT                                                               9

SEQ ID NO: 34               moltype = AA  length = 5
FEATURE                     Location/Qualifiers
REGION                      1..5
                            note = Antibody component sequence
source                      1..5
                            mol_type = protein
                            organism = synthetic construct
SEQUENCE: 34
RYAMS                                                                   5

SEQ ID NO: 35               moltype = AA  length = 6
FEATURE                     Location/Qualifiers
REGION                      1..6
                            note = Antibody component sequence
source                      1..6
                            mol_type = protein
                            organism = synthetic construct
SEQUENCE: 35
GFTFSR                                                                  6

SEQ ID NO: 36               moltype = AA  length = 10
FEATURE                     Location/Qualifiers
REGION                      1..10
                            note = Antibody component sequence
source                      1..10
                            mol_type = protein
                            organism = synthetic construct
SEQUENCE: 36
GFTFSRYAMS                                                             10

SEQ ID NO: 37               moltype = AA  length = 15
FEATURE                     Location/Qualifiers
REGION                      1..15
                            note = Antibody component sequence
source                      1..15
                            mol_type = protein
                            organism = synthetic construct
SEQUENCE: 37
TIFSGGSYTY YPDSV                                                       15

SEQ ID NO: 38               moltype = AA  length = 8
FEATURE                     Location/Qualifiers
REGION                      1..8
                            note = Antibody component sequence
source                      1..8
                            mol_type = protein
                            organism = synthetic construct
SEQUENCE: 38
TIFSGGSY                                                                8

SEQ ID NO: 39               moltype = AA  length = 9
FEATURE                     Location/Qualifiers
REGION                      1..9
                            note = Antibody component sequence
source                      1..9
                            mol_type = protein
                            organism = synthetic construct
SEQUENCE: 39
PNWERTFDY                                                               9

SEQ ID NO: 40               moltype = AA  length = 133
FEATURE                     Location/Qualifiers
```

| | | |
|---|---|---|
| REGION | 1..133 | |
| | note = Antibody component sequence | |
| source | 1..133 | |
| | mol_type = protein | |
| | organism = synthetic construct | |

SEQUENCE: 40
```
MESQTQVLMF LLLWVSGACT DIVMTQSPSS LAMSVGQKVT MSCKSSQSLL NSSNQKNYLA    60
WYQQKPGQSP KLLVYFASTR ESGVPDRFMG SGSGTDFTLT ISSVQAEDLA DYFCQQHYST   120
PPTFGGGTKL EIK                                                     133
```

| | | |
|---|---|---|
| SEQ ID NO: 41 | moltype = AA   length = 133 | |
| FEATURE | Location/Qualifiers | |
| REGION | 1..133 | |
| | note = Antibody component sequence | |
| source | 1..133 | |
| | mol_type = protein | |
| | organism = synthetic construct | |

SEQUENCE: 41
```
MRVLILLWLF TAFPGLLSDV QLQESGPGLV KPSQSLSLTC TVTGYSITSD YAWNWIRQFP    60
GNKLEWMGFV SYSGTTKYNP SLKSRISITR DTSENQFFLQ LNSVTSEDTA TYYCARGYGF   120
DYWGQGTTLT VSS                                                     133
```

| | | |
|---|---|---|
| SEQ ID NO: 42 | moltype = AA   length = 38 | |
| FEATURE | Location/Qualifiers | |
| REGION | 1..38 | |
| | note = Antibody component sequence | |
| source | 1..38 | |
| | mol_type = protein | |
| | organism = synthetic construct | |

SEQUENCE: 42
```
EIILTQSPTT MAASPGEKIT ITCSASSSIS SHYLHWYQ                            38
```

| | | |
|---|---|---|
| SEQ ID NO: 43 | moltype = AA   length = 40 | |
| FEATURE | Location/Qualifiers | |
| REGION | 1..40 | |
| | note = Antibody component sequence | |
| source | 1..40 | |
| | mol_type = protein | |
| | organism = synthetic construct | |

SEQUENCE: 43
```
QKSGFSPKLL YRTSNLASGV PARESGSGSG TSYSLTIGTM                          40
```

| | | |
|---|---|---|
| SEQ ID NO: 44 | moltype = AA   length = 29 | |
| FEATURE | Location/Qualifiers | |
| REGION | 1..29 | |
| | note = Antibody component sequence | |
| source | 1..29 | |
| | mol_type = protein | |
| | organism = synthetic construct | |

SEQUENCE: 44
```
EAEDVATYYC QQGSSLPLTF GAGTKVEIK                                      29
```

| | | |
|---|---|---|
| SEQ ID NO: 45 | moltype = AA   length = 41 | |
| FEATURE | Location/Qualifiers | |
| REGION | 1..41 | |
| | note = Antibody component sequence | |
| source | 1..41 | |
| | mol_type = protein | |
| | organism = synthetic construct | |

SEQUENCE: 45
```
EIQLQQSGPE LVKPGASVKV SCKASGYAFT SQNIYWVKQS H                        41
```

| | | |
|---|---|---|
| SEQ ID NO: 46 | moltype = AA   length = 40 | |
| FEATURE | Location/Qualifiers | |
| REGION | 1..40 | |
| | note = Antibody component sequence | |
| source | 1..40 | |
| | mol_type = protein | |
| | organism = synthetic construct | |

SEQUENCE: 46
```
GKSLEWIGYE PYNVVPMYNP KFKGKATLTV DKSSSSAYIH                          40
```

| | | |
|---|---|---|
| SEQ ID NO: 47 | moltype = AA   length = 35 | |
| FEATURE | Location/Qualifiers | |
| REGION | 1..35 | |
| | note = Antibody component sequence | |
| source | 1..35 | |
| | mol_type = protein | |
| | organism = synthetic construct | |

```
SEQUENCE: 47
LNSLTSEDSA IYYCARSGSS NFDYWGQGTT LTVSS                                    35

SEQ ID NO: 48           moltype = AA  length = 330
FEATURE                 Location/Qualifiers
source                  1..330
                        mol_type = protein
                        organism = Homo sapiens
SEQUENCE: 48
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKKVEP KSCDKTHTCP PCPAPELLGG         120
PSVFLFPPKP KDTLMISRTP EVTCVVVDVS HEDPEVKFNW YVDGVEVHNA KTKPREEQYN         180
STYRVVSVLT VLHQDWLNGK EYKCKVSNKA LPAPIEKTIS KAKGQPREPQ VYTLPPSRDE         240
LTKNQVSLTC LVKGFYPSDI AVEWESNGQP ENNYKTTPPV LDSDGSFFLY SKLTVDKSRW         300
QQGNVFSCSV MHEALHNHYT QKSLSLSPGK                                         330

SEQ ID NO: 49           moltype = AA  length = 216
FEATURE                 Location/Qualifiers
source                  1..216
                        mol_type = protein
                        organism = Homo sapiens
SEQUENCE: 49
MGWIRGRRSR HSWEMSEFHN YNLDLKKSDF STRWQKQRCP VVSKCRENA SPFFFCCFIA           60
VAMGIRPFIIM VTIWSAVFLN SLFNQEVQIP LTESYCGPCP KNWICYKNNC YQFFDESKNW        120
YESQASCMSQ NASLLKVYSK EDQDLLKLVK SYHWMGLVHI PTNGSWQWED GSILSPNLLT         180
IIEMQKGDCA LYASSFKGYI ENCSTPNTYI CMQRTV                                  216

SEQ ID NO: 50           moltype = AA  length = 4
FEATURE                 Location/Qualifiers
REGION                  1..4
                        note = fusion protein linker sequence
source                  1..4
                        mol_type = protein
                        organism = synthetic construct
SEQUENCE: 50
IEGR                                                                       4

SEQ ID NO: 51           moltype =     length =
SEQUENCE: 51
000

SEQ ID NO: 52           moltype = AA  length = 345
FEATURE                 Location/Qualifiers
REGION                  1..345
                        note = Fusion protein
source                  1..345
                        mol_type = protein
                        organism = synthetic construct
SEQUENCE: 52
EEELQVIQPD KSVSVAAGES AILHCTVTSL IPVGPIQWFR GAGPARELIY NQKEGHFPRV          60
TTVSESTKRE NMDFSISISN ITPADAGTYY CVKFRKGSPD TEFKSGAGTE LSVRAKPSDK         120
THTCPPCPAP ELLGGPSVFL FPPKPKDTLM ISRTPEVTCV VVDVSHEDPE VKFNWYVDGV         180
EVHNAKTKPR EEQYNSTYRV VSVLTVLHQD WLNGKEYKCK VSNKALPAPI EKTISKAKGQ         240
PREPQVYTLP PSRDELTKNQ VSLTCLVKGF YPSDIAVEWE SNGQPENNYK TTPPVLDSDG         300
SFFLYSKLTV DKSRWQQGNV FSCSVMHEAL HNHYTQKSLS LSPGK                        345

SEQ ID NO: 53           moltype = AA  length = 345
FEATURE                 Location/Qualifiers
REGION                  1..345
                        note = Fusion protein
source                  1..345
                        mol_type = protein
                        organism = synthetic construct
SEQUENCE: 53
EEELQVIQPD KSVSVAAGES AILHCTVTSL IPVGPIQWFR GAGPARELIY NQKEGHFPRV          60
TTVSESTKRE NMDFSISISN ITPADAGTYY CVKFRKGSPD TEFKSGAGTE LSVRAKPSDK         120
THTCPPCPAP ELLGGPSVFL FPPKPKDTLM ISRTPEVTCV VVDVSHEDPE VKFNWYVDGV         180
EVHNAKTKPR EEQYNSTYRV VSVLTVLHQD WLNGKEYKCK VSNKALPAPI EKTISKAKGQ         240
PREPQVYTLP PSRDELTKNQ VSLTCLVKGF YPSDIAVEWE SNGQPENNYK TTPPVLDSDG         300
SFFLYSKLTV DKSRWQQGNV FSCSVMHEAL HNHYTQKSLS LSPGK                        345

SEQ ID NO: 54           moltype = AA  length = 347
FEATURE                 Location/Qualifiers
REGION                  1..347
                        note = Fusion protein
source                  1..347
                        mol_type = protein
                        organism = synthetic construct
SEQUENCE: 54
```

```
EEELQVIQPD KSVSVAAGES AILHCTVTSL IPVGPIQWFR GAGPARELIY NQKEGHFPRV    60
TTVSESTKRE NMDFSISISN ITPADAGTYY CVKFRKGSPD TEFKSGAGTE LSVRAKPSES   120
KYGPPCPPCP APEFLGGPSV FLFPPKPKDT LMISRTPEVT CVVVDVSQED PEVQFNWYVD   180
GVEVHNAKTK PREEQFNSTY RVVSVLTVLH QDWLNGKEYK CKVSNKGLPS SIEKTISKAK   240
GQPREPQVYT LPPSQEEMTK NQVSLTCLVK GFYPSDIAVE WESNGQPENN YKTTPPVLDS   300
DGSFFLYSRL TVDKSRWQEG NVFSCSVMHE ALHNHYTQKS LSLSLGK                347

SEQ ID NO: 55           moltype = DNA  length = 25
FEATURE                 Location/Qualifiers
misc_feature            1..25
                        note = Morpholino
source                  1..25
                        mol_type = other DNA
                        organism = synthetic construct
SEQUENCE: 55
cgtcacaggc aggacccact gccca                                          25

SEQ ID NO: 56           moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 56
DYAMS                                                                 5

SEQ ID NO: 57           moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 57
TISDGGTYTY YPDSVKG                                                   17

SEQ ID NO: 58           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 58
EWGDYDGFDY                                                           10

SEQ ID NO: 59           moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 59
RASQEISGYL S                                                         11

SEQ ID NO: 60           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 60
AASTLDS                                                               7

SEQ ID NO: 61           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 61
LQYDSYPYT                                                             9

SEQ ID NO: 62           moltype = AA   length = 119
FEATURE                 Location/Qualifiers
```

```
REGION                          1..119
                                note = Description of Artificial Sequence: Synthetic
                                  polypeptide
source                          1..119
                                mol_type = protein
                                organism = synthetic construct
SEQUENCE: 62
QVQLVESGGG LVKPGGSLRL SCAASGFTFS DYAMSWIRQA PGKGLEWVST ISDGGTYTYY    60
PDSVKGRFTI SRDNAKNSLY LQMNSLRAED TAVYYCAREW GDYDGFDYWG QGTLVTVSS    119

SEQ ID NO: 63                   moltype = AA  length = 107
FEATURE                         Location/Qualifiers
REGION                          1..107
                                note = Description of Artificial Sequence: Synthetic
                                  polypeptide
source                          1..107
                                mol_type = protein
                                organism = synthetic construct
SEQUENCE: 63
DIQMTQSPSS LSASVGDRVT ITCRASQEIS GYLSWYQQKP GKAPKRLIYA ASTLDSGVPS    60
RFSGSGSGTE FTLTISSLQP EDFATYYCLQ YDSYPYTFGQ GTKLEIK                 107

SEQ ID NO: 64                   moltype = AA  length = 471
FEATURE                         Location/Qualifiers
REGION                          1..471
                                note = Description of Artificial Sequence: Synthetic
                                  polypeptide
source                          1..471
                                mol_type = protein
                                organism = synthetic construct
SEQUENCE: 64
MDMRVPAQLL GLLLLWLRGA RCQVQLVESG GGLVKPGGSL RLSCAASGFT FSDYAMSWIR    60
QAPGKGLEWV STISDGGTYT YYPDSVKGRF TISRDNAKNS LYLQMNSLRA EDTAVYYCAR   120
EWGDYDGFDY WGQGTLVTVS SASTKGPSVF PLAPSSKSTS GGTAALGCLV KDYFPEPVTV   180
SWNSGALTSG VHTFPAVLQS SGLYSLSSVV TVPSSSLGTQ TYICNVNHKP SNTKVDKRVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K            471

SEQ ID NO: 65                   moltype = AA  length = 236
FEATURE                         Location/Qualifiers
REGION                          1..236
                                note = Description of Artificial Sequence: Synthetic
                                  polypeptide
source                          1..236
                                mol_type = protein
                                organism = synthetic construct
SEQUENCE: 65
MDMRVPAQLL GLLLLWLRGA RCDIQMTQSP SSLSASVGDR VTITCRASQE ISGYLSWYQQ    60
KPGKAPKRLI YAASTLDSGV PSRFSGSGSG TEFTLTISSL QPEDFATYYC LQYDSYPYTF   120
GQGTKLEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 66                   moltype = AA  length = 451
FEATURE                         Location/Qualifiers
REGION                          1..451
                                note = mAb
source                          1..451
                                mol_type = protein
                                organism = synthetic construct
SEQUENCE: 66
QVQLQQSGSE LKKPGASVKV SCKASGYTFT NYGMNWVKQA PGQGLKWMGW INTYTGEPTY    60
TDDFKGRFAF SLDTSVSTAY LQISSLKADD TAVYFCARGG FGSSYWYFDV WGQGSLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 67                   moltype = AA  length = 121
FEATURE                         Location/Qualifiers
REGION                          1..121
                                note = mAb
source                          1..121
                                mol_type = protein
                                organism = synthetic construct
SEQUENCE: 67
```

```
QVQLQQSGSE LKKPGASVKV SCKASGYTFT NYGMNWVKQA PGQGLKWMGW INTYTGEPTY   60
TDDFKGRFAF SLDTSVSTAY LQISSLKADD TAVYFCARGG FGSSYWYFDV WGQGSLVTVS  120
S                                                                 121

SEQ ID NO: 68            moltype = AA  length = 5
FEATURE                  Location/Qualifiers
REGION                   1..5
                         note = mAb
source                   1..5
                         mol_type = protein
                         organism = synthetic construct
SEQUENCE: 68
NYGMN                                                              5

SEQ ID NO: 69            moltype = AA  length = 17
FEATURE                  Location/Qualifiers
REGION                   1..17
                         note = mAb
source                   1..17
                         mol_type = protein
                         organism = synthetic construct
SEQUENCE: 69
WINTYTGEPT YTDDFKG                                                 17

SEQ ID NO: 70            moltype = AA  length = 12
FEATURE                  Location/Qualifiers
REGION                   1..12
                         note = mAb
source                   1..12
                         mol_type = protein
                         organism = synthetic construct
SEQUENCE: 70
GGFGSSYWYF DV                                                      12

SEQ ID NO: 71            moltype = AA  length = 214
FEATURE                  Location/Qualifiers
REGION                   1..214
                         note = mAb
source                   1..214
                         mol_type = protein
                         organism = synthetic construct
SEQUENCE: 71
DIQLTQSPSS LSASVGDRVS ITCKASQDVS IAVAWYQQKP GKAPKLLIYS ASYRYTGVPD   60
RFSGSGSGTD FTLTISSLQP EDFAVYYCQQ HYITPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 72            moltype = AA  length = 110
FEATURE                  Location/Qualifiers
REGION                   1..110
                         note = mAb
source                   1..110
                         mol_type = protein
                         organism = synthetic construct
SEQUENCE: 72
DIQLTQSPSS LSASVGDRVS ITCKASQDVS IAVAWYQQKP GKAPKLLIYS ASYRYTGVPD   60
RFSGSGSGTD FTLTISSLQP EDFAVYYCQQ HYITPLTFGA GTKVEIKRTV             110

SEQ ID NO: 73            moltype = AA  length = 11
FEATURE                  Location/Qualifiers
REGION                   1..11
                         note = mAb
source                   1..11
                         mol_type = protein
                         organism = synthetic construct
SEQUENCE: 73
KASQDVSIAV A                                                       11

SEQ ID NO: 74            moltype = AA  length = 7
FEATURE                  Location/Qualifiers
REGION                   1..7
                         note = mAb
source                   1..7
                         mol_type = protein
                         organism = synthetic construct
SEQUENCE: 74
SASYRYT                                                            7

SEQ ID NO: 75            moltype = AA  length = 9
```

| FEATURE | Location/Qualifiers |
|---|---|
| REGION | 1..9 |
| | note = mAb |
| source | 1..9 |
| | mol_type = protein |
| | organism = synthetic construct |

SEQUENCE: 75
QQHYITPLT                                                                 9

| SEQ ID NO: 76 | moltype = AA  length = 451 |
|---|---|
| FEATURE | Location/Qualifiers |
| REGION | 1..451 |
| | note = mAb |
| source | 1..451 |
| | mol_type = protein |
| | organism = synthetic construct |

SEQUENCE: 76
QVQLVQSGAE VKKPGASVKV SCKASGYTFT TAGMQWVRQA PGQGLEWMGW INTHSGVPKY    60
AEDFKGRVTI SADTSTSTAY LQLSSLKSED TAVYYCARSG FGSSYWYFDV WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

| SEQ ID NO: 77 | moltype = AA  length = 121 |
|---|---|
| FEATURE | Location/Qualifiers |
| REGION | 1..121 |
| | note = mAb |
| source | 1..121 |
| | mol_type = protein |
| | organism = synthetic construct |

SEQUENCE: 77
QVQLVQSGAE VKKPGASVKV SCKASGYTFT TAGMQWVRQA PGQGLEWMGW INTHSGVPKY    60
AEDFKGRVTI SADTSTSTAY LQLSSLKSED TAVYYCARSG FGSSYWYFDV WGQGTLVTVS   120
S                                                                  121

| SEQ ID NO: 78 | moltype = AA  length = 5 |
|---|---|
| FEATURE | Location/Qualifiers |
| REGION | 1..5 |
| | note = mAb |
| source | 1..5 |
| | mol_type = protein |
| | organism = synthetic construct |

SEQUENCE: 78
TAGMQ                                                                     5

| SEQ ID NO: 79 | moltype = AA  length = 17 |
|---|---|
| FEATURE | Location/Qualifiers |
| REGION | 1..17 |
| | note = mAb |
| source | 1..17 |
| | mol_type = protein |
| | organism = synthetic construct |

SEQUENCE: 79
WINTHSGVPK YAEDFKG                                                       17

| SEQ ID NO: 80 | moltype = AA  length = 12 |
|---|---|
| FEATURE | Location/Qualifiers |
| REGION | 1..12 |
| | note = mAb |
| source | 1..12 |
| | mol_type = protein |
| | organism = synthetic construct |

SEQUENCE: 80
SGFGSSYWYF DV                                                            12

| SEQ ID NO: 81 | moltype = AA  length = 214 |
|---|---|
| FEATURE | Location/Qualifiers |
| REGION | 1..214 |
| | note = mAb |
| source | 1..214 |
| | mol_type = protein |
| | organism = synthetic construct |

SEQUENCE: 81
DIQMTQSPSS LSASVGDRVT ITCKASQDVS TAVAWYQQKP GKAPKLLIYS ASYRYTGVPS    60
RFSGSGSGTD FTLTISSLQP EDFAVYYCQQ HYITPLTFGQ GTKLEIKRTV AAPSVFIFPP   120
SDEQLKSGTA SVVCLLNNFY PREAKVQWKV DNALQSGNSQ ESVTEQDSKD STYSLSSTLT   180

```
LSKADYEKHK VYACEVTHQG LSSPVTKSFN RGEC                                           214

SEQ ID NO: 82           moltype = AA   length = 110
FEATURE                 Location/Qualifiers
REGION                  1..110
                        note = mAb
source                  1..110
                        mol_type = protein
                        organism = synthetic construct
SEQUENCE: 82
DIQMTQSPSS LSASVGDRVT ITCKASQDVS TAVAWYQQKP GKAPKLLIYS ASYRYTGVPS                60
RFSGSGSGTD FTLTISSLQP EDFAVYYCQQ HYITPLTFGQ GTKLEIKRTV                          110

SEQ ID NO: 83           moltype = AA   length = 11
FEATURE                 Location/Qualifiers
REGION                  1..11
                        note = mAb
source                  1..11
                        mol_type = protein
                        organism = synthetic construct
SEQUENCE: 83
KASQDVSTAV A                                                                    11

SEQ ID NO: 84           moltype = AA   length = 7
FEATURE                 Location/Qualifiers
REGION                  1..7
                        note = mAb
source                  1..7
                        mol_type = protein
                        organism = synthetic construct
SEQUENCE: 84
SASYRYT                                                                         7

SEQ ID NO: 85           moltype = AA   length = 9
FEATURE                 Location/Qualifiers
REGION                  1..9
                        note = mAb
source                  1..9
                        mol_type = protein
                        organism = synthetic construct
SEQUENCE: 85
QQHYITPLT                                                                       9

SEQ ID NO: 86           moltype = AA   length = 450
FEATURE                 Location/Qualifiers
REGION                  1..450
                        note = Antibody heavy chain
source                  1..450
                        mol_type = protein
                        organism = synthetic construct
SEQUENCE: 86
EVQLVESGGG LVQPGGSLRL SCAASGFNIK DTYIHWVRQA PGKGLEWVAR IYPTNGYTRY                60
ADSVKGRFTI SADTSKNTAY LQMNSLRAED TAVYYCSRWG GDGFYAMDYW GQGTLVTVSS                120
ASTKGPSVFP LAPSSKSTSG GTAALGCLVK DYFPEPVTVS WNSGALTSGV HTFPAVLQSS                180
GLYSLSSVVT VPSSSLGTQT YICNVNHKPS NTKVDKKVEP KSCDKTHTCP PCPAPELLGG                240
PSVFLFPPKP KDTLMISRTP EVTCVVVDVS HEDPEVKFNW YVDGVEVHNA KTKPREEQYN                300
STYRVVSVLT VLHQDWLNGK EYKCKVSNKA LPAPIEKTIS KAKGQPREPQ VYTLPPSREE                360
MTKNQVSLTC LVKGFYPSDI AVEWESNGQP ENNYKTTPPV LDSDGSFFLY SKLTVDKSRW                420
QQGNVFSCSV MHEALHNHYT QKSLSLSPGK                                                450

SEQ ID NO: 87           moltype = AA   length = 214
FEATURE                 Location/Qualifiers
REGION                  1..214
                        note = Antibody light chain
source                  1..214
                        mol_type = protein
                        organism = synthetic construct
SEQUENCE: 87
DIQMTQSPSS LSASVGDRVT ITCRASQDVN TAVAWYQQKP GKAPKLLIYS ASFLYSGVPS                60
RFSGSRSGTD FTLTISSLQP EDFATYYCQQ HYTTPPTFGQ GTKVEIKRTV AAPSVFIFPP                120
SDEQLKSGTA SVVCLLNNFY PREAKVQWKV DNALQSGNSQ ESVTEQDSKD STYSLSSTLT                180
LSKADYEKHK VYACEVTHQG LSSPVTKSFN RGEC                                           214

SEQ ID NO: 88           moltype = AA   length = 448
FEATURE                 Location/Qualifiers
REGION                  1..448
                        note = Antibody heavy chain
source                  1..448
                        mol_type = protein
```

```
                              organism = synthetic construct
SEQUENCE: 88
EVQLVESGGG LVQPGGSLRL SCAASGFTFT DYTMDWVRQA PGKGLEWVAD VNPNSGGSIY      60
NQRFKGRFTL SVDRSKNTLY LQMNSLRAED TAVYYCARNL GPSFYFDYWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPG                                        448

SEQ ID NO: 89           moltype = AA  length = 214
FEATURE                 Location/Qualifiers
REGION                  1..214
                        note = Antibody light chain
source                  1..214
                        mol_type = protein
                        organism = synthetic construct
SEQUENCE: 89
DIQMTQSPSS LSASVGDRVT ITCKASQDVS IGVAWYQQKP GKAPKLLIYS ASYRYTGVPS      60
RFSGSGSGTD FTLTISSLQP EDFATYYCQQ YYIYPYTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 90           moltype = AA  length = 244
FEATURE                 Location/Qualifiers
source                  1..244
                        mol_type = protein
                        organism = Homo sapiens
SEQUENCE: 90
MAAAASPAFL LCLPLLHLLS GWSRAGWVDT HCLCYDFIIT PKSRPEPQWC EVQGLVDERP      60
FLHYDCVNHK AKAFASLGKK VNVTKTWEEQ TETLRDVVDF LKGQLLDIQV ENLIPIEPLT     120
LQARMSCEHE AHGHGRGSWQ FLFNGQKFLL FDSNNRKWTA LHPGAKKMTE KWEKNRDVTM     180
FFQKISLGDC KMWLEEFLMY WEQMLDPTKP PSLAPGTTQP KAMATTLSPW SLLIIFLCFI     240
LAGR                                                                  244

SEQ ID NO: 91           moltype = AA  length = 233
FEATURE                 Location/Qualifiers
REGION                  1..233
                        note = Mutated Protein
source                  1..233
                        mol_type = protein
                        organism = synthetic construct
SEQUENCE: 91
SEKSEEINEK DLRKKSELQG TALGNLKQIY YYNSKAITSS EKSADQFLTN TLLFKGFFTG      60
HPWYNDLLVD LGSTAATSEY EGSSVDLYGA YYGYQCAGGT PNKTACMYGG VTLHDNNRLT     120
EEKKVPINLW IDGKQTTVPI DKVKTSKKEV TVQELDLQAR HYLHGKFGLY NSDSFGGKVQ     180
RGLIVFHSSE GSTVSYDLFD AQGQYPDTLL RIYRDNTTIS STSLSISLYL YTT            233

SEQ ID NO: 92           moltype = AA  length = 233
FEATURE                 Location/Qualifiers
REGION                  1..233
                        note = Mutated Protein
source                  1..233
                        mol_type = protein
                        organism = synthetic construct
SEQUENCE: 92
SEKSEEINEK DLRKKSELQG TALGNLKQIY YYNEKAKTEN KESHDQFLQH TILFKGFFTD      60
HSWYNDLLVD FDSKDIVDKY KGKKVDLYGA YYGYQCAGGT PNKTACMYGG VTLHDNNRLT     120
EEKKVPINLW LDGKQNTVPL ETVKTNKKNV TVQELDLQAR RYLQEKYNLY NSDVFDGKVQ     180
RGLIVFHTST EPSVNYDLFG AQGQYSNTLL RIYRDNKTIN SENMHIAIYL YTS            233

SEQ ID NO: 93           moltype = AA  length = 679
FEATURE                 Location/Qualifiers
REGION                  1..679
                        note = Conjugated Protein
REGION                  460..679
                        note = MISC_FEATURE - Light Chain
source                  1..679
                        mol_type = protein
                        organism = synthetic construct
SEQUENCE: 93
QVQLQQPGAE LVRPGASVKL SCKASGYTFT NYWINWVKQR PGQGLEWIGN IYPSYIYTNY      60
NQEFKDKVTL TVDESSSTAY MQLSSPTSED SAVYYCTRSP YGYDEYGLDY WGQGTSVTVS     120
SAKTTPPSVY PLAPGSAAQT NSMVTLGCLV KGYFPEPVTV TWNSGSLSSG VHTFPAVLQS     180
DLYTLSSSVT VPSSTWPSET VTCNVAHPAS STKVDKKIVP RDSGGPSEKS EEINEKDLRK     240
KSELQGTALG NLKQIYYYNE KAKTENKESH DQFLQHTILF KGFFTDHSWY NDLLVDFDSK     300
DIVDKYKGKK VDLYGAYYGY QCAGGTPNKT ACMYGGVTLH DNNRLTEEKK VPINLWLDGK     360
QNTVPLETVK TNKKNVTVQE LDLQARRYLQ EKYNLYNSDV FDGKVQRGLI VFHTSTEPSV     420
```

```
NYDLFGAQGQ YSNTLLRIYR DNKTINSENM HIDIYLYTSD IVMTQSPSSL TVTAGEKVTM   480
NCKSSQSLLN SRNQKNYLTW YQQKPGQPPK LLIYWASTRE SGVPDRFTGS GSGTDFTLTI   540
SSVQAEDLAV YYCQNDYVYP LTFGAGTKLE LKRADAAPTV SIFPPSSEQL TSGGASVVCF   600
LNNFYPKDIN VKWKIDGSER QNGVLNSWTD QDSKDSTYSM SSTLTLTKDE YERHNSYTCE   660
ATHKTSTSPI VKSFNRNES                                                679

SEQ ID NO: 94           moltype = AA  length = 672
FEATURE                 Location/Qualifiers
REGION                  1..672
                        note = Mutated and Conjugated Protein
REGION                  459..672
                        note = MISC_FEATURE - Light Chain
source                  1..672
                        mol_type = protein
                        organism = synthetic construct
SEQUENCE: 94
EVQLQQSGPD LVKPGASVKI SCKASGYSFT GYYMHWVKQS HGKSLEWIGR INPNNGVTLY    60
NQKFKDKAIL TVDKSSTTAY MELRSLTSED SAVYYCARST MITNYVMDYW GQVTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNEK AKTENKESHD QFLQHTILFK GFFTDHSWYN DLLVDFDSKD   300
IVDKYKGKKV DLYGAYYGYQ CAGGTPNKTA CMYGGVTLHD NNRLTEEKKV PINLWLDGKQ   360
NTVPLETVKT NKKNVTVQEL DLQARRYLQE KYNLYNSDVF DGKVQRGLIV FHTSTEPSVN   420
YDLFGAQGQY SNTLLRIYRD NKTINSENMH IAIYLYTSSI VMTQTPTSLL VSAGDRVTIT   480
CKASQSVSND VAWYQQKPGQ SPKLLISYTS SRYAGVPDRF SGSGSGTDFT LTISSVQAED   540
LAVYFCQQDY NSPPTFGGGT KLEIKRADAA PTVSIFPPSS EQLTSGGASV VCFLNNFYPK   600
DINVKWKIDG SERQNGVLNS WTDQDSKDST YSMSSTLTLT KDEYERHNSY TCEATHKTST   660
SPIVKSFNRN ES                                                      672

SEQ ID NO: 95           moltype = AA  length = 672
FEATURE                 Location/Qualifiers
REGION                  1..672
                        note = Mutated and Conjugated Protein
REGION                  459..672
                        note = MISC_FEATURE - Light Chain
source                  1..672
                        mol_type = protein
                        organism = synthetic construct
SEQUENCE: 95
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNSK AITSSEKSAD QFLTNTLLFK GFFTGHPWYN DLLVDLGSTA   300
ATSEYEGSSV DLYGAYYGYQ CAGGTPNKTA CMYGGVTLHD NNRLTEEKKV PINLWIDGKQ   360
TTVPIDKVKT SKKEVTVQEL DLQARHYLHG KFGLYNSDSF GGKVQRGLIV FHSSEGSTVS   420
YDLFGAQGQY PDTLLRIYRD NTTISSTSLS ISLYLYTTSI VMTQTPTSLL VSAGDRVTIT   480
CKASQSVSND VAWYQQKPGQ SPKLLISYTS SRYAGVPDRF SGSGYGTDFT LTISSVQAED   540
AAVYFCQQDY NSPPTFGGGT KLEIKRADAA PTVSIFPPSS EQLTSGGASV VCFLNNFYPK   600
DINVKWKIDG SERQNGVLNS WTDQDSKDST YSMSSTLTLT KDEYERHNSY TCEATHKTST   660
SPIVKSFNRN ES                                                      672

SEQ ID NO: 96           moltype = AA  length = 458
FEATURE                 Location/Qualifiers
REGION                  1..458
                        note = Synthetic polypeptide
source                  1..458
                        mol_type = protein
                        organism = synthetic construct
SEQUENCE: 96
EVQLQQSGPD LVKPGASVKI SCKASGYSFT GYYMHWVKQS PGKGLEWIGR INPNNGVTLY    60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DSGGPSEKSE EINEKDLRKK   240
SELQGTALGN LKQIYYYNSK AITSSEKSAD QFLTNTLLFK GFFTGHPWYN DLLVDLGSTA   300
ATSEYEGSSV DLYGAYYGYQ CAGGTPNKTA CMYGGVTLHD NNRLTEEKKV PINLWIDGKQ   360
TTVPIDKVKT SKKEVTVQEL DLQARHYLHG KFGLYNSDSF GGKVQRGLIV FHSSEGSTVS   420
YDLFGAQGQY PDTLLRIYRD NTTISSTSLS ISLYLYTT                           458

SEQ ID NO: 97           moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 97
SIVMTQTPTS LLVSAGDRVT ITCKASQSVS NDVAWYQQKP GQSPKLLISY TSSRYAGVPD    60
RFSGSGYGTD FTLTISSVQA EDAAVYFCQQ DYNSPPTFGG GTKLEIKRAD AAPTVSIFPP   120
```

```
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNES                              214

SEQ ID NO: 98              moltype = AA  length = 233
FEATURE                    Location/Qualifiers
REGION                     1..233
                           note = Mutated Protein
source                     1..233
                           mol_type = protein
                           organism = synthetic construct
SEQUENCE: 98
SEKSEEINEK DLRKKSELQG TALGNLKQIY YYNEKAITEN KESDDQFLEN TLLFKGFFTG   60
HPWYNDLLVD LGSKDATNKY KGKKVDLYGA YYGYQCAGGT PNKTACMYGG VTLHDNNRLT   120
EEKKVPINLW IDGKQTTVPI DKVKTSKKEV TVQELDLQAR HYLHGKFGLY NSDSFGGKVQ   180
RGLIVFHSSE GSTVSYDLFD AQGQYPDTLL RIYRDNKTIN SENLHIALYL YTT          233

SEQ ID NO: 99              moltype = AA  length = 215
FEATURE                    Location/Qualifiers
REGION                     1..215
                           note = Synthetic polypeptide
source                     1..215
                           mol_type = protein
                           organism = synthetic construct
SEQUENCE: 99
SIVMTQTPTS LLVSAGDRVT ITCKASQSVS NDVAWYQQKP GQSPKLLISY TSSRYAGVPD   60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNESK                             215

SEQ ID NO: 100             moltype = AA  length = 215
FEATURE                    Location/Qualifiers
REGION                     1..215
                           note = Synthetic polypeptide
source                     1..215
                           mol_type = protein
                           organism = synthetic construct
SEQUENCE: 100
SIVMTQTPTS LLVSAGDRVT ITCKASQSVS NDVAWYQQKP GQSPKLLISY TSSRYAGVPD   60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNESC                             215

SEQ ID NO: 101             moltype = AA  length = 216
FEATURE                    Location/Qualifiers
REGION                     1..216
                           note = Synthetic polypeptide
source                     1..216
                           mol_type = protein
                           organism = synthetic construct
SEQUENCE: 101
SIVMTQTPTS LLVSAGDRVT ITCKASQSVS NDVAWYQQKP GQSPKLLISY TSSRYAGVPD   60
RFSGSGYGTD FTLTISSVQA EDAAVYFCQQ DYNSPPTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNESKC                            216

SEQ ID NO: 102             moltype = AA  length = 222
FEATURE                    Location/Qualifiers
REGION                     1..222
                           note = Synthetic polypeptide
source                     1..222
                           mol_type = protein
                           organism = synthetic construct
SEQUENCE: 102
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
LYTLSSSVTV PSSTWPSETV TCNVAHPASS TKVDKKIVPR DS                     222

SEQ ID NO: 103             moltype = AA  length = 225
FEATURE                    Location/Qualifiers
REGION                     1..225
                           note = Synthetic polypeptide
source                     1..225
                           mol_type = protein
                           organism = synthetic construct
SEQUENCE: 103
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS   120
AKTTPPSVYP LAPGSAAQTN SMVTLGCLVK GYFPEPVTVT WNSGSLSSGV HTFPAVLQSD   180
```

```
LYTLSSSVTV PSSTWPSETV TCNVAHPASS TKVDKKIVPR DSGGP              225

SEQ ID NO: 104          moltype = AA  length = 223
FEATURE                 Location/Qualifiers
REGION                  1..223
                        note = Synthetic polypeptide
source                  1..223
                        mol_type = protein
                        organism = synthetic construct
SEQUENCE: 104
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSK                   223

SEQ ID NO: 105          moltype = AA  length = 226
FEATURE                 Location/Qualifiers
REGION                  1..226
                        note = Synthetic polypeptide
source                  1..226
                        mol_type = protein
                        organism = synthetic construct
SEQUENCE: 105
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPK                226

SEQ ID NO: 106          moltype = AA  length = 223
FEATURE                 Location/Qualifiers
REGION                  1..223
                        note = Synthetic polypeptide
source                  1..223
                        mol_type = protein
                        organism = synthetic construct
SEQUENCE: 106
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSC                   223

SEQ ID NO: 107          moltype = AA  length = 226
FEATURE                 Location/Qualifiers
REGION                  1..226
                        note = Synthetic polypeptide
source                  1..226
                        mol_type = protein
                        organism = synthetic construct
SEQUENCE: 107
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPC                226

SEQ ID NO: 108          moltype = AA  length = 224
FEATURE                 Location/Qualifiers
REGION                  1..224
                        note = Synthetic polypeptide
source                  1..224
                        mol_type = protein
                        organism = synthetic construct
SEQUENCE: 108
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSKC                  224

SEQ ID NO: 109          moltype = AA  length = 227
FEATURE                 Location/Qualifiers
REGION                  1..227
                        note = Synthetic polypeptide
source                  1..227
                        mol_type = protein
                        organism = synthetic construct
SEQUENCE: 109
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPKC               227
```

```
SEQ ID NO: 110            moltype = AA  length = 673
FEATURE                   Location/Qualifiers
REGION                    1..673
                          note = Mutated and Conjugated Protein
REGION                    459..672
                          note = MISC_FEATURE - Light Chain
source                    1..673
                          mol_type = protein
                          organism = synthetic construct
SEQUENCE: 110
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPSEKSE EINEKDLRKK  240
SELQGTALGN LKQIYYYNSK AITSSEKSAD QFLTNTLLFK GFFTGHPWYN DLLVDLGSTA  300
ATSEYEGSSV DLYGAYYGYQ CAGGTPNKTA CMYGGVTLHD NNRLTEEKKV PINLWIDGKQ  360
TTVPIDKVKT SKKEVTVQEL DLQARHYLHG KFGLYNSDSF GGKVQRGLIV FHSSEGSTVS  420
YDLFDAQGQY PDTLLRIYRD NTTISSTSLS ISLYLYTTSI VMTQTPTSLL VSAGDRVTIT  480
CKASQSVSND VAWYQQKPGQ SPKLLISYTS SRYAGVPDRF SGSGYGTDFT LTISSVQAED  540
AAVYFCQQDY NSPPTFGGGT KLEIKRADAA PTVSIFPPSS EQLTSGGASV VCFLNNFYPK  600
DINVKWKIDG SERQNGVLNS WTDQDSKDST YSMSSTLTLT KDEYERHNSY TCEATHKTST  660
SPIVKSFNRN ESK                                                    673

SEQ ID NO: 111            moltype = AA  length = 459
FEATURE                   Location/Qualifiers
REGION                    1..459
                          note = Synthetic polypeptide
source                    1..459
                          mol_type = protein
                          organism = synthetic construct
SEQUENCE: 111
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPSEKSE EINEKDLRKK  240
SELQGTALGN LKQIYYYNSK AITSSEKSAD QFLTNTLLFK GFFTGHPWYN DLLVDLGSTA  300
ATSEYEGSSV DLYGAYYGYQ CAGGTPNKTA CMYGGVTLHD NNRLTEEKKV PINLWIDGKQ  360
TTVPIDKVKT SKKEVTVQEL DLQARHYLHG KFGLYNSDSF GGKVQRGLIV FHSSEGSTVS  420
YDLFDAQGQY PDTLLRIYRD NTTISSTSLS ISLYLYTTK                         459

SEQ ID NO: 112            moltype = AA  length = 673
FEATURE                   Location/Qualifiers
REGION                    1..673
                          note = Mutated and Conjugated Protein
REGION                    459..672
                          note = MISC_FEATURE - Light Chain
source                    1..673
                          mol_type = protein
                          organism = synthetic construct
SEQUENCE: 112
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPSEKSE EINEKDLRKK  240
SELQGTALGN LKQIYYYNSK AITSSEKSAD QFLTNTLLFK GFFTGHPWYN DLLVDLGSTA  300
ATSEYEGSSV DLYGAYYGYQ CAGGTPNKTA CMYGGVTLHD NNRLTEEKKV PINLWIDGKQ  360
TTVPIDKVKT SKKEVTVQEL DLQARHYLHG KFGLYNSDSF GGKVQRGLIV FHSSEGSTVS  420
YDLFDAQGQY PDTLLRIYRD NTTISSTSLS ISLYLYTTSI VMTQTPTSLL VSAGDRVTIT  480
CKASQSVSND VAWYQQKPGQ SPKLLISYTS SRYAGVPDRF SGSGYGTDFT LTISSVQAED  540
AAVYFCQQDY NSPPTFGGGT KLEIKRADAA PTVSIFPPSS EQLTSGGASV VCFLNNFYPK  600
DINVKWKIDG SERQNGVLNS WTDQDSKDST YSMSSTLTLT KDEYERHNSY TCEATHKTST  660
SPIVKSFNRN ESC                                                    673

SEQ ID NO: 113            moltype = AA  length = 459
FEATURE                   Location/Qualifiers
REGION                    1..459
                          note = Synthetic polypeptide
source                    1..459
                          mol_type = protein
                          organism = synthetic construct
SEQUENCE: 113
EVQLQQSGPD LVKPGASVKI SCKASGYSFT GYYMHWVKQS PGKGLEWIGR INPNNGVTLY   60
NQKFKDKATL TVDKSSTTAY MELRSLTSED SAVYYCARST MITNYVMDYW GQGTSVTVSS  120
AKTTPPSVYP LAPGSAAQTN SMVTLGCLVK GYFPEPVTVT WNSGSLSSGV HTFPAVLQSD  180
LYTLSSSVTV PSSTWPSETV TCNVAHPASS TKVDKKIVPR DSGGPSEKSE EINEKDLRKK  240
SELQGTALGN LKQIYYYNSK AITSSEKSAD QFLTNTLLFK GFFTGHPWYN DLLVDLGSTA  300
ATSEYEGSSV DLYGAYYGYQ CAGGTPNKTA CMYGGVTLHD NNRLTEEKKV PINLWIDGKQ  360
TTVPIDKVKT SKKEVTVQEL DLQARHYLHG KFGLYNSDSF GGKVQRGLIV FHSSEGSTVS  420
```

```
                YDLFDAQGQY PDTLLRIYRD NTTISSTSLS ISLYLYTTC                    459

SEQ ID NO: 114              moltype = AA   length = 674
FEATURE                     Location/Qualifiers
REGION                      1..674
                            note = Mutated and Conjugated Protein
REGION                      459..672
                            note = MISC_FEATURE - Light Chain
source                      1..674
                            mol_type = protein
                            organism = synthetic construct
SEQUENCE: 114
EVQLQQSGPD LVKPGASVKI SCKASGYSFT GYYMHWVKQS PGKGLEWIGR INPNNGVTLY            60
NQKFKDKATL TVDKSSTTAY MELRSLTSED SAVYYCARST MITNYVMDYW GQGTSVTVSS            120
AKTTPPSVYP LAPGSAAQTN SMVTLGCLVK GYFPEPVTVT WNSGSLSSGV HTFPAVLQSD            180
LYTLSSSVTV PSSTWPSETV TCNVAHPASS TKVDKKIVPR DSGGPSEKSE EINEKDLRKK            240
SELQGTALGN LKQIYYYNSK AITSSEKSAD QFLTNTLLFK GFFTGHPWYN DLLVDLGSTA            300
ATSEYEGSSV DLYGAYYGYQ CAGGTPNKTA CMYGGVTLHD NNRLTEEKKV PINLWIDGKQ            360
TTVPIDKVKT SKKEVTVQEL DLQARHYLHG KFGYNSDSF GGKVQRGLIV FHSSEGSTVS             420
YDLFDAQGQY PDTLLRIYRD NTTISSTSLS ISLYLYTTSI VMTQTPTSLL VSAGDRVTIT            480
CKASQSVSND VAWYQQKPGQ SPKLLISYTS SRYAGVPDRF SGSGYGTDFT LTISSVQAED            540
AAVYFCQQDY NSPPTFGGGT KLEIKRADAA PTVSIFPPSS EQLTSGGASV VCFLNNFYPK            600
DINVKWKIDG SERQNGVLNS WTDQDSKDST YSMSSTLTLT KDEYERHNSY TCEATHKTST            660
SPIVKSFNRN ESKC                                                             674

SEQ ID NO: 115              moltype = AA   length = 460
FEATURE                     Location/Qualifiers
REGION                      1..460
                            note = Synthetic polypeptide
source                      1..460
                            mol_type = protein
                            organism = synthetic construct
SEQUENCE: 115
EVQLQQSGPD LVKPGASVKI SCKASGYSFT GYYMHWVKQS PGKGLEWIGR INPNNGVTLY            60
NQKFKDKATL TVDKSSTTAY MELRSLTSED SAVYYCARST MITNYVMDYW GQGTSVTVSS            120
AKTTPPSVYP LAPGSAAQTN SMVTLGCLVK GYFPEPVTVT WNSGSLSSGV HTFPAVLQSD            180
LYTLSSSVTV PSSTWPSETV TCNVAHPASS TKVDKKIVPR DSGGPSEKSE EINEKDLRKK            240
SELQGTALGN LKQIYYYNSK AITSSEKSAD QFLTNTLLFK GFFTGHPWYN DLLVDLGSTA            300
ATSEYEGSSV DLYGAYYGYQ CAGGTPNKTA CMYGGVTLHD NNRLTEEKKV PINLWIDGKQ            360
TTVPIDKVKT SKKEVTVQEL DLQARHYLHG KFGYNSDSF GGKVQRGLIV FHSSEGSTVS             420
YDLFDAQGQY PDTLLRIYRD NTTISSTSLS ISLYLYTTKC                                  460

SEQ ID NO: 116              moltype = AA   length = 5
FEATURE                     Location/Qualifiers
source                      1..5
                            mol_type = protein
                            organism = synthetic construct
SEQUENCE: 116
GYYMH                                                                       5

SEQ ID NO: 117              moltype = AA   length = 17
FEATURE                     Location/Qualifiers
source                      1..17
                            mol_type = protein
                            organism = synthetic construct
SEQUENCE: 117
RINPNNGVTL YNQKFKD                                                          17

SEQ ID NO: 118              moltype = AA   length = 11
FEATURE                     Location/Qualifiers
source                      1..11
                            mol_type = protein
                            organism = synthetic construct
SEQUENCE: 118
STMITNYVMD Y                                                                11

SEQ ID NO: 119              moltype = AA   length = 11
FEATURE                     Location/Qualifiers
source                      1..11
                            mol_type = protein
                            organism = synthetic construct
SEQUENCE: 119
KASQSVSNDV A                                                                11

SEQ ID NO: 120              moltype = AA   length = 7
FEATURE                     Location/Qualifiers
source                      1..7
                            mol_type = protein
                            organism = synthetic construct
```

```
SEQUENCE: 120
YTSSRYA                                                                        7

SEQ ID NO: 121          moltype = AA  length = 9
FEATURE                 Location/Qualifiers
source                  1..9
                        mol_type = protein
                        organism = synthetic construct
SEQUENCE: 121
QQDYNSPPT                                                                      9

SEQ ID NO: 122          moltype = AA  length = 29
FEATURE                 Location/Qualifiers
source                  1..29
                        mol_type = protein
                        organism = synthetic construct
SEQUENCE: 122
KISGGGGSGG  GGSGGGGSGG  GGSGGGGSS                                             29

SEQ ID NO: 123          moltype = AA  length = 21
FEATURE                 Location/Qualifiers
source                  1..21
                        mol_type = protein
                        organism = synthetic construct
SEQUENCE: 123
SPNSASHSGS  APQTSSAPGS  Q                                                     21

SEQ ID NO: 124          moltype = AA  length = 452
FEATURE                 Location/Qualifiers
source                  1..452
                        mol_type = protein
                        organism = synthetic construct
SEQUENCE: 124
EVQLLESGGG  LVQPGGSLRL  SCAVSGFTFN  SFAMSWVRQA  PGKGLEWVSA  ISGSGGGTYY        60
ADSVKGRFTI  SRDNSKNTLY  LQMNSLRAED  TAVYFCAKDK  ILWFGEPVFD  YWGQGTLVTV       120
SSASTKGPSV  FPLAPSSKST  SGGTAALGCL  VKDYFPEPVT  VSWNSGALTS  GVHTFPAVLQ       180
SSGLYSLSSV  VTVPSSSLGT  QTYICNVNHK  PSNTKVDKRV  EPKSCDKTHT  CPPCPAPELL       240
GGPSVFLFPP  KPKDTLMISR  TPEVTCVVVD  VSHEDPEVKF  NWYVDGVEVH  NAKTKPREEQ       300
YNSTYRVVSV  LTVLHQDWLN  GKEYKCKVSN  KALPAPIEKT  ISKAKGQPRE  PQVYTLPPSR       360
EEMTKNQVSL  TCLVKGFYPS  DIAVEWESNG  QPENNYKTTP  PVLDSDGSFF  LYSKLTVDKS       420
RWQQGNVFSC  SVMHEALHNH  YTQKSLSLSP  GK                                       452

SEQ ID NO: 125          moltype = AA  length = 5
FEATURE                 Location/Qualifiers
source                  1..5
                        mol_type = protein
                        organism = synthetic construct
SEQUENCE: 125
SFAMS                                                                          5

SEQ ID NO: 126          moltype = AA  length = 17
FEATURE                 Location/Qualifiers
source                  1..17
                        mol_type = protein
                        organism = synthetic construct
SEQUENCE: 126
AISGSGGGTY  YADSVKG                                                           17

SEQ ID NO: 127          moltype = AA  length = 13
FEATURE                 Location/Qualifiers
source                  1..13
                        mol_type = protein
                        organism = synthetic construct
SEQUENCE: 127
DKILWFGEPV  FDY                                                               13

SEQ ID NO: 128          moltype = AA  length = 214
FEATURE                 Location/Qualifiers
source                  1..214
                        mol_type = protein
                        organism = synthetic construct
SEQUENCE: 128
EIVLTQSPAT  LSLSPGERAT  LSCRASQSVS  SYLAWYQQKP  GQAPRLLIYD  ASNRATGIPA        60
RFSGSGSGTD  FTLTISSLEP  EDFAVYYCQQ  RSNWPPTFGQ  GTKVEIKRTV  AAPSVFIFPP       120
SDEQLKSGTA  SVVCLLNNFY  PREAKVQWKV  DNALQSGNSQ  ESVTEQDSKD  STYSLSSTLT       180
LSKADYEKHK  VYACEVTHQG  LSSPVTKSFN  RGEC                                     214

SEQ ID NO: 129          moltype = AA  length = 11
FEATURE                 Location/Qualifiers
```

```
source                  1..11
                        mol_type = protein
                        organism = synthetic construct
SEQUENCE: 129
RASQSVSSYL A                                                            11

SEQ ID NO: 130          moltype = AA  length = 7
FEATURE                 Location/Qualifiers
source                  1..7
                        mol_type = protein
                        organism = synthetic construct
SEQUENCE: 130
DASNRAT                                                                  7

SEQ ID NO: 131          moltype = AA  length = 9
FEATURE                 Location/Qualifiers
source                  1..9
                        mol_type = protein
                        organism = synthetic construct
SEQUENCE: 131
QQRSNWPPT                                                                9

SEQ ID NO: 132          moltype = AA  length = 449
FEATURE                 Location/Qualifiers
source                  1..449
                        mol_type = protein
                        organism = synthetic construct
SEQUENCE: 132
QVQLVQSGAE VAKPGTSVKL SCKASGYTFT DYWMQWVKQR PGQGLEWIGT IYPGDGDTGY        60
AQKFQGKATL TADKSSKTVY MHLSSLASED SAVYYCARGD YYGSNSLDYW GQGTSVTVSS       120
ASTKGPSVFP LAPSSKSTSG GTAALGCLVK DYFPEPVTVS WNSGALTSGV HTFPAVLQSS       180
GLYSLSSVVT VPSSSLGTQT YICNVNHKPS NTKVDKKVEP KSCDKTHTCP PCPAPELLGG       240
PSVFLFPPKP KDTLMISRTP EVTCVVVDVS HEDPEVKFNW YVDGVEVHNA KTKPREEQYN       300
STYRVVSVLT VLHQDWLNGK EYKCKVSNKA LPAPIEKTIS KAKGQPREPQ VYTLPPSRDE       360
LIKNQVSLIC LVKGFYPSDI AVEWESNGQP ENNYKTTPPV LDSDGSFFLY SKLTVDKSRW       420
QQGNVFSCSV MHEALHNHYT QKSLSLSPG                                        449

SEQ ID NO: 133          moltype = AA  length = 5
FEATURE                 Location/Qualifiers
source                  1..5
                        mol_type = protein
                        organism = synthetic construct
SEQUENCE: 133
DYWMQ                                                                    5

SEQ ID NO: 134          moltype = AA  length = 17
FEATURE                 Location/Qualifiers
source                  1..17
                        mol_type = protein
                        organism = synthetic construct
SEQUENCE: 134
TIYPGDGDTG YAQKFQG                                                      17

SEQ ID NO: 135          moltype = AA  length = 11
FEATURE                 Location/Qualifiers
source                  1..11
                        mol_type = protein
                        organism = synthetic construct
SEQUENCE: 135
GDYYGSNSLD Y                                                            11

SEQ ID NO: 136          moltype = AA  length = 214
FEATURE                 Location/Qualifiers
source                  1..214
                        mol_type = protein
                        organism = synthetic construct
SEQUENCE: 136
DIVMTQSHLS MSTSLGDPVS ITCKASQDVS TVVAWYQQKP GQSPRRLIYS ASYRYIGVPD        60
RFTGSGAGTD FTFTISSVQA EDLAVYYCQQ HYSPPYTFGG GTKLEIKRTV AAPSVFIFPP       120
SDEQLKSGTA SVVCLLNNFY PREAKVQWKV DNALQSGNSQ ESVTEQDSKD STYSLSSTLT       180
LSKADYEKHK VYACEVTHQG LSSPVTKSFN RGEC                                  214

SEQ ID NO: 137          moltype = AA  length = 11
FEATURE                 Location/Qualifiers
source                  1..11
                        mol_type = protein
                        organism = synthetic construct
SEQUENCE: 137
KASQDVSTVV A                                                            11
```

```
SEQ ID NO: 138          moltype = AA  length = 7
FEATURE                 Location/Qualifiers
source                  1..7
                        mol_type = protein
                        organism = synthetic construct
SEQUENCE: 138
SASYRYI                                                                 7

SEQ ID NO: 139          moltype = AA  length = 9
FEATURE                 Location/Qualifiers
source                  1..9
                        mol_type = protein
                        organism = synthetic construct
SEQUENCE: 139
QQHYSPPYT                                                               9
```

What is claimed is:

1. A bifunctional chelator compound comprising a formula

R-L₁-M wherein R is a reactive group,
wherein L₁ comprises

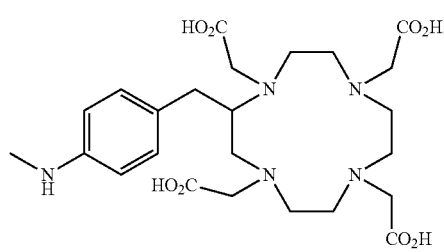

wherein n is 1 or an integer greater than 1, and
wherein M is a chelator moiety.

2. The bifunctional chelator compound of claim 1, wherein M comprises a formula selected from a group consisting of:

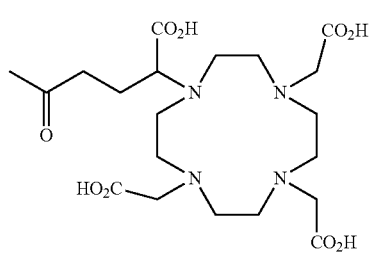
(IIIA)

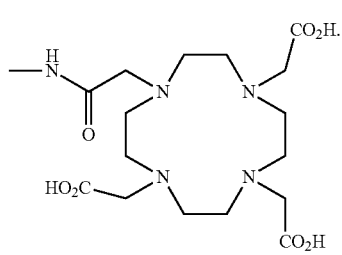
(IIIB)

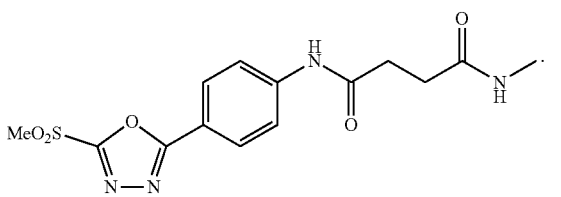
(IIIC)

3. The bifunctional chelator compound of claim 1, wherein R comprises a formula selected from a group consisting of:

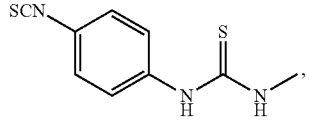
(IIID)

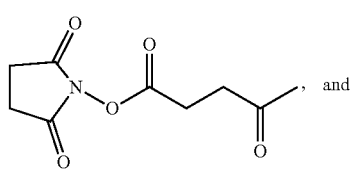
(IIIE)

and (IIIF)

4. The bifunctional chelator compound of claim 1, wherein n is an integer in a range of 1 to 10.

5. The bifunctional chelator of claim 1, further comprising at least one radionuclide, wherein the at least one radionuclide is chelated by the chelator moiety, and wherein the at least one radionuclide comprises $^{134}$Ce, $^{43}$Sc, $^{44}$Sc, $^{47}$Sc, $^{55}$Co, $^{60}$CU, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rb, $^{109}$Pd, $^{111}$In, $^{117m}$Sn, $^{149}$Pm, $^{149}$Tb, $^{153}$Sm, $^{177}$Lu, $^{186}$Re, $^{188}$Re, $^{199}$Ab, $^{201}$Tl, $^{203}$Pb, $^{212}$Pb, $^{212}$Bi, $^{213}$Bi, $^{225}$Ac, $^{211}$At, or $^{227}$Th.

6. A conjugate of the bifunctional chelator compound of claim 1 with a molecule comprising a primary amine group or a free thiol group.

7. The conjugate of claim 6, wherein the molecule comprising a primary amine group or a free thiol group is a peptide or a protein.

8. The conjugate of claim 6, wherein the molecule comprising a primary amine group or a free thiol group comprises an antibody, a monoclonal antibody, an antigen-binding fragment of an antibody, an antigen-binding fragment of a monoclonal antibody, an immunoglobulin heavy chain, an immunoglobulin heavy chain variable region, immunoglobulin light chain, an immunoglobulin light chain variable region, a nanobody, a scFv molecule, or an antibody mimetic protein.

9. The bifunctional chelator compound of claim 2, comprising the formula:

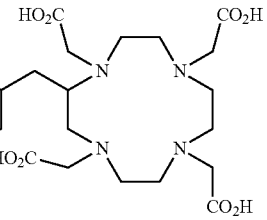
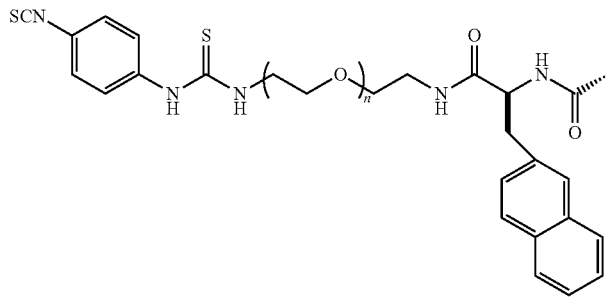

wherein n is 1 or an integer greater than 1.

10. The bifunctional chelator compound of claim 9, wherein n is an integer in a range of 1 to 10.

11. A conjugate of the bifunctional chelator compound of claim 9 with a molecule comprising a primary amine group.

12. The conjugate of claim 11, wherein the molecule comprising a primary amine group is a peptide or a protein.

13. The conjugate of claim 11, wherein the molecule comprising a primary amine group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

14. The conjugate of claim 11, further comprising a radionuclide chelated by the chelator moiety, wherein the radionuclide is $^{134}$Ce, $^{43}$Sc, $^{44}$Sc, $^{47}$Sc, $^{55}$Co, $^{60}$CU, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{166}$Ho, $^{89}$Zr, $^{97}$Ru, $^{105}$Rb, $^{109}$Pd, $^{111}$In, $^{117m}$Sn, $^{149}$Pm, $^{149}$Tb, $^{153}$Sm, $^{177}$Lu, $^{201}$Tl, $^{203}$Pb, $^{212}$Pb, $^{212}$Bi, $^{213}$Bi, $^{225}$Ac, or $^{227}$Th.

15. A method for manufacturing a chelator-conjugated molecule, comprising:
reacting a molecule comprising at least one primary amine group with a bifunctional chelator compound according to claim 1 wherein the reactive group is a N-hydroxysuccinimide ester (NHS) reactive group or an isothiocyanate (SCN) reactive group, to conjugate the bifunctional chelator compound to the molecule; or
reacting a molecule comprising at least one free thiol group with a bifunctional chelator compound according to claim 1 wherein the reactive group is a phenyloxadiazolyl methylsulfone (PODS) reactive group, to conjugate the bifunctional chelator compound to the molecule.

16. A method for manufacturing a chelator-conjugated molecule, comprising:
reacting a molecule comprising at least one free thiol group with a bifunctional chelator compound according to claim 1, wherein the reactive group is a phenyloxadiazolyl methylsulfone (PODS) reactive group, to conjugate the bifunctional chelator compound to the molecule; and reducing a disulfide bond to generate the at least one free thiol group of the molecule.

17. The method of claim 15, wherein
the molecule comprising at least one primary amine group is a peptide or a protein, and
the molecule comprising at least one free thiol group is a peptide or a protein.

18. The method of claim 15, wherein
the molecule comprising at least one primary amine group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein; and
the molecule comprising at least one free thiol group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

19. The method of claim 15, further comprising chelating a radionuclide to the chelator moiety of the bifunctional chelator compound before or after performing the conjugation.

20. A method for manufacturing a chelator-conjugated molecule, comprising the step of:
reacting a molecule comprising at least one primary amine group with a bifunctional chelator compound comprising the structure

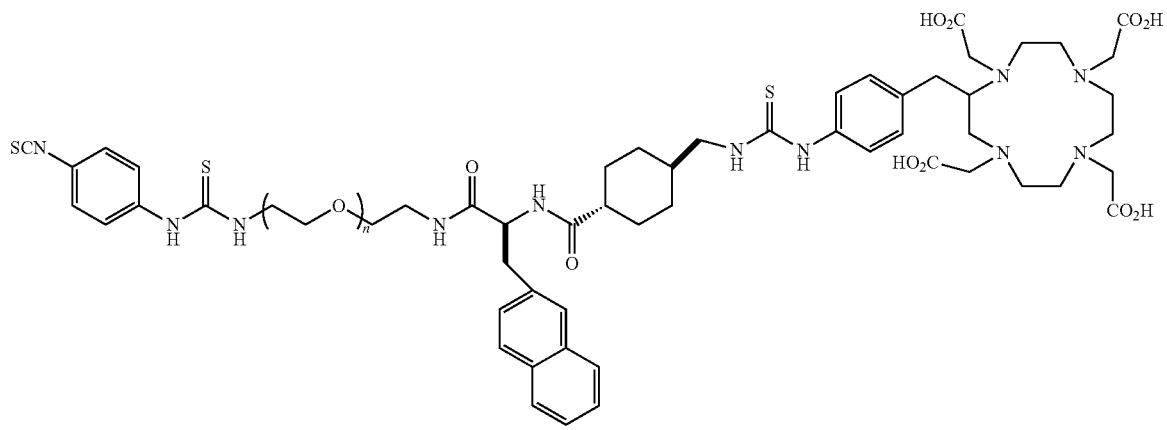

wherein n is 1 or an integer greater than 1.

21. The method of claim 20, wherein n is an integer in a range of 1 to 10.

22. The method of claim 20, wherein the molecule comprising at least one primary amine group is a peptide or a protein.

23. The method of claim 20, wherein the molecule comprising at least one primary amine group is an antibody, a monoclonal antibody, an antigen-binding fragment of an antibody, an antigen-binding fragment of a monoclonal antibody, an immunoglobulin heavy chain, an immunoglobulin heavy chain variable region, an immunoglobulin light chain, an immunoglobulin light chain variable region, a nanobody, a scFv molecule, or an antibody mimetic protein.

24. The method of claim 20, further comprising the step of:
chelating a radionuclide to the chelator-conjugated molecule.

25. The method of claim 24, wherein the radionuclide is $^{134}$Ce, $^{43}$Sc, $^{44}$Sc, $^{47}$Sc, $^{55}$Co, $^{60}$CU, $^{61}$Cu, $^{62}$Cu, $^{64}$Cu, $^{67}$Cu, $^{66}$Ga, $^{67}$Ga, $^{68}$Ga, $^{86}$Y, $^{87}$Y, $^{90}$Y, $^{166}$Ho, $^{89}$Zr, $^{97}$Ru, $^{105}$Rh, $^{109}$Pd, $^{111}$In, $^{117m}$Sn, $^{149}$Pm, $^{149}$Tb, $^{153}$Sm, $^{177}$Lu, $^{201}$Tl, $^{203}$Pb, $^{212}$Pb, $^{212}$Bi, $^{213}$Bi, $^{225}$Ac, or $^{227}$Th.

26. The bifunctional chelator compound of claim 2, wherein R comprises a formula selected from a group consisting of:

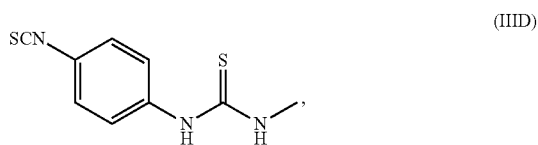 (IIID)

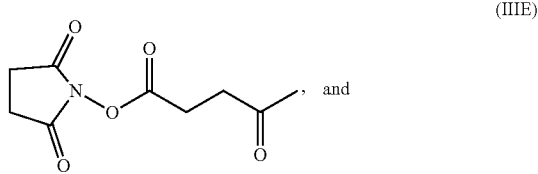 (IIIE)

and

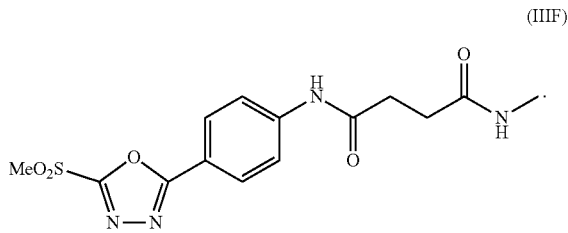 (IIIF)

* * * * *